(12) United States Patent
Yamakawa et al.

(10) Patent No.: US 12,072,069 B2
(45) Date of Patent: Aug. 27, 2024

(54) METHOD FOR USING WHITE LIGHT SOURCE, AND WHITE LIGHT SOURCE

(71) Applicant: Seoul Semiconductor Co., Ltd., Gyeonggi-do (KR)

(72) Inventors: Masahiko Yamakawa, Kanagawa (JP); Kumpei Kobayashi, Kanagawa (JP); Ryoji Tsuda, Kanagawa (JP); Noriaki Yagi, Kanagawa (JP); Kiyoshi Inoue, Kanagawa (JP); Kyung Hee Ye, Gyeonggi-do (KR)

(73) Assignee: Seoul Semiconductor Co., Ltd., Gyeonggi-do (KR)

(*) Notice: Subject to any disclaimer, the term of this patent is extended or adjusted under 35 U.S.C. 154(b) by 0 days.

(21) Appl. No.: 18/241,927

(22) Filed: Sep. 4, 2023

(65) Prior Publication Data
US 2024/0044459 A1 Feb. 8, 2024

Related U.S. Application Data

(63) Continuation of application No. PCT/KR2022/003115, filed on Mar. 4, 2022.

(30) Foreign Application Priority Data

Mar. 4, 2021 (JP) .................. 2021-034434

(51) Int. Cl.
*F21K 9/90* (2016.01)
*F21K 9/64* (2016.01)
*F21Y 115/10* (2016.01)

(52) U.S. Cl.
CPC .................. *F21K 9/90* (2013.01); *F21K 9/64* (2016.08); *F21Y 2115/10* (2016.08)

(58) Field of Classification Search
CPC .......... F21K 9/90; F21K 9/64; F21Y 2115/10
See application file for complete search history.

(56) References Cited

U.S. PATENT DOCUMENTS 8,269,410 B2 * 9/2012 Kijima ............. C09K 11/77742
313/485
2009/0200907 A1 8/2009 Zukauskas et al.
(Continued)

FOREIGN PATENT DOCUMENTS

JP 2010162214 A 7/2010
JP 2020057777 A 4/2020
(Continued)

OTHER PUBLICATIONS

English translation of International Search Report for PCT/KR2022/003115, Jun. 13, 2022, 2 pages.

*Primary Examiner* — Anne M Hines
*Assistant Examiner* — Jose M Diaz
(74) *Attorney, Agent, or Firm* — LaBatt, LLC

(57) ABSTRACT

A white light source and method of use thereof, wherein control of daily rhythm and pleasant lighting can be realized. Amounts of stimulation light emitted from a white light source to the intrinsically photosensitive retinal ganglion cells (ipRGCs) and visual cells of the L cone and M cone, are defined as a melanopic irradiance, an L-cone opic irradiance, and an M-cone opic irradiance, respectively; a ratio of the amounts of the stimulation light is expressed by formula (1); and A is the ratio corresponding to the emission spectrum of the white light source, and B is the ratio corresponding to the radiation spectrum of a black body having the same color temperature as the white light source, an amount of stimulation light emitted to the ipRGC is quantitatively changed by changing the emission intensity of the white light source satisfying formula (2).

(Continued)

Melanopic irradiance/($L$-cone opic irradiance+$M$-cone opic irradiance)  (1)

$0.88 \leq A/B \leq 1.11$  (2).

26 Claims, 32 Drawing Sheets

(56) References Cited

U.S. PATENT DOCUMENTS

| | | |
|---|---|---|
| 2009/0231832 A1 | 9/2009 | Zukauskas et al. |
| 2009/0261710 A1 | 10/2009 | Zukauskas et al. |
| 2017/0208673 A1 | 7/2017 | Schlangen et al. |
| 2018/0073689 A1 | 3/2018 | Soer et al. |
| 2020/0105981 A1 | 4/2020 | Fujio et al. |

FOREIGN PATENT DOCUMENTS

| | | |
|---|---|---|
| JP | 6738796 B2 | 8/2020 |
| KR | 1020190047016 A | 5/2019 |
| WO | 2020210740 A1 | 10/2020 |

\* cited by examiner

FIG. 37

| 7:00 | Lights-on, waking up, washing face, Abreakfast, etc. |
|---|---|
| 8:30 | Club Activity 1 |
| 10:00 | Rest |
| 10:30 | Club Activity 2 |
| 12:00 | Lunch |
| 13:00 | Club Activity 3 |
| 15:00 | Rest |
| 15:30 | Club Activity 4 |
| 17:00 | Bathing, meeting, dinner, etc. |
| 20:00 | Free time |
| 23:00 | Lights-out, sleep |

METHOD FOR USING WHITE LIGHT SOURCE, AND WHITE LIGHT SOURCE

CROSS-REFERENCE TO RELATED APPLICATIONS

This application is a continuation of International Patent Application No. PCT/KR2022/003115, filed on 4 Mar. 2022, which claims the benefit of Japanese Patent Application No. 2021-034434, filed on 4 Mar. 2021, each of which is hereby incorporated by reference for all purposes as if fully set forth herein.

TECHNICAL FIELD

Exemplary embodiments of the present disclosure relate to a method for using a white light source and the white light source. Employing the method of the present disclosure as a method for using a white light source not only provides a comfortable lighting environment for people, but also contributes to maintaining and improving health by maintaining their daily rhythm properly.

BACKGROUND ART

With the development of information terminals, and the like, opportunities to strain the eyes over long periods of time have increased in recent years. Regardless of time or place, people look directly at their smart phone screens, or operate information devices such as PCs under a bright illumination light until late at night even indoors. While this advancement in lifestyle is convenient, it also creates negative aspects. For example, there is a problem of blue light due to the illumination light. This is a phenomenon that, when lighting is used for a long time before going to bed, falling asleep becomes delayed and sufficient sleep time is not secured. It occurs when the eyes and brain are stimulated by a strong blue component of the illumination light, causing confusion in the person's daily rhythm.

In recent years, one of the factors causing the above problem is the change in lifestyle described above. And the other one is the problem of a light source.

Recently, the use of an LED as the light source has become mainstream. When a blue LED was developed and appeared on the market, an incandescent light bulb and a fluorescent lamp began to disappear from the market, and from now on into the future, LED lighting is in an overwhelming position. The reason why the LED has replaced an existing light source is because it is highly safe as it does not use harmful mercury gas like a fluorescent lamp, does not burn out in a short period of time like an incandescent bulb, and further, it has characteristics of low power consumption. However, a current LED lighting is not superior to the existing light source in all respects. When the use of incandescent light bulbs was mainstream, it was a world completely unrelated to the dangers of blue light. Of course, the lifestyles back then and now are different, and there is a big difference in addition to this. An emission spectrum distribution of the LED light source is significantly different from that of the incandescent light bulb. The incandescent light bulb emits light by heating a filament to a high temperature, which has a characteristic of a flexible-curved emission spectrum that includes light of all wavelength components. And when a white light emission from the incandescent light bulb was observed within a limited wavelength range, an extremely large amount of light of a specific wavelength was not included, or there was no extreme shortage of other wavelength components.

Meanwhile, a light emission of an LED is a conversion of electrical energy into light without heat generation inside a semiconductor material, and a major characteristic of the emission spectrum by such LED is that it exhibits a spectral shape with a sharp emission peak at a specific wavelength. A light source that emits white light as a product currently on the market synthesizes white light by combining light emissions of LEDs and phosphors, but a blue component of white light emission mainly uses direct light from LEDs. In this type of LED light source, only blue emission of a specific wavelength exhibits a protruding spectral shape among an overall flat emission spectrum. Just as three primary colors of light are red, green, and blue, an emission spectrum of white light necessarily includes a blue emission component at a certain rate. However, a most preferable emission spectrum of white light is that each emission component is balanced without being biased towards a specific emission color component. Meanwhile, in a case of the LED light source described above, a total amount of blue light is not different from that of ordinary white light, but it has an uneven spectral distribution in which blue light of a specific wavelength is extremely high and blue light of other wavelength components is low.

Meanwhile, it is known that a daily rhythm of a human body is influenced by an intensity of blue light received by the human body, but an amount of blue light received by the human body is not equal to all blue wavelengths. Since a light reception peak wavelength of the human body and a peak emission wavelength of blue LED are close together, the human body receives strong blue light when using the LED lighting. In other words, when receiving white light of a same color temperature from LED light, sunlight, or even from the incandescent light bulb, the human body feels that it has received same white light from any light sources, but in reality, a stimulus from blue light from the LED light source is much stronger than that from sunlight or the incandescent light bulb. This strong blue light of a specific wavelength is becoming a factor that causes blue light hazard in the LED lighting.

As mentioned above, in order to eliminate the problem of blue light hazard due to the illumination light, improving characteristics of the emission spectrum of illumination light has become an urgent priority. Regarding spectral distributions of all white light including blue light, it is unclear what a desirable spectral shape is. In addition, among blue light hazards, it is important to be able to select emission spectral characteristics over time in order to prevent disruption of daily rhythms, but a desirable spectral shape corresponding to outdoor light environments and people's lifestyles is also unclear.

The following two patent documents disclose a lighting device that may change brightness and luminous color in accordance with changes in life rhythm or environment. Patent Document 1 discloses a lighting device system that is configured to automatically control a color temperature and illuminance to preset conditions according to daily life rhythm and environmental changes. In addition, Patent Document 2 discloses a lighting system that is configured to reproduce changes in the outdoor environment indoors. However, the environmental changes covered in these documents are those that can be responded by changing the color temperature and illuminance of a light source on an hourly or half-day basis in the referred Document 1, and changes in sunlight that are employed only during sunrise and sunset times in the referred Document 2, which were not sufficient at all. In addition, since the fluorescent lamp, the LED, the organic EL, and the like were used as light sources, the only characteristic that can be strictly controlled is color temperature. Accordingly, it is not known that anything about the spectral shape of the illumination light or a method for using it that can properly maintain a person's daily rhythm or prevent blue light hazards, and the like.

LITERATURE RELATED TO PRIOR ART

Patent Document

[Patent Document 1] Patent Laid-open Publication No. 2011-23339
[Patent Document 2] Patent Laid-open Publication No. 2015-106515

DETAILED DESCRIPTION

Technical Problem

The present disclosure aims to provide a comfortable lighting environment for people and at the same time, to realize illumination light that may properly maintain their daily rhythm and contribute to the improvement of health through receiving light. For this reason, by sufficiently investigating and examining effects of illumination light on the human body, it aims to make more fundamental improvement to a conventional light source and a method of its use.

Exemplary embodiments of the present disclosure provide a white light source and a method for using a white light source that may safely and easily provide lighting with precise control of daily rhythm and comfort in living spaces such as general households, by reviewing effects of changes in a spectral shape of light emission on the human body.

Technical Solution

As a result of examining a relationship between human sleep and α-opic irradiance, it was found that the α-opic irradiance, which is a white light source, has an optimal value for each color temperature in terms of its effect on human sleep, and that there is some difference in optimal values. It was found that as a white light source that provides a favorable sleeping effect to people, a most preferable light source has a range that exhibits values on a straight line connecting α-opic irradiance, which is an optimal value for each color temperature, and values within a certain range on both sides of the straight line.

Although the preferable range of the present disclosure can be specified through the above, managing it using the above ratio as a method for using a light source is inconvenient as an index for managing characteristics of general lighting. Because the optimal range varies slightly for each color temperature, it becomes necessary to use white light sources with different color temperatures separately by comparing them with their coefficient table. Therefore, as the method for using the light source of the present disclosure, a method of standardizing a range of a preferable α-opic irradiance ratio to an optimal value of each color temperature was proposed. When checking color rendering coefficient (Ra) of the optimal value for each color temperature, they all show values close to 100, and thus, a value obtained by calculating an α-opic irradiance ratio shown by blackbody radiation at each color temperature corresponding to Ra of 100 was proposed as a reference value for standardization.

A range of preferable characteristics found by the present disclosure as the white light source that provides the favorable sleeping effect to people may be expressed as follows.

$$0.88 \leq A/B \leq 1.11$$

In the above equation, A is a white light source, B is a blackbody radiation with a same color temperature as that of the white light source, and it represents a ratio of each α-opic irradiance (L cone opic irradiance/(L cone opic irradiance+M cone opic irradiance)).

According to an embodiment, a method for using a white light source that emits light with a correlated color temperature in a range of 2500K or more to 10000K or less is provided. When amounts of stimulation light that a white light source irradiates to photoreceptor cells of endogenous photosensitive retinal ganglion cells (ipRGC), L cone, and M cone among human photoreceptor cells are set as melanopic irradiance, L cone opic irradiance, and M cone opic irradiance, respectively, a ratio of the stimulation light amounts is expressed by the following formula (1), and when the ratio corresponding to the emission spectrum of the above-described white light source is A, and the ratio corresponding to a spectrum of blackbody radiation having a same color temperature as that of the white light source is B, a method for using the white light source that quantitatively changes the amount of stimulation light irradiated to the ipRGC by changing an emission intensity of the white light source satisfying the following formula (2) is provided.

(Equation 1)

$$\text{Melanopic irradiance}/(L \text{ cone opic irradiance} + M \text{ cone opic irradiance}) \tag{1}$$

$$0.88 \leq A/B \leq 1.11 \tag{2}$$

In addition, according to an embodiment, a white light source that emits light with the correlated color temperature in the range of 2500K or more to 10000K or less is provided. When amounts of stimulation light that a white light source irradiates to photoreceptor cells of ipRGC, L cone, and M-cone among human photoreceptor cells are set as melanopic irradiance, L cone optic irradiance, and M-cone optic irradiance, respectively, a ratio of the stimulation light amounts is expressed by the following formula (1), and when the ratio corresponding to the emission spectrum of the above-described white light source is A, and the ratio corresponding to the spectrum of blackbody radiation having the same color temperature as that of the white light source is B, the following formula (2) is satisfied.

(Equation 2)

$$\text{Melanopic irradiance}/(L \text{ cone opic irradiance} + M \text{ cone opic irradiance}) \tag{1}$$

$$0.88 \leq A/B \leq 1.11 \tag{2}$$

Further, according to an embodiment, a white light source that emits white light with the correlated color temperature in the range of 2500K or more to 10000K or less is provided. The white light source includes a substrate, a housing portion provided on a surface of the substrate, an electrode disposed on the surface or a rear surface of the substrate, an interconnection pattern disposed on the surface or the rear surface of the substrate, one or more GaN-based LED chips disposed in an electrically connected state to the electrode or the interconnection pattern in the housing portion, and a phosphor layer including various kinds of phosphors having different luminous colors disposed in the housing portion to directly or indirectly cover a periphery of the LED chip. When amounts of stimulation light that a white light source irradiates to photoreceptor cells of ipRGC, L cone, and M-cone among human photoreceptor cells are set as melanopic irradiance, L cone optic irradiance, and M-cone optic irradiance, respectively, and a ratio of the stimulation light amounts is expressed by the following formula (1), and when the ratio corresponding to the emission spectrum of the above-described white light source is A, and the ratio corresponding to the spectrum of blackbody radiation having the same color temperature as that of the white light source is B, the following formula (3) is satisfied.

(Equation 3)

Melanopic irradiance/($L$ cone opic irradiance+$M$ cone opic irradiance) (1)

$0.88 \leq A/B \leq 1.11$ (2)

Advantageous Effects

A range of α-opic irradiance found in the present disclosure contributes to a proper maintenance of human daily rhythm and health promotion. However, since medical knowledge is required to understand the meaning of an α-opic irradiance value, it is difficult for a user of a light source of lighting to select an optimal light source of lighting by directly using the α-opic irradiance value. In this regard, with the A/B ratio introduced in the present disclosure, the optimal light source corresponding to a color temperature may be easily selected by simply determining the light source with the color temperature suitable for a purpose. Therefore, if a light source is used with an appropriate color temperature according to one's lifestyle pattern, an effect of preventing his or her daily rhythm from being disturbed or improving it may be expected.

In addition, the present disclosure may also provide a white lighting with high color rendering. For the light source of the present disclosure, a range of the optimal light source of lighting for humans is determined based on luminance characteristics of blackbody radiation, but the light source of the present disclosure is not tailored to the luminance characteristics of blackbody radiation. However, high color rendering characteristics close to 100 may be realized only when the A/B ratio is limited within a certain range.

Therefore, by utilizing the method for using the light source of the present disclosure, it is possible to provide illumination light that has comfort and may contribute to maintaining and improving health.

DESCRIPTION OF DRAWINGS

FIG. 37 is a diagram showing a time schedule of a daily rhythm survey subject on a test day.

Figure 1:
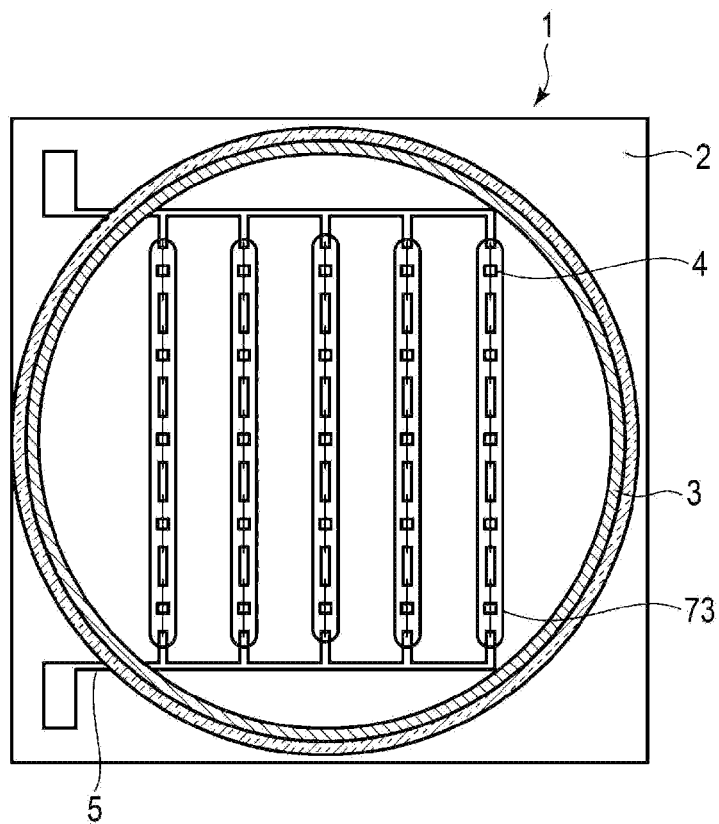
FIG. 1 is a diagram showing a row of LED chips arranged linearly on a substrate.

MODE FOR IMPLEMENTING THE INVENTION (LED Module)

A basic configuration of a white light source of the present disclosure is an LED module. The LED module includes a substrate, an LED chip disposed on the substrate, a phosphor layer formed to cover a periphery of the LED chip, and an electrode and an interconnection pattern for electrically connecting the LED and a driving circuit or driving power source outside the substrate.

(Substrate)

Resin, metal, and ceramics are used as materials for the substrate. As the resin materials, polyetherimide, polyimide, liquid crystal polymer, epoxy, BT resin (bismaleimide triazine resin), silicone, or the like is preferably used. As the ceramic material, silicon nitride, aluminum nitride, alumina, zirconia, glass ceramic, or the like is preferable. Moreover, aluminum, an aluminum alloy, copper, stainless steel, a magnesium alloy, iron, or the like may be used as a metallic material. As for which of these materials to be used, it is preferable to comprehensively judge thermal conductivity, resistance to light in the ultraviolet to violet range, insulation, reflectance, cost, mechanical strength, ease of machining, and the like. In addition, a kind of material which comprises a substrate may be made into 1 type, or 2 or more types.

It is preferable that a reflection layer is formed on a surface of the substrate in terms of light extraction efficiency. The reflection layer may be applied to a substrate surface by dispersing inorganic particles in a binder. As the inorganic particles, it is possible to use white powders such as aluminum oxide, zirconia oxide, titanium oxide and barium oxide. Moreover, a thin film which consists of aluminum or silver may be formed on the surface of the substrate by, for example, a printing method or a vapor deposition method. In this case, it is preferable to cover at least a portion of a surface of the reflection layer such as a metal reflection film with a transparent insulating film.

The reflection layer may be formed using any of the above methods, but it is necessary to make a light reflectance 90% or more, and it is preferable to select a material or a film forming method having as high a light reflectance as possible.

Although the above is an example related to a general substrate material, in the white light source of the present disclosure, a lead frame having a reflection film may be used as a substrate. In this case, a surface of the lead frame is molded with resin, and thus, it may be used as a reflection film by adding a reflection material to the resin. As the resin material, silicone resin or epoxy resin may be used, and as the reflection material, inorganic powder such as aluminum oxide may be used.

In addition, in this disclosure, a distributed Bragg reflector (DBR) may be applied to the surface of the substrate, and the distributed Bragg reflector may be formed by alternately stacking at least two insulating materials having different refractive indices. As the insulating material, silicon oxide, titanium oxide, niobium oxide, or the like may be used. In the present disclosure, when the distributed Bragg reflector is used on the surface of the substrate, it is possible to easily control a reflectance of a target wavelength by controlling a combination of insulating materials forming the distributed Bragg reflector or a thickness between the insulating materials, thereby improving a light efficiency.

(LED Chip)

Figure 49:
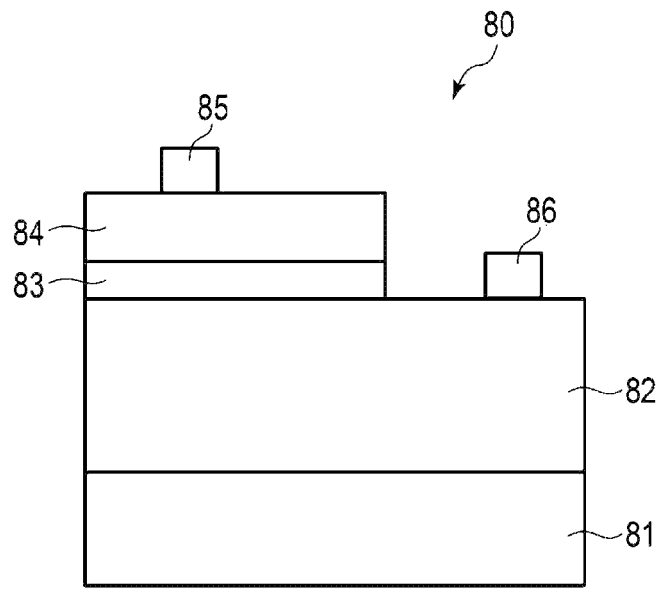
FIG. 49 is a schematic cross-sectional view illustrating an LED chip of the present disclosure.

Examples of an LED used as the white light source of the present disclosure include an LED that emits at least one of ultraviolet or violet light, and a blue light-emitting LED with a peak emission wavelength of 360 nm or more and 470 nm or less. For an LED material, any material may be used as long as it emits light of at least one of ultraviolet, purple, and blue, and for example, GaN-based InGaN, GaN, or AlGaN may be used. Referring to FIG. 49, an LED chip 80 of the present disclosure may include an n-type semiconductor layer 82, an active layer 83, and a p-type semiconductor layer 84 sequentially formed on a substrate 81. If necessary, a buffer layer (not shown in the drawings) may be interposed between the substrate 81 and the n-type semiconductor layer 82.

The substrate 81 may be a growth substrate, and for example, sapphire, silicon, silicon carbide, or a GaN substrates may be used. If necessary, it is possible to form a pattern on a growth surface or a rear surface of the substrate. The n-type semiconductor layer 82 described above may use an AlInGaN-based material, and Si may be doped therein. In addition, the n-type semiconductor layer 82 may be formed of a single layer, but may be formed of a plurality of layers if necessary. For example, it may be formed of an n-type contact layer in ohmic contact with an n-type electrode 86, an n-type electron injection layer, and a superlattice layer (SLs) formed adjacent to an active layer described later. The active layer 83 may be used as a structure such as a single quantum well (SQW) structure or a multi-quantum well structure, or the like, in a region where electrons from the n-type semiconductor layer 82 and holes from the p-type semiconductor layer 84 recombine. The multi-quantum well structure may be formed by alternately stacking a well layer and a barrier layer with a band gap larger than that of the well layer. In this case, the number of repeated stacks is not greatly limited, for example, 2 to 10 repeated stacks are possible. The well layer may use, for example, InGaN, and the barrier layer may use at least one of GaN, InGaN, or AlGaN. For example, as the barrier layer, it is possible to use a combination of at least two or more layers having different band gaps.

In the present disclosure, when the multi-quantum well structure is used, each well layer may emit light of a same peak wavelength having a same band gap, but the band gaps of well layers may also be different from one another, and thus peak wavelengths of light emitted from the well layers may be changed. For example, when compositions of the well layers are InGaN, light having a different peak wavelength for each well layer may be emitted by changing a content of In for each well layer. The p-type semiconductor layer 84 may use an AlInGaN-based material, and Mg may be doped therein.

The n-type semiconductor layer 84 may be formed of a single layer, but it is also possible to form a plurality of layers if necessary. For example, it may include an electron blocking layer (EBL) formed adjacent to the active layer, a hole injection layer, and a p-type contact layer in ohmic contact with a p-type electrode 85. The electron blocking layer may be formed of a material with a relatively large band gap to confine electrons, which move relatively faster than holes, in the active layer, and may be formed of, for example, AlGaN or AlInGaN.

Figure 50:
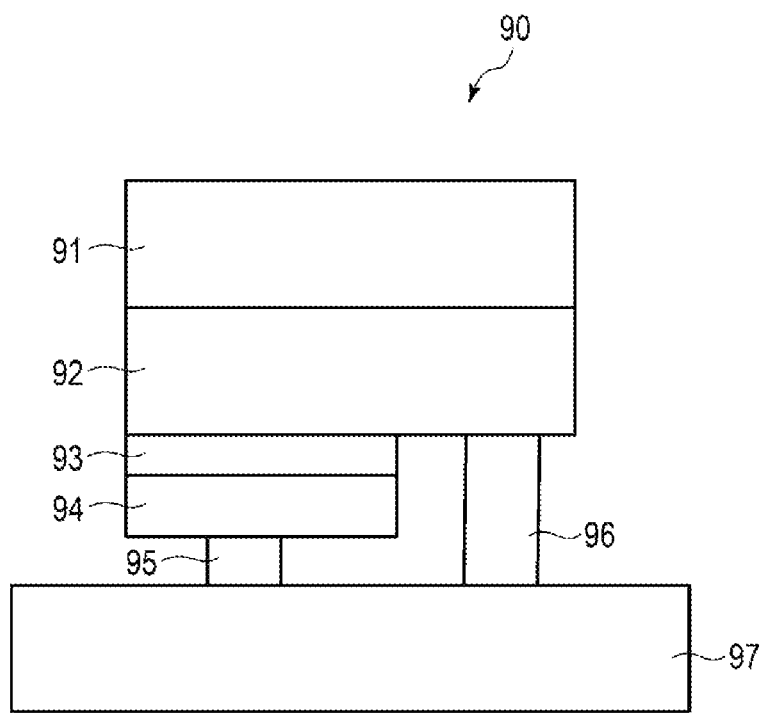
FIG. 50 is a schematic cross-sectional view illustrating another type of LED chip of the present disclosure.

Referring to FIG. 50, an LED chip 90 of the present disclosure may be a flip chip type, and in this case, a growth substrate 91 forms an upper surface of the chip and may be used as a light extraction surface. When a chip of a flip chip type is used in this way, the growth substrate may be removed and a roughened surface may be formed on a surface of a semiconductor layer from which the growth substrate is removed by using PEC etching or the like. This roughened surface may significantly increase light extraction efficiency by reducing total surface reflection of light emitted from the LED chip.

The LED chip 90 of the present disclosure may include an n-type semiconductor layer 92, an active layer 93, and a p-type semiconductor layer 94 sequentially formed on the substrate 91. If necessary, a buffer layer (not shown in the drawings) may be interposed between the substrate 91 and the n-type semiconductor layer 92. The substrate 91 may be a growth substrate, and for example, sapphire, silicon, silicon carbide, or a GaN substrates may be used. If necessary, it is possible to form a pattern on a growth surface or a rear surface of the substrate. The n-type semiconductor layer 92 described above may use an AlInGaN-based material, and Si may be doped therein. In addition, the n-type semiconductor layer 92 may be formed of a single layer, but may be formed of a plurality of layers if necessary. For example, it may be formed of an n-type contact layer in ohmic contact with the n-type electrode 96, an n-type electron injection layer, and a superlattice layer (SLs) formed adjacent to an active layer described later. The active layer 93 may be used as a structure such as a single quantum well (SQW) structure or a multi-quantum well structure, or the like, in a region where electrons from the n-type semiconductor layer 92 and holes from the p-type semiconductor layer 94 recombine. The multi-quantum well structure may be formed by alternately stacking a well layer and a barrier layer with a band gap larger than that of the well layer. In this case, the number of repeated stacks is not greatly limited, for example, 2 to 10 repeated stacks are possible. The well layer may use, for example, InGaN, and the barrier layer may use at least one of GaN, InGaN, or AlGaN. For example, as the barrier layer, it is possible to use a combination of at least two or more layers having different band gaps.

In the present disclosure, when the multi-quantum well structure is used, each well layer may emit light of a same peak wavelength having a same band gap, but the band gap of each well layer may also be changed because the band gap of each well layer is different. For example, when a composition of the well layer is InGaN, light having a different peak wavelength for each well layer may be emitted by changing a content of In for each well layer.

The p-type semiconductor layer 94 may use an AlInGaN-based material, and Mg may be doped therein. The n-type semiconductor layer 94 may be formed of a single layer, but it is also possible to form a plurality of layers if necessary. For example, it may include an electron blocking layer (EBL) formed adjacent to the active layer, a hole injection layer, and a p-type contact layer in ohmic contact with a p-type electrode 95. It is possible to form the electron blocking layer of a material with a relatively large band gap to confine electrons, which move relatively faster than holes, in the active layer, and it is possible to form it of, for example, AlGaN or AlInGaN. The LED chip 90 of the present disclosure may be flip-bonded to a submount substrate 97 as shown in FIG. 50.

In the light source of the present disclosure, it is important to suppress an intensity range of melanopic irradiance that occupies in white light emission within a certain value, but since a photoreceptive response of melanopsin included in ipRGC is highest in a blue wavelength range, it becomes important to be able to precisely control a spectral shape of this wavelength range. However, since a peak emission of an LED has a spectral shape with a sharp peak emission at a specific wavelength, when a peak emission wavelength of the LED matches the blue wavelength band described above, an emission intensity thereof becomes excessive, which may adversely affect a daily rhythm. From this point of view, it is preferable to obtain white light emission by combining phosphor light emission with an LED that emits light in one of ranges from ultraviolet to violet. According to this combination, it is possible to use a light emission of an LED for a shorter wavelength of purple or less, and a light emission of a phosphor for a longer wavelength of blue or more. In this case, the light emission of the phosphor exhibits a flatter emission spectrum than that of the LED, and a type of spectrum shape may be changed in various ways, and thus, a spectral shape of blue light or white light may be more strictly controlled.

When the spectrum shape is considered to be important, it is advantageous to use an ultraviolet or purple LED, but when brightness (power consumption) is considered to be important, it is better to use a blue LED. This is because for a luminous efficiency of the LED itself, the blue light emitting LED is significantly superior to the ultraviolet or purple light emitting LED. However, in that case, it is necessary to devise a way to make excessive blue light emission less noticeable, and one way to do so is to use several LED chips. A most common use of LED chips is to use several LED chips with a single peak wavelength, but in the present disclosure, several LED chips with different peak emission wavelengths are combined. In this case, one LED chip may have a larger peak emission wavelength of approximately 10 nm or more compared to a peak emission wavelength of another LED chip. In a case where white light is obtained by combining blue light from an LED and green light or red light of a phosphor that is emitted by being excited by a portion of the blue light, a gap or a trough in an emission spectrum thereof tends to occur between the LED and the phosphor. When LED light emission is converted to phosphor light emission, in principle, it is excited with stronger energy and converted into light with weaker energy. Therefore, light of a same wavelength does not occur when excited by light of a same wavelength, and it is always converted from light of a shorter wavelength to light of a longer wavelength, moreover, energy conversion entails loss, and thus, there is a gap between the wavelengths before and after conversion. In this case, when a shape of the emission spectrum of the LED is a broad shape that emits light in a wide wavelength range, there may be an overlap between an excitation spectrum and the emission spectrum, but since the light emission of the LED is a sharp shape limited to a specific wavelength, the gap or trough in light emission occurs between the emission wavelengths of the LED and the phosphor, that is, between blue and green (for example, cyan). In addition, this gap causes only the light emission of the LED to protrude from the shape of white light emission spectrum, which adversely affects the daily rhythm of the human body. As a countermeasure to this, the spectrum shape may be flattened by filling an entire blue wavelength band with a light emission of multiple LEDs.

Although various combinations of LEDs and phosphors may be used in the light source of the present disclosure, it is important to consider how to flatten the spectral shape of the blue wavelength band adjust its intensity arbitrarily.

For this reason, the light source of the present disclosure may use several LED chips in combination with various phosphors, and the several LED chips may emit light with different peak wavelengths.

In addition, the light source of the present disclosure may be used in combination with an LED chip having a single peak wavelength or a combination of a phosphor having a peak wavelength adjacent to the LED chip having multiple peak wavelengths.

(Chip Arrangement and Circuit Configuration)

Figure 2:
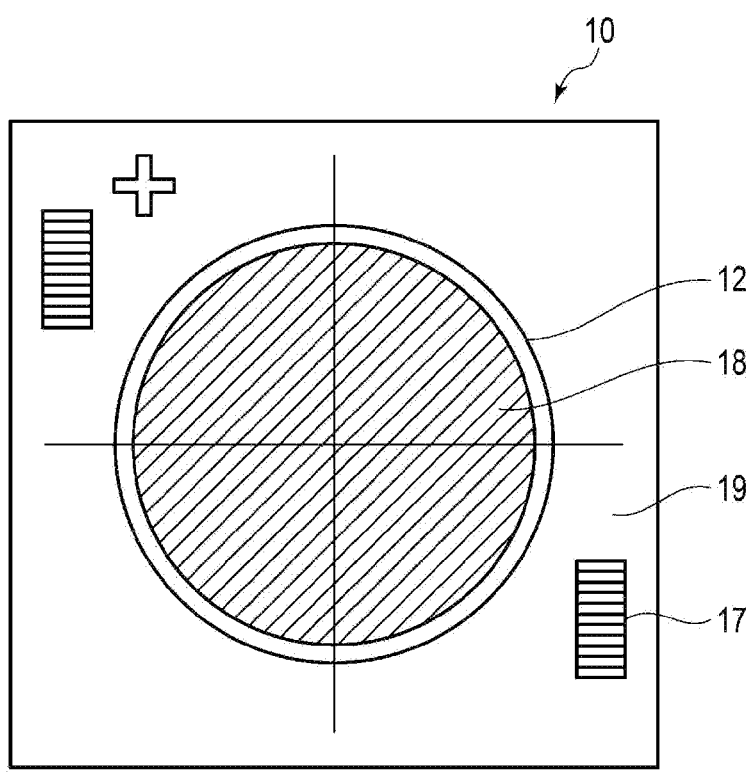
FIG. 2 is a diagram showing an appearance of an LED module.
Figure 3:
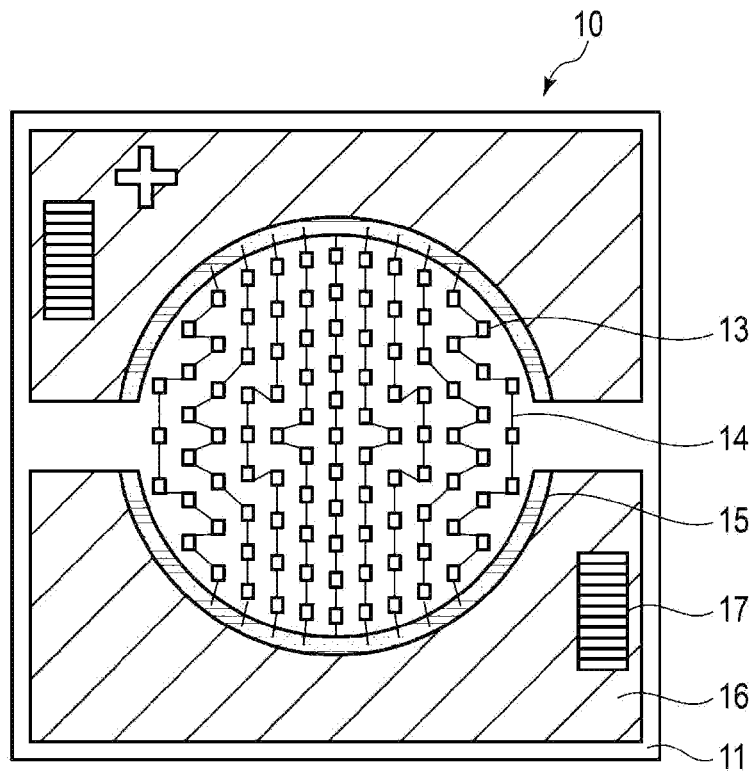
FIG. 3 is a diagram showing interconnections and an LED chip arrangement in an LED module.

In an LED module 1 of the present disclosure, for example, as shown in FIG. 1, a plurality of LED chips 4 may be arranged in a linear shape in a housing portion 3 installed on a surface of a substrate 2. A conductive portion 5 is formed as an electrode on the substrate 2, and each of the LED chips 4 is connected to the electrode. A row of chips may be more than one row. Several chip rows may be arranged depending on the number of chips used. An example thereof is shown in FIGS. 2 and 3. An LED module 10 includes an aluminum substrate 11 that also serves as a reflection layer, LED chips 13 arranged in a matrix shape in a region surrounded by a dam 12 on a surface of the substrate 11, a bonding interconnection 14 for electrically connecting the LED chips, a bonding pad portion 15 electrically connected to the bonding interconnection 14, an interconnection pattern 16 installed on the surface of the substrate 11 and electrically connected to the bonding pad portion 15, an electrode 17 electrically connected to the interconnection pattern 16, a phosphor layer 18 filled in the dam 12, and directly covering a plurality of LED chips 13, and a solder resist layer 19 covering the interconnection pattern 16 of the substrate 11. Surfaces of the bonding pad portion 15 and the electrode 17 are plated with Au. As described above, several chip rows are arranged in a matrix form in FIG. 3, for example. It is preferable to arrange the LED chips at as high a density as possible, but when a distance between the LED chips is too close, it is not desirable because mutual absorption of LED light emission between the LED chips occurs, and to promote dissipation of heat generated by the LED chips during continuous lighting, it is desirable to arrange the LED chips at appropriate intervals.

In addition, an arrangement of the chips is not limited to a linear or matrix form, and a high-density arrangement may be similarly made even when arranged in a houndstooth lattice form or the like. In FIG. 3, each of the LED chips is connected with an electrode while being connected with a wire. The electrode has a specific pattern and also serves as a conductive portion on the substrate. At least several metal materials made of copper, silver, silver alloy, gold, or the like are used as materials for the conductive portion, and it is preferable that an Au film is formed on surfaces of at least some of the metal materials for a purpose of preventing corrosion. The Au film may be formed using any of a printing method, a vapor deposition method, and a plating method. The electrode portion may be constituted with a laminated body of a prepreg and metal foil. In addition, it is preferable that a white solder resist film having the above-described insulation characteristics and favorable resistance to UV rays is formed on an outermost surface of the electrode. The dam 12 may be formed of resin on the substrate and a reflective material may be added to the resin. Silicone resin, epoxy resin, or the like may be used as a resin material, and inorganic powders such as aluminum oxide and titanium oxide may be used as the reflective material.

Although a typical example was given above about a method of electrically connecting LEDs, the LED module of this invention is not limited to the above. For example, LED chips may be flip-chip bonded to a substrate. In this case, there is an advantage that a mounting area may be reduced compared to a method of connecting them with metal wire. Heat from the chip may be easily transferred to the substrate, and thus, it has also favorable heat dissipation characteristics.

Fluorescent Film (Phosphor Layer)

Figure 4:
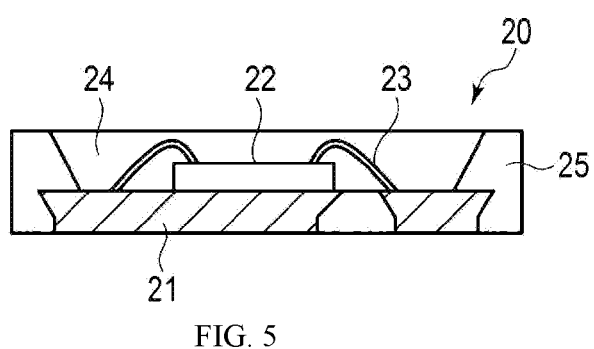
FIG. 4 is a diagram showing a cross section of an LED module.

A region around the LED chip on the substrate may be directly or indirectly covered with a phosphor layer. Another example of an LED module is presented in FIG. 4. An LED module 20 includes, for example, an electrode 21 made of a metallic conductor, an LED chip 22 formed on the electrode 21, a bonding interconnection 23 electrically connecting the electrode 21 and the LED chip 22, a phosphor layer 24 formed to directly cover the LED chip 22 on the electrode 21, and a resin mold 25 surrounding the phosphor layer 24.

Figure 5:
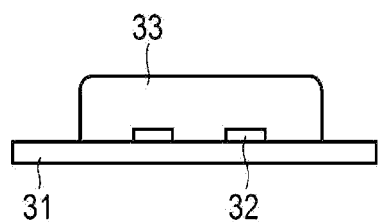
FIG. 5 is a cross-sectional view showing a phosphor layer covering a periphery of a plurality of LED chips.
Figure 6:
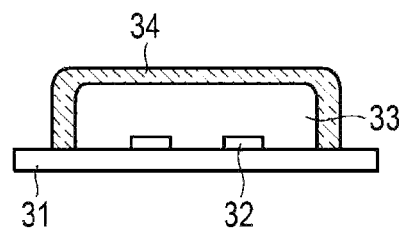
FIG. 6 is a cross-sectional view showing a relationship between a phosphor layer covering a plurality of LED chips and a transparent resin layer.

The resin mold 25 may also serve as a reflection member. Examples of arrangement of the phosphor layer are shown in FIGS. 5 through 8. In the LED module illustrated in FIGS. 5 through 8, a plurality of LED chips 32 are arranged in a linear shape on a substrate 31. As shown in FIG. 5, the phosphor layer 33 may be formed directly on a surface of the LED chip 32 on the substrate 31. As shown in FIG. 6, after a periphery of the LED chip 32 is covered with the phosphor layer 33, a periphery of the phosphor layer 33 may be coated with a transparent resin layer 34. In this case, the transparent resin layer may serve to protect the phosphor layer from the outside. In addition, the phosphor layer and the transparent resin layer of the present disclosure may be formed of a same base material, but may be formed of different materials if necessary. As such, when formed with different materials, total reflection may occur on an interface between the phosphor layer and the transparent resin layer depending on a difference in refractive index of each material. To prevent this, the interface between the phosphor layer and the transparent resin layer may be formed as a curved surface (see FIG. 51).

Figure 51:
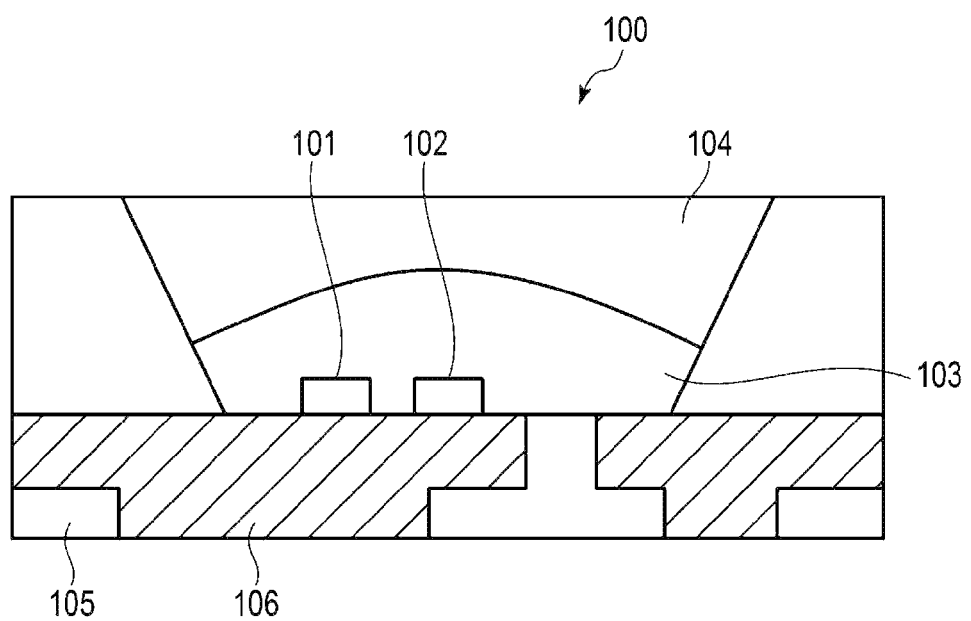
FIG. 51 is a schematic cross-sectional view illustrating a light emitting device according to an embodiment of the present disclosure.

An LED device 100 of FIG. 51 may be a package or module. The LED device 100 of FIG. 51 includes two leads 106 disposed far apart from each other, at least two LED chips 101 and 102 disposed on at least one of the leads 106, and a molding member 105 for securing the leads 106, and a cavity for exposing at least a portion of the lead and the LED chip may be formed in the molding member. In addition, a phosphor layer 103 and a transparent resin layer 104 that cover the lead 106 and the LED chip exposed in the cavity are included, and an order of the phosphor layer 103 and the transparent resin layer 104 may be changed as necessary. The phosphor layer 103 and the transparent resin layer 104 may be made of a same resin material, or may be made of different materials. When the phosphor layer 103 and the transparent resin layer 104 are made of different materials, luminous efficiency may be improved by forming an interface between the phosphor layer 103 and the transparent resin layer 104 in a curved shape to reduce total reflection on the interface. In addition, although the phosphor layer 103 in FIG. 51 is described as a single layer, it may also be formed as a plurality of layers. For example, after the phosphor layer 103 is formed in two or more layers, another phosphor may be disposed as each phosphor layer. In this case, reliability may be improved by disposing a phosphor having a relatively weak thermal degradation characteristic relatively far away from the chip.

Figure 7:
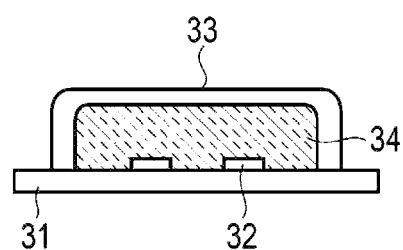
FIG. 7 is a cross-sectional view showing a relationship between a fluorescent film covering a plurality of LED chips and a transparent resin layer.
Figure 8:
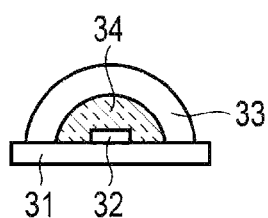
FIG. 8 is a cross-sectional view showing the relationship between a fluorescent film covering a single LED chip and a transparent resin layer.

Moreover, as shown in FIG. 7, after the surface of the LED chip 32 is covered with the transparent resin layer 34, an entire surface of the transparent resin layer 34 may be covered with the phosphor layer 33. Usually, there is a possibility that the phosphor may be deteriorated due to heat generated from the LED chip, and this may be prevented by covering the phosphor layer on the transparent resin layer in this way. Furthermore, in FIGS. 5 through 7, a plurality of LED chips is shown as being covered with a single phosphor layer or a transparent resin layer, but as shown in FIG. 8, a single LED chip 32 may be covered with a single transparent resin layer 34. In addition, with respect to FIG. 8, the LED chip 32 may be directly covered with a single phosphor layer 33 instead of the single transparent resin layer 34.

Moreover, as an application example, a periphery of a single LED chip or a plurality of LED chips may be covered with a transparent resin layer, a phosphor layer may be formed on an outer side thereof, and a transparent resin layer may be formed on a further outer side thereof, and thus it may be a stacked structure.

With respect to the various film configurations described above, the purpose of forming the transparent resin layer is to equalize the light emission intensity. When the plurality of LED chips is arranged in a certain pattern, positions where LED chips exist and positions where LED chips do not exist coexist on the substrate. When the periphery of the LED chip with such a pattern is covered with a phosphor layer, since the light emission intensity is strong in a portion where the LED chip exists, and the light emission intensity is weak in a portion where the LED chip does not exist, uniform light emission over an entire phosphor layer cannot be obtained. At this time, when the transparent resin layer is formed on an inner surface or outer surface of the phosphor layer, uniform light may be easily obtained over an entire layer. This is because, when the transparent resin layer is formed on the inner surface of the phosphor layer, primary light from the LED is scattered within the transparent resin layer. Meanwhile, when the transparent resin layer is formed on the outer surface of the phosphor layer, secondary light from the phosphor is scattered within the transparent resin layer. In addition, a same effect may be achieved even when the number of LED chips is one rather than multiple. Although a general shape of the LED chip is a rectangular parallelepiped, an emission intensity of light emitted from each surface of the rectangular parallelepiped is not same, and an emission intensity distribution is produced depending on an emission direction. Therefore, when the transparent resin layer is formed on the inner or outer surface of the phosphor layer covering the periphery of the LED chip, it is possible to achieve uniform emission intensity as in a case of multiple LED chips.

In addition, the transparent resin layer may be prepared for a purpose of not only improving the luminance characteristics as described above, but also protecting a fluorescent film or the like. For this purpose, it may be formed on an outer surface of the fluorescent film to physically and chemically protect the fluorescent film.

In addition, using the transparent resin layer as a protection film is not limited to protecting the fluorescent film. After undergoing a process of electrically connecting the electrodes and interconnection patterns, a transparent resin film is coated on an entire surface of the LED module, and it may also be used as a protection film.

The above transparent resin film may be formed only of resin, but may also contain a small amount of an inorganic compound inside the resin layer. In particular, when the transparent resin film is formed for the purpose of uniform emission intensity, by containing fine inorganic compound powder in the resin layer, light scattering effect by inorganic fine particles may be obtained, and thus, uniformity may be further achieved. Examples of inorganic material powder to be contained in the resin layer include silica powder such as silicate nanoparticles (fumed silica) or precipitated silica (wet silica), alumina powder such as alumina oxide or pulverized alumina, cerium oxide, zirconium oxide powder, and titanium oxide powder, and metal oxide powders such as barium titanate powder. A kind of inorganic material to be used may be made into 1 type, or 2 or more types. Among these, silica powder and alumina powder are preferable as inorganic compound powders to be contained in the transparent resin layer because they are inexpensive and can be easily reduced to fine particles. In particular, silicate nanoparticles and aluminum oxide are suitable because each of them is easy to obtain spherical ultrafine particles.

When a particle shape is spherical, light scattered from a particle surface is scattered uniformly in all directions, but when the particles are, for example, flat, the particles tend to line up in a certain direction within the transparent resin layer, and thus, there is a risk that light and shade may occur in directions of scattered light.

In addition, a maximum particle diameter of the inorganic material powder is preferably ¼ or less of a wavelength of light passing through the transparent resin layer. When an inorganic compound powder with a maximum particle diameter of ¼ or less of the wavelength of light is used, since transmitted light is appropriately scattered, an intensity of light emitted from the light source is uniformed, and a distribution of light may be improved. When the maximum particle diameter exceeds ¼ of the wavelength of light, a probability that light emitted from the LED or phosphor is reflected by the fine powder of the inorganic material and returned to the inside of the light source (on the LED chip side) increases. A lower limit of the maximum particle diameter of the inorganic material powder is not particularly limited in terms of the scattering effect, but it is difficult to obtain extremely fine particles industrially, and also in terms of handling the powder, particles larger than several nanometers are preferable, more preferably, particles of tens of nanometers or more.

It is preferable to contain the inorganic compound powder as described above in a range of 0.1 mass % or more and 5 mass % or less in the transparent resin layer. When a content of inorganic compound powder in the transparent resin layer is less than 0.1% by mass, there is a risk that the light scattering effect by the inorganic compound powder may not be sufficiently obtained. Meanwhile, when the content of the inorganic compound powder exceeds 5% by mass, multiple scattering of light tends to occur, and there is a risk that light emitted to the outside of the light source decreases. It is more preferable that the content of the inorganic compound powder in the transparent resin layer is 1% by mass or more.

The phosphor layer may contain a transparent resin material. Meanwhile, the transparent resin layer may mainly contain a transparent resin material, but may also contain other components such as phosphor or inorganic material powder. As such a transparent resin material, any material may be used as long as it satisfies strength, heat resistance, and transparency, but it is specifically preferable to use silicone resin, epoxy resin, or the like. In addition, when the phosphor layer and the inorganic material powder are simultaneously contained in the phosphor layer, it is preferable that the phosphor is formed in a lower portion in the resin and the inorganic material powder is uniformly distributed throughout the resin. Accordingly, diffusion characteristics of wavelength-converted light by the phosphor may be further improved. In particular, in the present disclosure, when the transparent resin layer is used in combination with an ultraviolet light emitting LED, it is more preferable to use a silicone resin favorable in resistance to deterioration to ultraviolet light. Epoxy resins are weak to ultraviolet light deterioration, and when used for a long period of time, a material thereof may yellow and transparency may be impaired.

(Phosphor Material)

To obtain an emission spectrum shape that exerts the effect of the present disclosure, it is preferable to combine two or more, or three or more of blue phosphors, cyan phosphors, green phosphors, yellow phosphors and red phosphors, as phosphors to be combined with LEDs. In particular, when three or more and six or less phosphors are combined, a wavelength range of visible light may be filled with emissions of various phosphors, and white light with high color rendering may be obtained.

In the present disclosure, after adjusting the spectral shape while paying attention to the wavelength range that affects melanopic irradiance, target white emission with an overall emission spectrum shape may be obtained by arbitrarily mixing the phosphors to obtain white light having an arbitrary color temperature or an arbitrary deviation. It is preferable to use a phosphor that is excited by an LED with an emission peak wavelength of 360 nm or more to 470 nm or less and exhibits an emission peak in a range of 420 nm or more to 700 nm or less. In addition, it is preferable that the emission peak wavelengths of each of the phosphors are offset from one another by 150 nm or less, 10 nm or more and 100 nm or less, or 10 nm or more and 50 nm or less. That is, it is preferable that a distance between a certain peak wavelength and an adjacent peak wavelength is 150 nm or less, 10 nm or more and 100 nm or less, or 10 nm or more and 50 nm or less. It is preferable that the emission spectra of at least two types of phosphors constituting the mixture of phosphors satisfy this relationship. In addition, it is preferable that a full width at half maximum of the emission spectrum of at least one type of phosphor constituting the mixture of phosphors is as wide as 50 nm or more, and more preferably, 50 nm or more and 100 nm or less. By using phosphors that satisfy these conditions, the emission spectrum of each phosphor becomes more likely to overlap with the emission spectrum of another phosphor, and as an overlapping area between the respective emission spectra increases, a smoother spectral characteristic with a few irregularities may be obtained in a spectral curve of obtained mixed white light.

Moreover, by using a plurality of phosphors of which the emission spectra overlap one another, it is possible to suppress a change in emission color during continuous lighting for a long period of time. Among the phosphors used in the present disclosure, there are phosphors with a wide absorption band. Such phosphors are not only excited by ultraviolet light or purple light, but may also be simultaneously excited by blue light or green light to emit green or red light. In these phosphors, when the plurality of phosphors of which the emission spectra overlap one another, reabsorption or double excitation between the phosphors is likely to occur, and the change in emission color may be suppressed. For example, a green phosphor emits green light by being excited by ultraviolet or purple light emitted from the LED, as well as by absorbing emission from a blue phosphor that is excited by the LED and emits blue light. That is, the green phosphor may emit light by double excitation of the LED and the blue phosphor. In general, in an artificial white light source, white light is obtained by mixing a light emission of a plurality of red, green, and blue phosphors inside a device. When such a white light source is continuously turned on, a brightness of the phosphors generally decreases over time. In this case, if the brightness of each phosphor changes with time to a same extent, a chromaticity of white light that can be obtained does not change. However, among a plurality of types of phosphors, if a luminance deterioration rate of a specific type of phosphor differs from that of other various phosphors, in obtained white light, there may be an excess or deficiency in light emission of a specific component, resulting in a change in luminous colors obtained. However, when mutual absorption or double excitation occurs as in the present disclosure, the deterioration rate between phosphors is averaged, and thus, the decrease in luminance of only a specific phosphor may be suppressed, resulting in a decrease in a chromaticity change of white light that can be obtained.

Moreover, with respect to a specific phosphor, it can be easily confirmed by measuring an excitation spectrum or emission spectrum of the phosphor by which wavelength it is excited and at which wavelength of light it emits. Therefore, by measuring the emission spectrum characteristics in advance and then selecting a combination of phosphors to be used, the chromaticity change during continuous lighting may be reduced as much as possible. By using the above effect, the white light source of the present disclosure may have a magnitude of the chromaticity change of less than 0.010 between an initial stage of lighting of the white light source using a CIE chromaticity diagram and after continuous lighting for 6000 hours. As for a method of measuring the magnitude of chromaticity change, according to JIS-Z-8518 (1998), chromaticity coordinates u' and v' at the initial lighting of the white light source and after continuous lighting of 6000 hours are measured, respectively. In this case, $\Delta u'$, $\Delta v'$, which is a difference in chromaticity coordinates, are calculated and the magnitude of the chromaticity change=$[(\Delta u')^2+(\Delta v')^2]^{1/2}$ can be obtained. The white light source of the present disclosure may reduce the magnitude of the chromaticity change to less than 0.010 or less than 0.009. When the magnitude of the chromaticity change is less than 0.010, it indicates a state in which there is hardly any color change from the initial lighting even after long-time use. Therefore, it is possible to maintain a stable ratio of α-opic irradiance over a long period of time.

Specific phosphors that can be used in the white light source system of the present disclosure are as follows. As blue phosphors, examples may include europium-activated alkaline earth phosphate phosphors (peak wavelength in a range of 430 nm or more to 470 nm or less) or europium-activated barium magnesium aluminate phosphors (peak wavelength in a range of 450 nm or more to 460 nm or less). Further, as cyan phosphors, examples may include europium, manganese-activated barium magnesium aluminate phosphor (peak wavelength in a range of 510 nm or more to 520 nm or less), europium-activated alkaline earth phosphate phosphor (peak wavelength in a range of 470 nm or more to 500 nm or less), or, europium-activated strontium aluminate phosphor (peak wavelength in a range of 480 nm or more to 500 nm or less). Examples of green phosphors may include europium-activated orthosilicate phosphor (peak wavelength in a range of 520 nm or more to 550 nm or less), cerium-activated rare earth aluminum garnet phosphor (peak wavelength in a range of 520 nm or more to 550 nm or less), europium-activated strontium sialon phosphor (peak wavelength in a range of 510 nm or more to 540 nm or less, or europium-activated R sialon phosphor (peak wavelength in a range of 535 nm or more to 545 nm or less). Furthermore, examples of yellow phosphors may include europium-activated orthosilicate phosphor (peak wavelength in a range of 550 nm or more to 580 nm or less), or cerium-activated rare earth aluminum garnet phosphor (wavelength in a range of 550 nm or more to 580 nm or less). In addition, examples of red phosphors may include europium-activated strontium sialon phosphor (peak wavelength in a range of 600 nm or more to 630 nm or less), europium-activated calcium nitrido aluminum silicate phosphor (emission peak wavelength in a range of 610 nm or more to 650 nm or less), europium-activated calcium nitrido aluminum silicate phosphor (peak wavelength in a range of 620 nm or more to 660 nm or less), europium-activated calcium oxonittrido aluminum silicate phosphor (peak wavelength in a range of 620 nm or more to 660 nm or less), or manganese-activated magnesium fluoro germanate phosphor (peak wavelength in a range of 640 nm or more to 660 nm or less).

Figure 9:
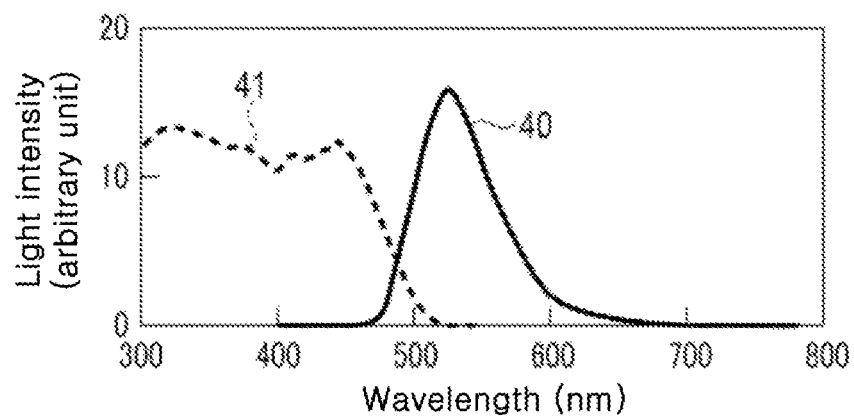
FIG. 9 is a diagram showing an excitation spectrum and an emission spectrum of a green phosphor used in the present disclosure.

FIG. 9 is a graph showing luminance characteristics of a green light-emitting europium-activated orthosilicate phosphor (a lateral axis indicates wavelengths (nm) and a vertical axis indicates light intensities (arbitrary unit)), which shows an emission spectrum 40 with a peak at 527 nm and an excitation spectrum 41 corresponding to an emission with the peak wavelength of 527 nm. As can be seen in FIG. 9, a longer wavelength end of the excitation spectrum 41 of this phosphor extends to about 525 nm, and it can be seen that green light is emitted when stimulated by ultraviolet light or purple light, furthermore, by blue light or cyan light. Similarly, FIG. 10 is a diagram showing an emission spectrum 42 and an excitation spectrum 43 of an europium-activated calcium nitrido aluminum silicate phosphor that emits red light.

Figure 10:
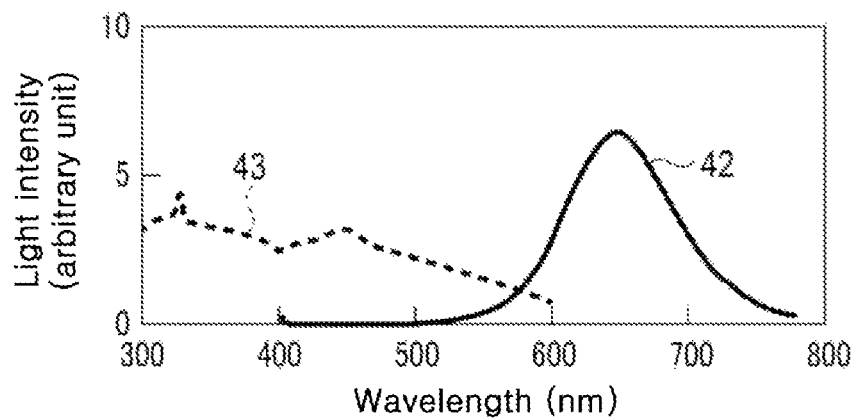
FIG. 10 is a diagram showing an excitation spectrum and an emission spectrum of a red phosphor used in the present disclosure.

A lateral axis of FIG. 10 indicates wavelengths (nm), and a vertical axis indicates light intensities (arbitrary unit). It can be seen that the excitation spectrum 43 of this phosphor spreads from a ultraviolet region to a yellow region and is excited by ultraviolet light, purple light, further blue light, green light, and even yellow light to emit red light. When the above two types of phosphors are combined with a purple LED and a blue phosphor to form a white light source, the blue phosphor is excited by the LED, the green phosphor is excited by the LED and the blue phosphor, and the red phosphor is excited by the LED and the blue phosphor and the green phosphor, and thus, reabsorption and multiple excitations between the phosphors occur.

In such a light source, even if only the blue phosphor significantly deteriorates in luminance due to changes over time, the luminance change in blue light may also affect the luminance of the green phosphor and the red phosphor, and thus, an overall luminance change may be averaged, resulting in obtaining a suppressing effect on the chromaticity change of white light.

Table 1 show a collection of data of emission peak wavelengths and full widths at half maximum with respect to emission spectra of phosphors used in the present disclosure. Numerical values in the table represent full widths at half maximum of the emission spectra corresponding to main peaks with respect to the emission spectra of each of the phosphors as representative values. As can be seen in Table 1, although there are some exceptions, the full widths at half maximum of most phosphors are 50 nm or more, and thus, if phosphors used are appropriately selected, it is possible to construct a white light source with a combination of all phosphors having a full width at half maximum of 50 nm or more.

TABLE 1

| Luminous color | Phosphor composition | Peak wavelength (nm) | full width at half maximum (nm) |
|---|---|---|---|
| blue | Europium Activated Alkaline Earth Phosphate Phosphor | 430~470 | 50 |
| blue | Europium Activated Barium Magnesium Aluminate Phosphor | 450~460 | 55 |

TABLE 1-continued

| Luminous color | Phosphor composition | Peak wavelength (nm) | full width at half maximum (nm) |
|---|---|---|---|
| turquoise | Europium Activated Alkaline Earth Phosphate Phosphor | 470~500 | 72 |
| turquoise | Europium, Manganese Activated Barium Magnesium Aluminate Phosphor | 510~520 | 12 |
| green | Europium Activated Orthosilicate Phosphor | 520~550 | 65 |
| green | Cerium-Activated Rare Earth Aluminum Garnet Phosphor (LuAG) | 520~550 | 99 |
| green | Europium Activated Strontium Sialon Phosphor | 510~540 | 60 |
| yellow | Europium Activated Orthosilicate Phosphor | 550~580 | 85 |
| yellow | Cerium Activated Rare Earth Aluminum Garnet Phosphor | 550~580 | 110 |
| red | Europium Activated Strontium Sialon Phosphor | 600~630 | 110 |
| red | Europium Activated Calcium Nitrido Aluminum Silicate Phosphor (SCASN) | 610~650 | 74 |
| red | Europium Activated Calcium Oxonitrido Aluminum Silicate Phosphor (CASON) | 620~660 | 128 |
| red | Europium Activated Calcium Nitrido Aluminum Silicate Phosphor (CASN) | 620~660 | 90 |
| red | Manganese Activated Magnesium Fluoro Germanate Phosphor | 640~660 | 33 |

In the table, what is written in a parenthesis of a phosphor composition is an abbreviation that combines a first letter of a chemical composition in English. It is assigned to distinguish compounds that are easily confused because they are similar.

(Luminescence Characteristics of a White Light Source).
Basic Design of White Light Source,
A member configuration and luminance characteristics of the white light source are, for example, as follows.

Figure 11:
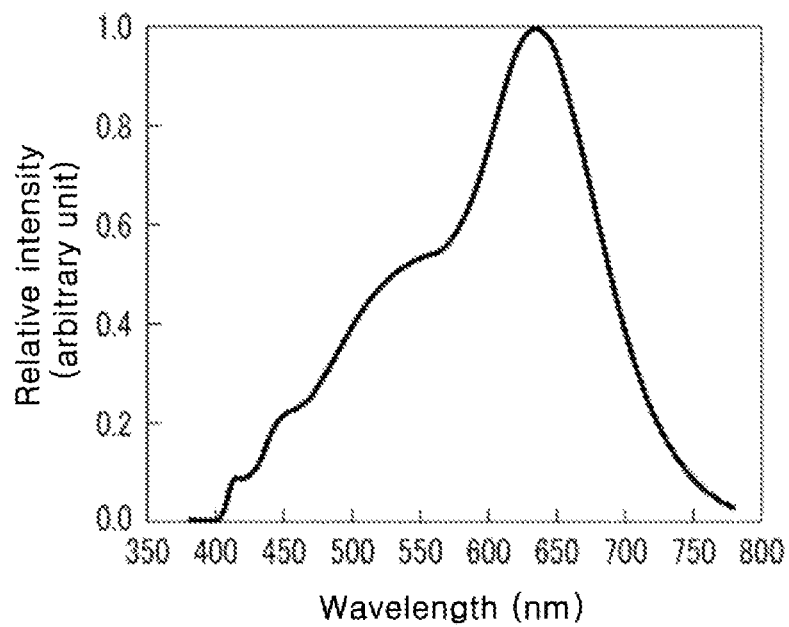
FIG. 11 is a diagram showing an emission spectrum of a white light source according to an embodiment of the present disclosure.

In a purple-light emitting LED with an emission peak at 410 nm, a total of five types of phosphors, including europium-activated alkaline earth phosphate phosphor as a blue phosphor, europium-activated alkaline earth phosphate phosphor as a cyan phosphor, europium-activated orthosilicate phosphor as a yellow phosphor, cerium-activated rare earth aluminum garnet phosphor as a yellow phosphor, and europium-activated alkaline earth nitrido aluminum silicate phosphor as a red phosphor are mixed at a weight ratio of 35:30:18:8:9, respectively, to create a white light source. An emission spectral shape of this light source is as shown in FIG. 11. A lateral axis of FIG. 11 indicates wavelengths (nm), and a vertical axis indicates relative intensities (arbitrary unit). In addition, a relative color temperature of the light source was 2900K+0.000 duv. Moreover, as color rendering characteristics of this light source, a high numerical value is shown as in Table 2 below, and when used as a light source, it was found to be a favorable white light capable of reproducing a color of an object in a natural form.

TABLE 2

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 97 | 96 | 98 | 96 | 94 | 96 | 96 | 99 | 99 | 97 | 98 | 90 | 95 | 96 | 97 | 98 |

(α-opic irradiance of white light source) A most important characteristic of the white light source of the present disclosure is α-opic irradiance. It is thought that by maintaining the α-opic irradiance at an appropriate level, it is possible to obtain illumination light that has an appropriate effect on a person's daily rhythm and others.

Hereinafter, a meaning of a opic irradiance and how to obtain a calculated value will be described.

There are five types of photoreceptor cells in humans, in more detail, they are rod cells, three types of cones (S-cones, M-cones, L-cones), and ipRGCs. There are approximately 100 million rod cells in the periphery of the retina of the eye, accounting for 95% of photoreceptor cells. The rod cells work in weak light of less than about 1 lux, nerve activity via rod cells is transmitted to the cerebral visual area, and involved in sensing the intensity of light, but not in sensing color. The cones exist near the fovea of the retina and work in a normal light environment (brightness when people engage in daily activities), and there are three types depending on the wavelength range in which they act. There are three types: L-cones, which act at the longest wavelengths (around orange), M-cones, which act at medium wavelengths (around yellow green), and S-cones, which act at the shortest wavelengths (around blue). Each of the cone cells contains a protein that responds best to a specific range of wavelengths (the iris), so that they receive visible light, and the signal passes through the optic nerve to the visual association area of the cerebrum, where colors can be perceived by analyzing the relative ratio or location of information from the three cones.

The remaining photoreceptor cell is a new photoreceptor different from the cones or rods, which is called ipRGC. The ipRGC has a protozoan called melanopsin, and is involved in non-visual functions that people are not conscious of, such as pupil reflexes and light synchronization of daily rhythms. When light is received by the ipRGC, the optical signal is transmitted directly to the suprachiasmatic nucleus, which has the function of an internal clock that controls the circadian rhythm, such as sleep/awakening, and the concentration of hormone (melatonin), so the ipRGC is deeply involved in the daily rhythm.

As mentioned above, light is strongly related to people's health through sleep and others, and light is received into the body through photoreceptor cells, and among the five types of photoreceptor cells, light input through a pathway that uses melanopsin as a starting material, that is, light stimulation to the ipRGC, is deeply related to human sleep. Therefore, in the present disclosure, by examining a relationship between an amount of light stimulation for photoreceptor cells, including the ipRGC, and human sleep, it was noted that a method for developing and using an illumination light source effective for human sleep and health promotion can be specified. To achieve this goal, it is necessary to know an amount of light stimulation introduced into photoreceptors, and a following method was found as a calculation method.

(Equation 4)

$$\alpha\text{-Opic irradiance} = \int(\text{spectrum of light source})*(\text{action curve of each eye cell})*d\lambda \quad (4)$$

In order for a person to sense light, light needs to reach the retina of the eye and irradiate the photoreceptor cells. Acquisition of light intensity information is performed based on detecting a stimulation amount for each photoreceptor cell corresponding to an intensity of light. The stimulation amount of each photoreceptor cell may be calculated as a sum of a product of a spectrum of light irradiated on the retina for each wavelength and a weight-function unique to each photoreceptor cell, that is, a spectral sensitivity curve, as shown in the Equation (4).

Figure 12:
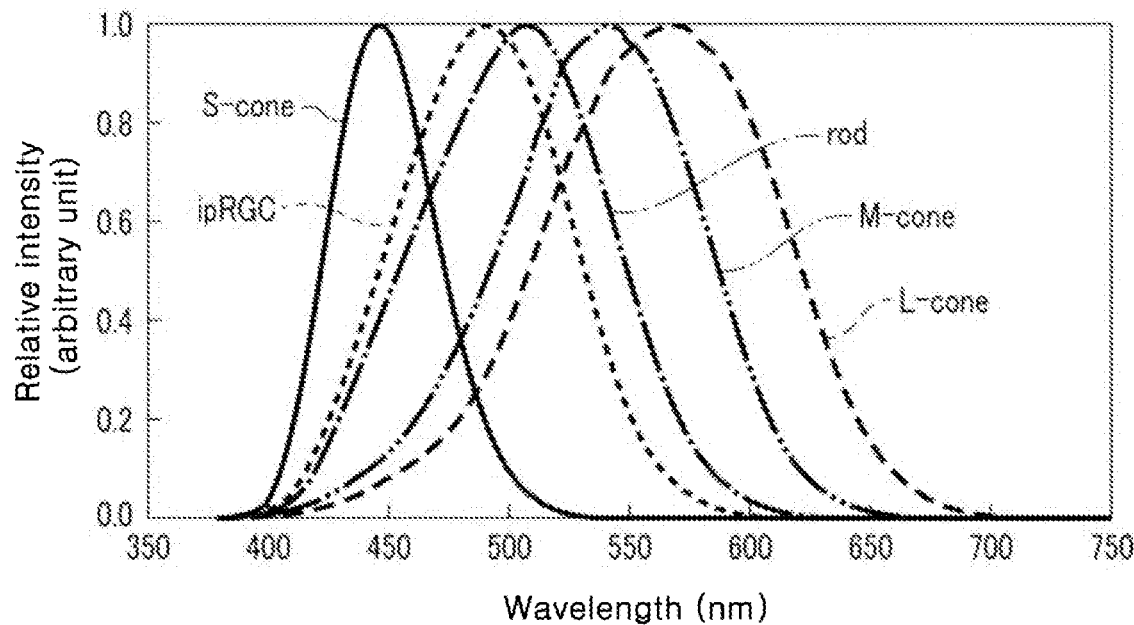
FIG. 12 is a diagram showing action curves for five types of photoreceptor cells.

In the above Equation (4), action curves of each photoreceptor cell are action curves for S-cone, M-cone, L-cone, rod, and ipRGC, as shown in FIG. 12. The action curves for the five types of photoreceptor cells shown in FIG. 12 conform to the provisions of the International Commission on Illumination (CIE) standard CIES026/E:2018, respectively. In addition, a lateral axis of FIG. 12 indicates wavelengths (nm), and a vertical axis indicates relative intensities (arbitrary unit). Indications of S-cone, M-cone, L-cone, rod, and ipRGC in FIG. 12 correspond to the respective action curves for the S-cone, M-cone, L-cone, rod, and ipRGC. Therefore, five types of values may be obtained as $\alpha$-opic irradiance ($\alpha$-opic-irradiance, unit: $W \cdot m^{-2}$). Specifically, when calculated using the action curve of the S-cone, S-cone-opic irradiance may be obtained, and similarly, in a case of the M-cone, M-cone opic irradiance, in a case of the L-cone, L-cone opic irradiance, in a case of the rod, Rhodopic-irradiance, and in a case of the ipRGC, Melanopic-irradiance may be obtained.

According to the above calculation formula, when a light source having a certain emission spectrum is used with a certain intensity, it is possible to quantitatively grasp an intensity of stimulation to the photoreceptor cells of the eye. For example, in a case that a white light source for lighting is prepared, if a spectral distribution of the light source is known, melanopic irradiance thereof may be obtained using the ipRGC action curve and the above calculation formula, and a daily rhythm management by controlling the melanopic irradiance is expected to be possible.

In the present disclosure, first, as a reference value for managing the intensity of melanopic irradiance, it was decided to introduce a ratio determined below. Specifically, it is a ratio between the three parties that combine M-cone-opic-irradiance for M-cone and L-cone-opic-irradiance for L-cone, in addition to the melanopic irradiance.

This ratio is expressed by (1) as follows.

$$\text{Melanopic irradiance}/(L\text{-cone opic irradiance}+M\text{-cone opic irradiance}) \quad (1)$$

For a denominator of the Equation (1), any of the five types of $\alpha$-opic irradiance except melanopic irradiance may be used, but in the present disclosure, two types of $\alpha$-opic irradiance and M-cone opic irradiance were used. The reason is that a reference value corresponding to a sensitivity of the human eye may be set by using a sum of both stimulation amounts of the L-cone and M-cone as the denominator. That is, when emission spectra of two types of light sources are compared using this ratio, the light sources of a same brightness when viewed by the human eye can be compared with numerical values of melanopic irradiance.

With the calculation method is clarified by the above, a ratio of an $\alpha$-opic irradiance of a specific white light source is then obtained. A calculation target is a white light source having the emission spectrum shown in FIG. 11. The calculation method may be calculated using Equation (5) below, for example, taking the melanopic irradiance as an example.

(Equation 5)

$$\text{Melanopic irradiance} = \text{Remission spectrum of white light source}*(\text{action curve of ipRGC})*d\lambda \quad (5)$$

In addition, the $\alpha$-opic irradiances of other photoreceptor cells may be calculated in a same manner as above using the five types of action curves shown in FIG. 12 pointed out earlier, to obtain the five types of spectrum curves shown in the figure below.

Figure 13:
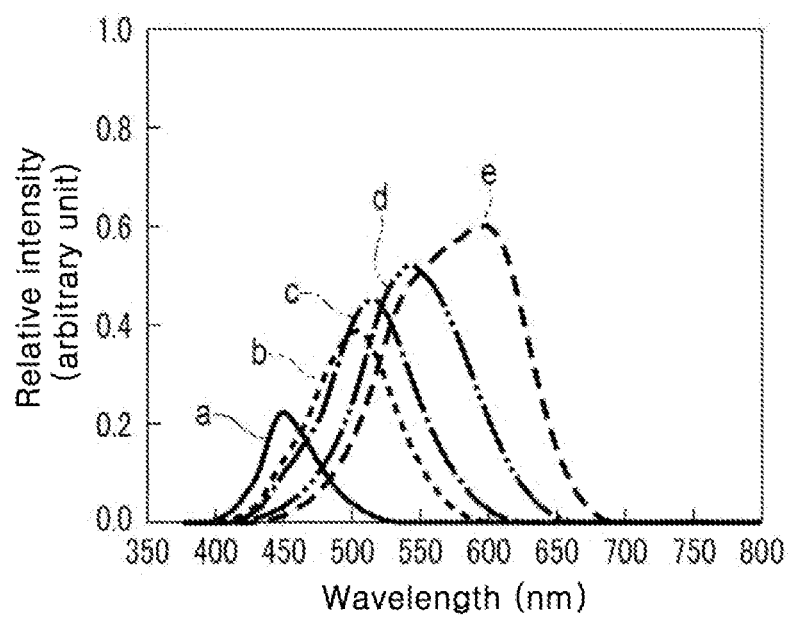
FIG. 13 is a diagram showing a spectral curve of α-opic irradiance of a white light source.

The five types of curves in FIG. 13 are: a curve a corresponds to the S-cone opic irradiance, a curve b corresponds to the melanopic irradiance, a curve c corresponds to the rhodopic irradiance, a curve d corresponds to the M-cone opic irradiance, and a curve e corresponds to the L-cone opic irradiance. If the ratio (melanopic irradiance/(L-cone opic irradiance+M-cone opic irradiance)) is calculated using three kinds of curves among the above five types, Equation (6) can be obtained in the following procedure.

$$\text{Melanopic irradiance}/(L\text{-cone opic irradiance}+M\text{-cone opic irradiance}) = (\text{Remission spectrum of white light source})*(\text{action curve of ipRGC})*d\lambda)/(\text{Remission spectrum of white light source})*(\text{action curve of } L \text{ cone})*d\lambda + (\text{emission spectrum of white light source})*(\text{action curve of } M \text{ cone})*d\lambda) = \text{area of spectrum curve } b/(\text{area of spectrum curve } e + \text{area of spectrum curve } d) = 24.8(\%) \quad (\text{Equation 6})$$

A value of 24.8 obtained above is a ratio of a opic irradiance to this white light source.

(Effect of $\alpha$-Opic Irradiance on Human Sleep)

Since the $\alpha$ opic irradiance obtained above may be evaluated for a degree of an amount of stimulation light that this white light source acts on the ipRGC by checking the calculated value, it is possible to quantitatively determine an extent to which the luminescence characteristics of the white light source affect a person's daily rhythm. To this end, we decided to examine light sources with various values of opic irradiance ratios to determine their relationship with human sleep.

For the light source to be sampled, for three types of white light sources with color temperatures of 2900K, 4000K, and 5000K, samples having three levels of $\alpha$-optic irradiance ratio were prepared within a range of an emission spectral shape of which the color rendering characteristic (Ra) represents a practical level. A design of the light source was same as that of the white light source shown above, and types of LEDs were used with same luminous characteristics, but to obtain characteristics at each level, types and ratios of phosphors to be used were appropriately changed. The luminescence characteristics of the obtained light source samples are summarized in Table 3 below.

TABLE 3

| Color temperature (K) | Light source No | Correlated color temperature | ratio(%) * | Color rendering (Ra) |
|---|---|---|---|---|
| 2900 | Spl 1 | 2910K + 0.001 duv | 19.9 | 95 |
|  | Spl 2 | 2900K + 0.000 duv | 24.8 | 97 |
|  | Spl 3 | 2910K + 0.001 duv | 29.1 | 87 |

TABLE 3-continued

| Color temperature (K) | Light source No | Correlated color temperature | ratio(%) * | Color rendering (Ra) |
|---|---|---|---|---|
| 4000 | Spl 4 | 4020K + 0.001 duv | 25.1 | 79 |
|  | Spl 5 | 3990K + 0.002 duv | 29.5 | 98 |
|  | Spl 6 | 3980K + 0.001 duv | 35.7 | 95 |
| 5000 | Spl 7 | 5020K + 0.002 duv | 30.9 | 73 |
|  | Spl 8 | 5000K + 0.000 duv | 35.1 | 95 |
|  | Spl 9 | 5030K + 0.001 duv | 39.5 | 99 |

*is melanopic irradiance/(L-cone opic irradiance + M-cone opic irradiance.

To determine effects of these white light sources on human sleep, 27 experimental participants helped. The experimental participants were 27 normal people in their 20s to 40s, divided into 9 groups of 3 each. A group classification was made as randomly as possible, taking into account the wishes of the experimental participants, regardless of gender or age. Conditions were divided into three categories: 8-13:00, 13:00-18:00, and 18-23 o'clock, and each group received indoor lighting under different conditions according to a time zone. A detailed lighting schedule is shown in Table 4 below. Color temperatures and illuminance in Table 4 represent color temperatures and illuminance of white light output from each of the white light sources and commercial fluorescent lamps used in each time zone. Survey items include collecting saliva from the experimental participants at 10 p.m. to analyze an amount of melatonin secreted in the saliva, while also conducting a survey on sleep situations every morning at 8 a.m. to receive responses regarding self-evaluation of each person's sleep state and whether and how often they awoke during sleep.

TABLE 4

| Group No | 8~13 o'clock 4000K, 400 lux | 13~18 o'clock 5000K, 500 lux | 18~23 o'clock 2900K, 300 lux |
|---|---|---|---|
| 1 | Commercial fluorescent lamp | commercial fluorescent lamp | White light source Spl 1 |
| 2 |  |  | White light source Spl 2 |
| 3 |  |  | White light source Spl 3 |
| 4 | White light source Spl 4 | commercial fluorescent lamp | commercial fluorescent lamp |
| 5 | White light source Spl 5 |  |  |
| 6 | White light source Spl 6 |  |  |
| 7 | commercial fluorescent lamp | White light source Spl 7 | commercial fluorescent lamp |
| 8 |  | White light source Spl 8 |  |
| 9 |  | White light source Spl 9 |  |

Figure 14A:
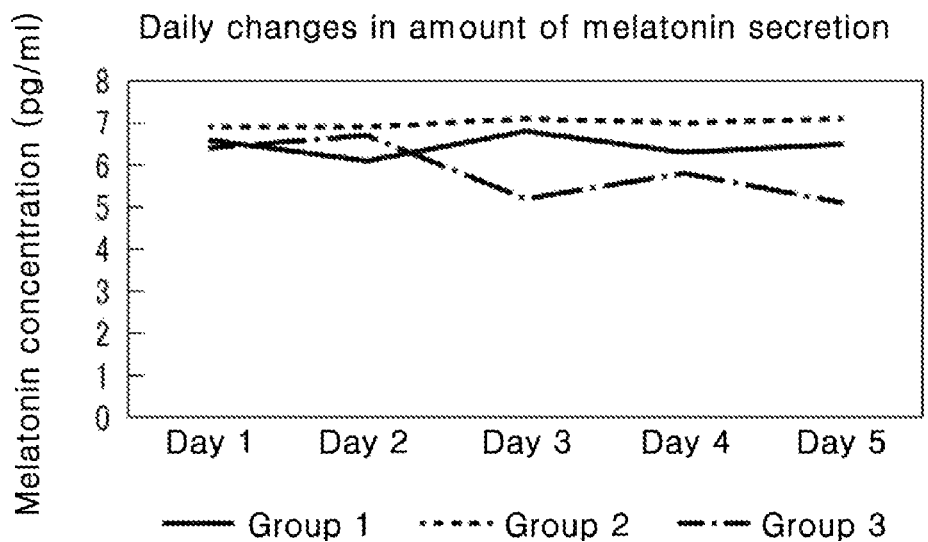
FIG. 14A is a graph showing daily changes in melatonin secretion amounts for Groups 1-3.
Figure 14B:
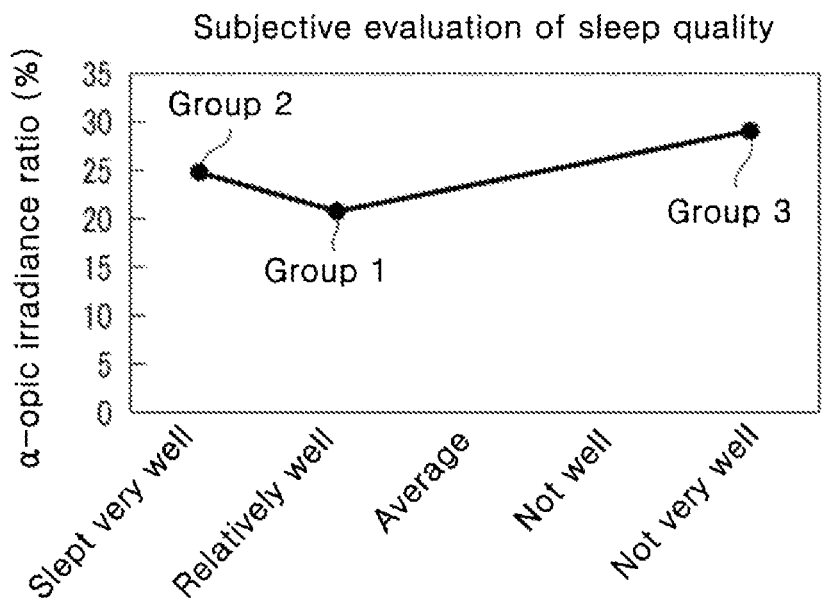
FIG. 14B is a graph showing relationships between subjective evaluations of sleep quality and α-opic irradiance ratios for Groups 1-3.
Figure 14C:
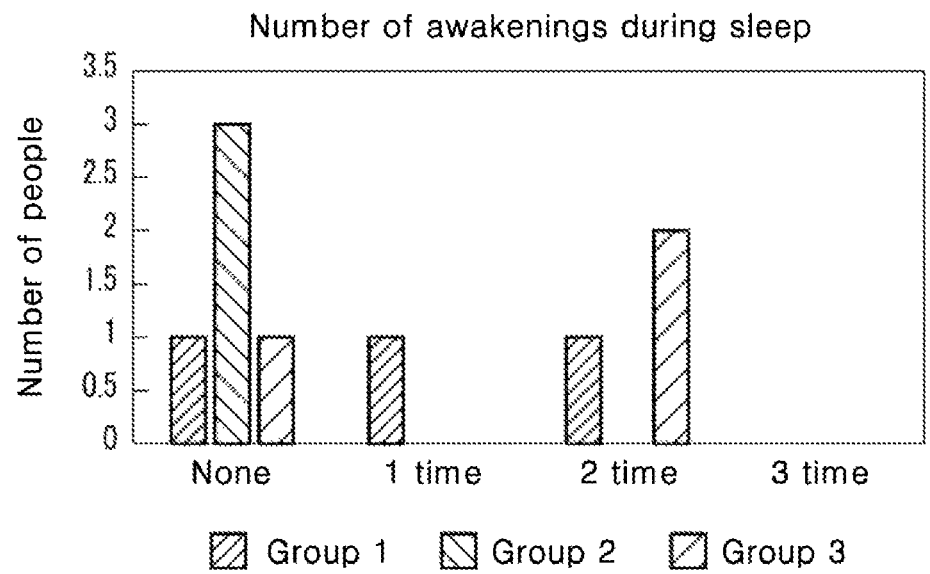
FIG. 14C is a graph showing the number of awakenings during sleep time for Groups 1-3.

A comparative analysis of the melatonin concentration analysis data in saliva, and questionnaire data was performed. In the comparison, to accurately evaluate the effects of differences in white light sources on the human body, groups with exactly same lighting conditions were compared on a daily basis to exclude a possibility of unnecessary factors affecting the analysis results. Evaluation results by dividing them into Groups 1 to 3, 4 to 6, and 7 to 9 are as follows. The results of the comparative evaluation of Groups 1 to 3 are as shown in FIGS. 14A, 14B and 14C. The table below shows a daily change in a melatonin secretion amount over 5 days relative to an average value of 3 group members. In addition, a subjective evaluation of sleep quality is not individual data, but results shown by 3 people over 5 days are collected as a representative value. Moreover, regarding the number of awakenings during sleep, a total number of awakenings experienced by each member over 5 days was counted for each member, and the number of awakenings was classified according to the number of experienced persons.

As a result of comparing a degree of influence on a person's sleep state, it was found that there is an optimal value among three levels of the α opic irradiance ratio. Evaluation results of Group 2 using a white light source Spl 2, of which the rate was 24.8 which showed a median value, was stable with a largest amount of melatonin secretion and a little daily change in the secretion amount. In addition, in the survey results, all answered that they slept well, and all answered that the number of awakenings during sleep was 0, showing a highest rating of Grade A, whereas Group 3, which used a white light source Spl 3, of which the rate was 29.1% which was a highest, had a lowest amount of melatonin secretion, and the change in secretion amount increased as the day went by.

Figure 15A:
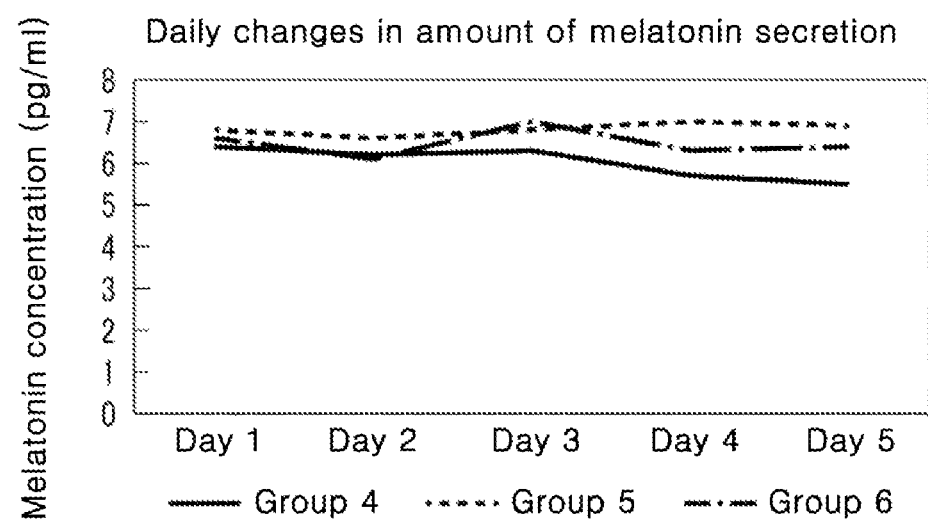
FIG. 15A is a graph showing daily changes in melatonin secretion amounts for Groups 4-6.
Figure 15B:
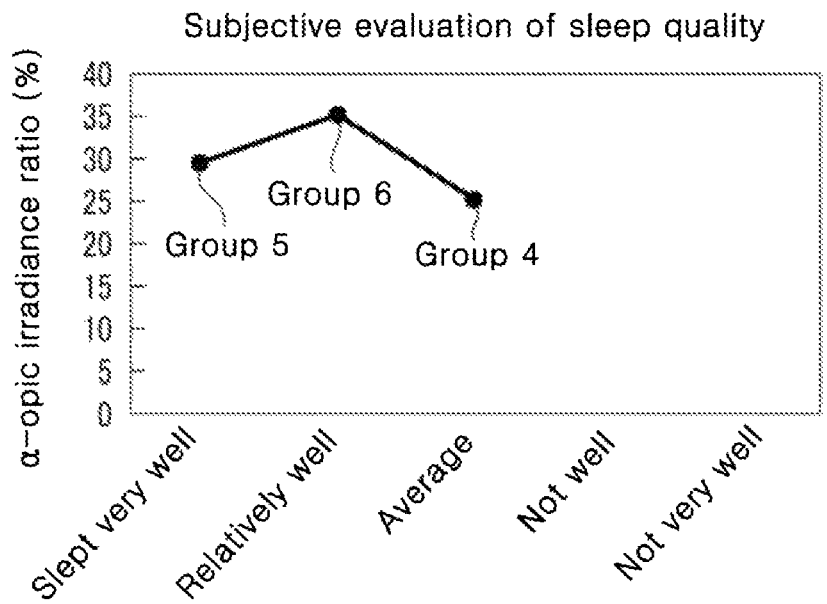
FIG. 15B is a graph showing a relationship between subjective evaluations of sleep quality and α-opic irradiance ratios for Group 4-6.
Figure 15C:
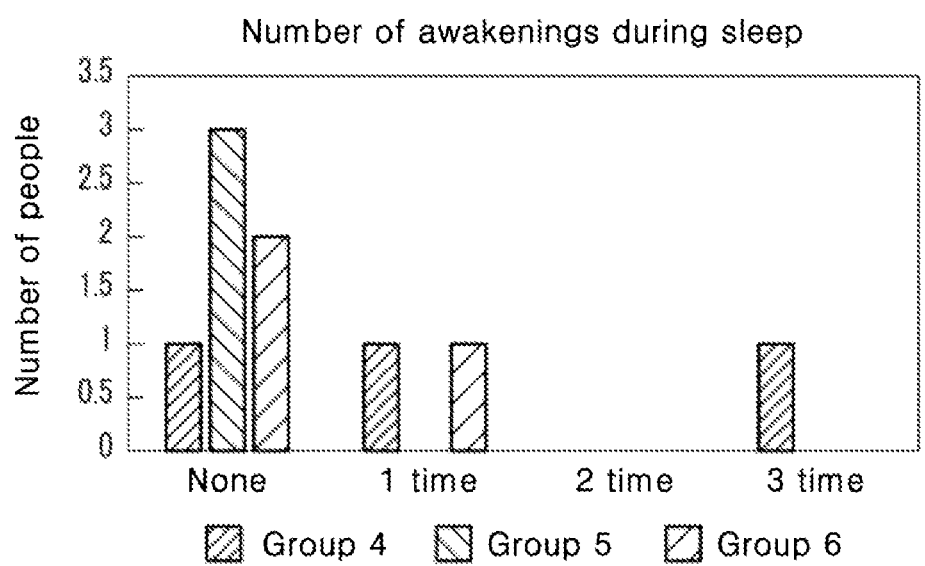
FIG. 15C is a graph showing the number of awakenings during sleep time for Groups 4-6.

Moreover, the survey results showed that the number of awakenings during sleep was a highest among the three groups, and in the sleep quality evaluation, they had a high tendency to evaluate that they did not sleep well, showing a lowest rating of Grade C among the three groups. In addition, Group 1, which used a white light source Spl 1, of which the rate was 19.9% which was a lowest, presented middle values in terms of melatonin secretion and sleep quality evaluation among the three groups and the evaluation was Grade B. The evaluation results of these three groups could be most clearly divided into three grades compared with the evaluation results of the other three groups. It is presumed that the melatonin secretion was disrupted in Group 3 where the ipRGC received excessive light stimulation before bedtime or Group 1 that received only light stimulation before bedtime, which adversely affected the quality of sleep, whereas Group 2 that received a most appropriate light stimulation had a best effect on the human body. The evaluation results of Groups 4 to 6 are shown in FIGS. 15A, 15B, and 15C.

The Groups 4 to 6 were able to obtain almost same results as those of the previous Groups 1 to 3, and among the three groups, Group 5, which used a white light source Spl 5, who showed a median amount of light stimulation of ipRGC, showed a best result, and the grade was A.

Meanwhile, Grade B was Group 6, which used a white light source Spl 6 with a largest amount of light stimulation, and Group 4, which used a white light source Spl 4 with a least amount of light stimulation, was Grade C. A grade ranking was reversed from that of the previous Groups 1-3. For Groups 4 to 6, the evaluation results were also divided into Grades A, B, and C, but data differences between Grades tended to be smaller than those for Groups 1 to 3.

Figure 16A:
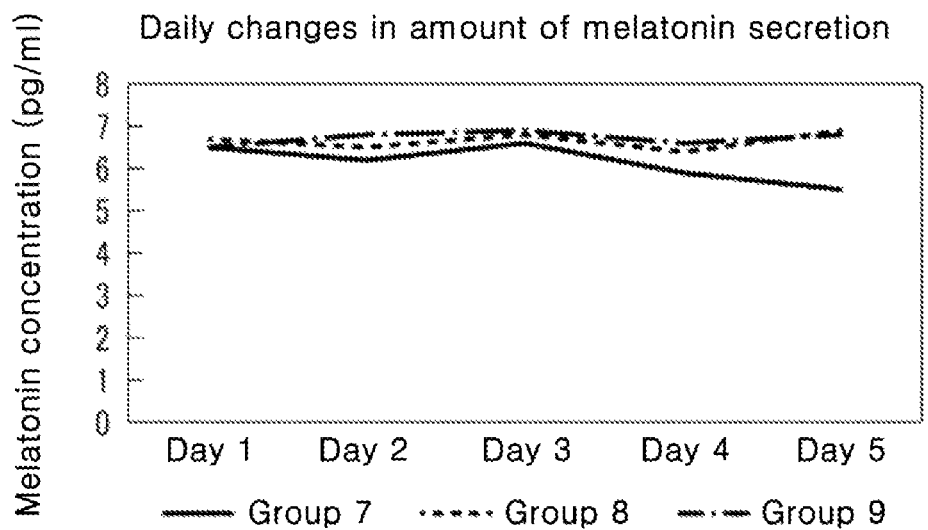
FIG. 16A is a graph showing daily changes in melatonin secretion amounts for Groups 7-9.
Figure 16B:
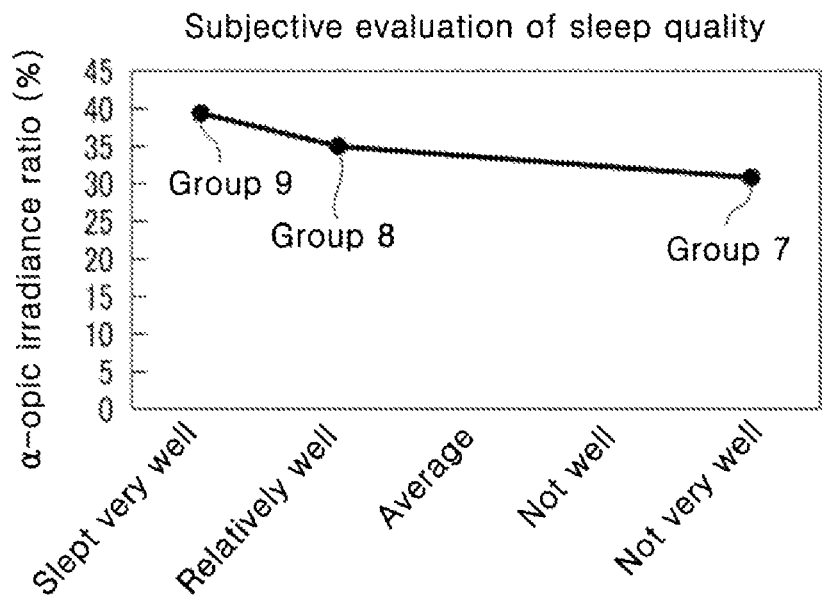
FIG. 16B is a graph showing relationships between subjective evaluations of sleep quality and α-opic irradiance ratios for Groups 7-9.
Figure 16C:
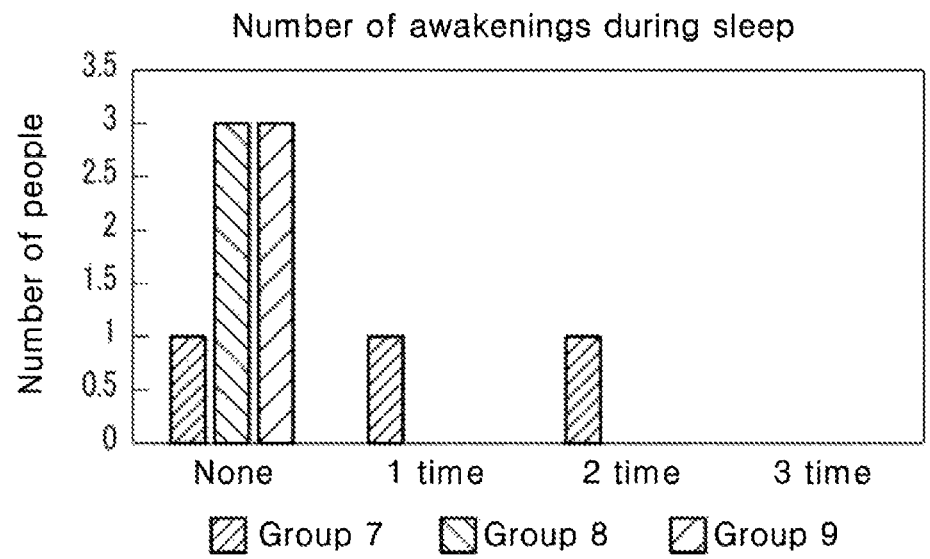
FIG. 16C is a graph showing the number of awakenings during sleep time for Groups 7-9.

Evaluation results of Groups 7 to 9 are shown in FIGS. 16A, 16B, and 16C. The evaluation results of these Groups are not divided into three categories of A, B, and C, but are divided into two groups. The Groups 8 and 9, which used white light sources Spl 8 and 9 with a large amount of light stimulation to the ipRGC, had a large amount of melatonin secretion and a stability of daily changes was generally stable although there were some changes, and sleep quality and the number of awakenings during sleep also showed good results, thereby being equivalent to Grade A. On the other hand, the Group 7, which used a white light source Spl 7 with a lowest amount of light stimulation, was worse than the other two Groups in terms of melatonin secretion amount, stability of daily changes, sleep quality, and the number of awakenings during sleep, and thus, only this group received Grade C.

Figure 17:
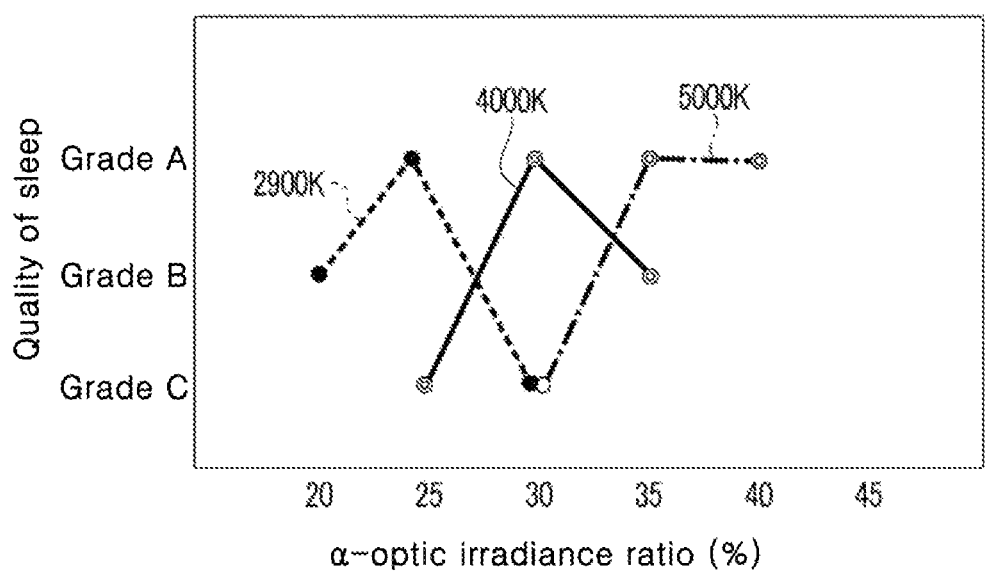
FIG. 17 is a diagram showing a relationship between an α-opic irradiance and sleep quality.
Figure 18:
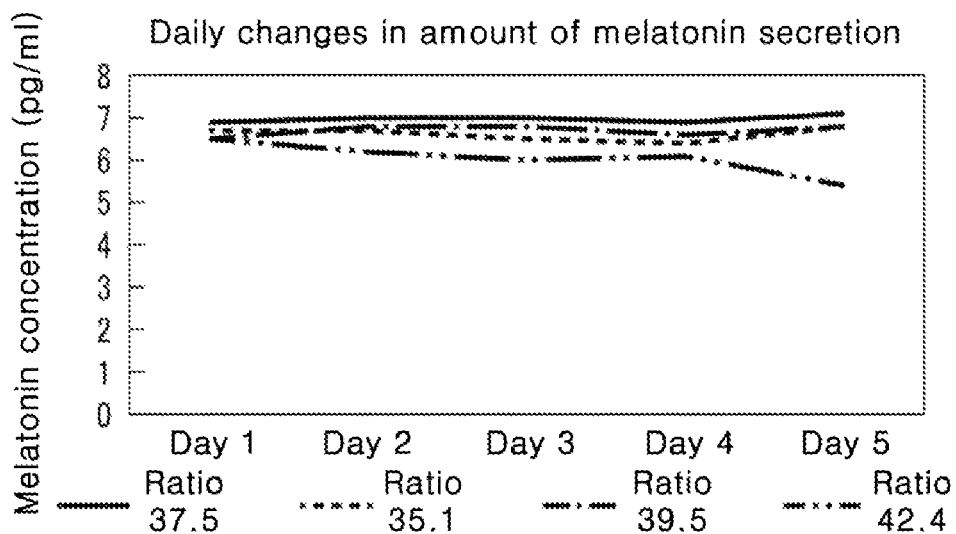
FIG. 18 is a diagram showing a relationship between a daily change in a melatonin secretion amount and an α-opic irradiance ratio.

As a result of the above three types of evaluations, a relationship between the α opic irradiance ratio value of the white light source to be used in the evaluation test and the rating data of the effect on human sleep is summarized in FIG. 17. For light sources of 2900K and 4000K, an optimal value of the ratio could be confirmed, but for a white light source of 5000K, an optimal value could not be clearly identified. From these results, it was unclear whether the optimal value existed but was not found, or whether the effect on sleep was saturated beyond a certain value, so we decided to conduct a retest to identify it. In the retest, in addition to the white light sources used last time with opic irradiance ratios of 35.1% and 39.5%, respectively, new light sources with the above ratios of 37.5% and 42.4% were added, and a melatonin secretion evaluation test was conducted using a same method as that of the last time. The results are as shown in FIG. 18. A melatonin secretion status of the experimental participants who received the same white light sources with the above ratios of 35.1% and 39.5% as those of the previous time (hereinafter referred to as the two types of reproductions) were at a level equivalent to Grade A, as the previous result was reproduced. Meanwhile, among additional white light sources, a light source receiver with the above ratio of 37.5% showed better results than the experimental participants who received the two types of light sources of two types of reproductions, and showed a superior effect than the two types of light sources of two types of reproductions in both the secretion amount and the stability of the secretion amount. Therefore, these three light sources all showed results corresponding to Grade A, but an optimal value of opic irradiance was found to be 37.5%, which is between 35.1% and 39.5%. In addition, in one of the additional light sources, participants of a light source with a highest ratio of 42.4% showed a small amount of melatonin secretion and had poor daily stability of secretion amount change, which was equivalent to Grade C. It is presumed that an amount of light stimulation to the ipRGC was excessive.

Figure 19A:
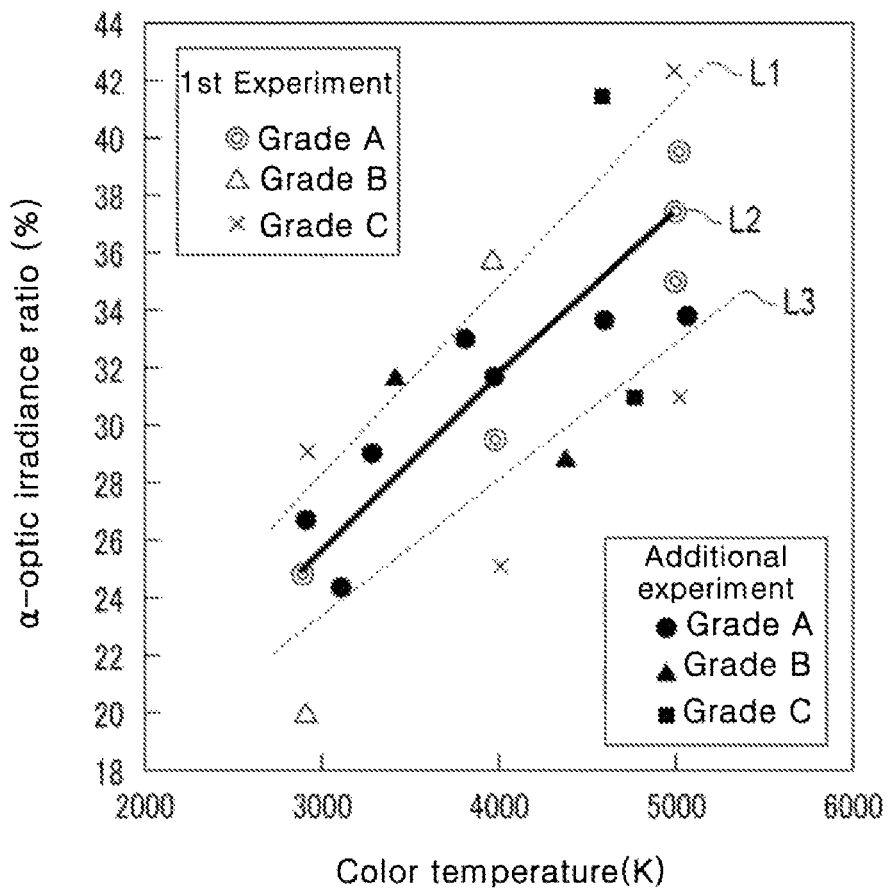
FIG. 19A is a diagram showing a range of α-opic irradiance ratios that provide favorable sleep quality.

However, from the above experimental results, it was found that an α opic irradiance ratio of a white light source has an optimal value for each color temperature as the effect on human sleep, and that there is a certain width in the optimal value from the retest data. Therefore, to understand the width of the optimal value in more detail, 11 new light source samples expected to belong to a core or boundary of the optimal value were prepared and an additional test was conducted in the same manner as that of the first time. Combined results of the first test and additional tests are shown in FIG. 19A. In the drawing, a mark indicated by the first test indicates the data of the two experiments described above, and a mark indicated by the additional test indicates data obtained as a result of an additional experiment. In the first test, Grade A is indicated by a double circle, Grade B is indicated by a black triangle, and Grade C is indicated by x.

In addition, Grade A of the additional test is indicated by a black circle, Grade B is indicated by a black triangle, and Grade C is indicated by a black square. From these results, it was found that a most preferable range for a white light source that provides a favorable sleeping effect to people is values on a straight line L2 in the drawing and values within a region enclosed by dotted lines L1 and L3 on both sides of the straight line L2. That is, the light source preferably has an α-opic irradiance ratio of about 22 to 27% when it is about 3000K, and an α-opic irradiance ratio of about 33 to 42% for a light source of about 5000K.

The optimal range of α-opic irradiance revealed by the present disclosure is a newly discovered range that is not described in previous inventions. It has been well known that blue light affects the quality of sleep. For example, in a case of using white light sources with different color temperatures, when you want to increase an intensity of blue light, you often use a white light source with a high color temperature, and when you want to suppress the intensity of blue light to low, you often use a white light source with a low color temperature. However, what is newly revealed through this test is only the amount of stimulation light due to blue light, and it is preferable to select white light with the optimal color temperature that matches a person's daily or life rhythm rather than to select the color temperature of the white light source to be used. And by using the light source with the optimal α opic irradiance among the selected color temperatures, the effect on the person's sleep may be made much better than before.

As mentioned above, although the preferable range of the present disclosure can be specified, managing it using the above ratio as a method for using a light source is inconvenient as an index for managing characteristics of general lighting. This is because it becomes necessary to use a white light source with a different ratio for each color temperature. Therefore, the present inventors and others clarified a method for normalizing the preferable range of the α-opic irradiance ratio as a method for using the light source of the present disclosure to the optimum value of each color temperature (a numerical value on the straight line L2 in FIG. 19A). Through standardization, white light sources with different color temperatures may be unified and managed. It was decided to use the optimal value of each color temperature for the ratio that serves as a standard for standardization. However, when a color rendering index (Ra) of the optimal value for each color temperature is confirmed, three points on the straight line L2 in FIG. 19A are 97, 98, and 99, of which the values are close to 100, and thus, a ratio of α-opic irradiance indicated by black body radiation at each color temperature where Ra is equivalent to 100 was taken as the standard value described above.

An emission spectrum distribution of black body radiation as the standard or the intensity of the melanopic irradiance may be obtained by the following procedure, as in the case of the white light source. First, various emission spectra with different color temperatures may be reproduced relatively easily using Equation (6) shown below. Wherein h is Planck's constant, k is Boltzmann's constant, c is the speed of light, and e is the bottom of the natural logarithm, since they are fixed at a constant value, when a color temperature T is determined, a spectral distribution $B(\lambda)$ corresponding to each wavelength $\lambda$ may be obtained.

(Equation 7)

$$B(\lambda) = (2hc^2/\lambda^5) * (1/e^{hc/\lambda kT} - 1) \tag{6}$$

Figure 20:
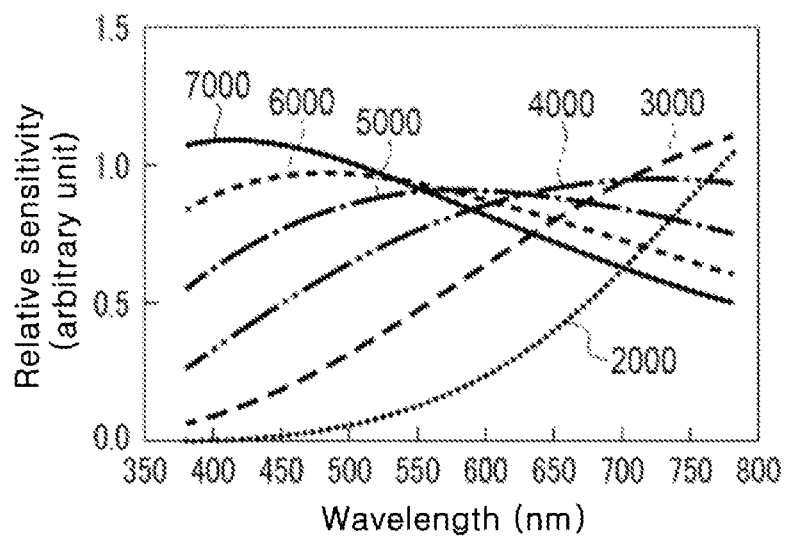
FIG. 20 is a diagram showing emission spectra of blackbody radiation with different color temperatures.

FIG. 20 is a diagram showing blackbody radiation spectra at color temperatures from 2000K to 7000K calculated using the Equation (6) above at intervals of 1000K. In the blackbody radiation spectrum at a lowest color temperature of 2000K, there is no emission peak in a visible light wavelength range, and as the wavelength becomes longer, an emission intensity also increases. Meanwhile, when the color temperature exceeds 4000K, a luminescence peak begins to appear in the visible light wavelength range, and as the color temperature increases, it can be seen that the emission peak wavelength is further shifted toward a shorter wavelength. Once the blackbody radiation spectrum for each color temperature can be calculated, an α-opic irradiance for each luminescence spectrum may then be calculated. For example, melanopic irradiance can be calculated using the following Equation (5A), as in the case of the white light source.

(Equation 8)

Melanopic irradiance=∫(spectrum of blackbody radiation)*(action curve of ipRGC)*$d\lambda$  (5A)

Figure 21A:
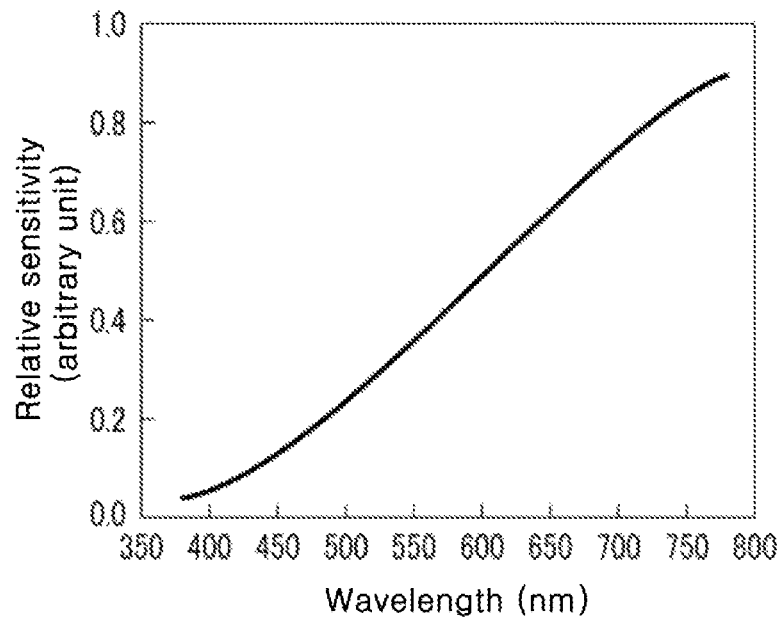
FIG. 21A is a diagram showing a spectral curve of blackbody radiation at 3000 K.
Figure 21B:
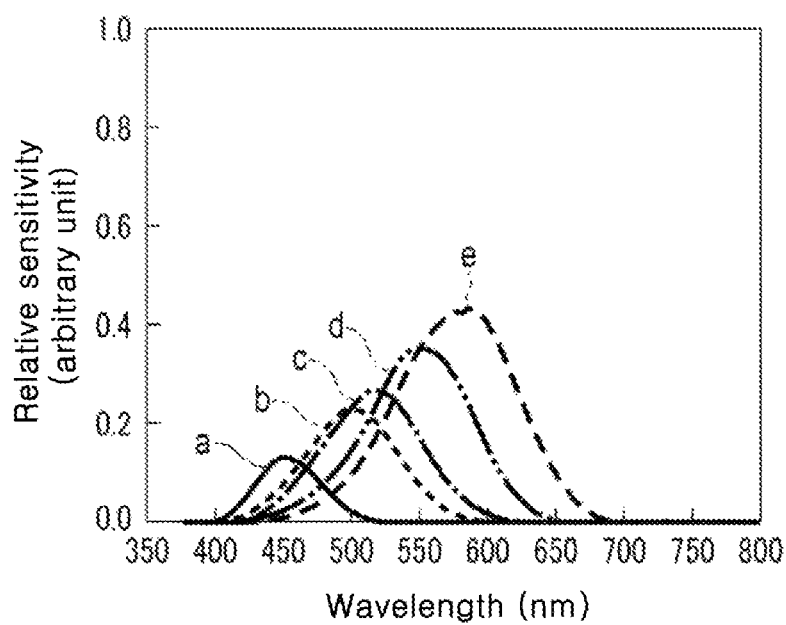
FIG. 21B is a diagram showing a spectral curve of α-opic irradiance of blackbody radiation.

Using the Equation (5A), for example, for a 3000K blackbody radiation spectrum shown in FIG. 21A, by calculating α-opic irradiances based on five types of action curves, five types of spectrum curves shown in FIG. 21B may be obtained.

The five types of curves in FIG. 21B are all α-opic irradiance for the blackbody radiation spectrum of 3000K. Among these, a curve a corresponds to a S-cone optic irradiance, a curve b corresponds to a melanopic irradiance, a curve c corresponds to a rhodopic irradiance, a curve d corresponds to an M-cone optic irradiance, and a curve e corresponds to an L-cone optic irradiance. If a ratio (melanopic irradiance/(L-cone opic irradiance+M-cone opic irradiance)) is calculated using three kinds of curves among the above five types, Equation (9) may be obtained in the following procedure.

Melanopic irradiance/(L-cone opic irradiance+M-cone opic irradiance)=(∫(spectrum of blackbody radiation)*(action curve of ipRGC)*$d\lambda$)/(∫(spectrum of blackbody radiation)*(action curve of L cone)*$d\lambda$+∫(spectrum of blackbody radiation)*(action curve of M cone)*$d\lambda$)=area of spectrum curve b/(area of spectrum curve e+area of spectrum curve d)=24.5(%)  (Equation 9)

Likewise, ratios of the black body radiation spectra of the four types of color temperatures from 4000K to 7000K were calculated and summarized in Table 5.

TABLE 5

| Color temperature | Ratio |
|---|---|
| 3000K | 24.5% |
| 4000K | 31.9% |
| 5000K | 37.2% |
| 6000K | 41.2% |
| 7000K | 44.1% |

As can be seen from the data in Table 5, the α-opic irradiance ratio showed a larger value as the color temperature of black body radiation increased. Although an optical response of ipRGC is maximum in a wavelength range of 480 nm to 490 nm, but looking at the black body radiation spectrum graph of FIG. 20, it can be seen that a luminous intensity in the above wavelength range changes in a direction that becomes stronger as the color temperature increases, and thus, changes to a larger value in response to the change in the luminous spectrum of black body radiation. Using the α-opic irradiance ratio of blackbody radiation calculated above, it was decided to standardize an application range of the light source of the present disclosure. Specifically, when the α-opic irradiance ratio of the light source of the present disclosure is A and the α-opic irradiance ratio of blackbody radiation of a same color temperature is B, a ratio A/B may be obtained as follows.

A/B=(α-opic irradiance ratio of the light source of the present disclosure)/(α-opic irradiance ratio of black body radiation)  (7)

Figure 19B:
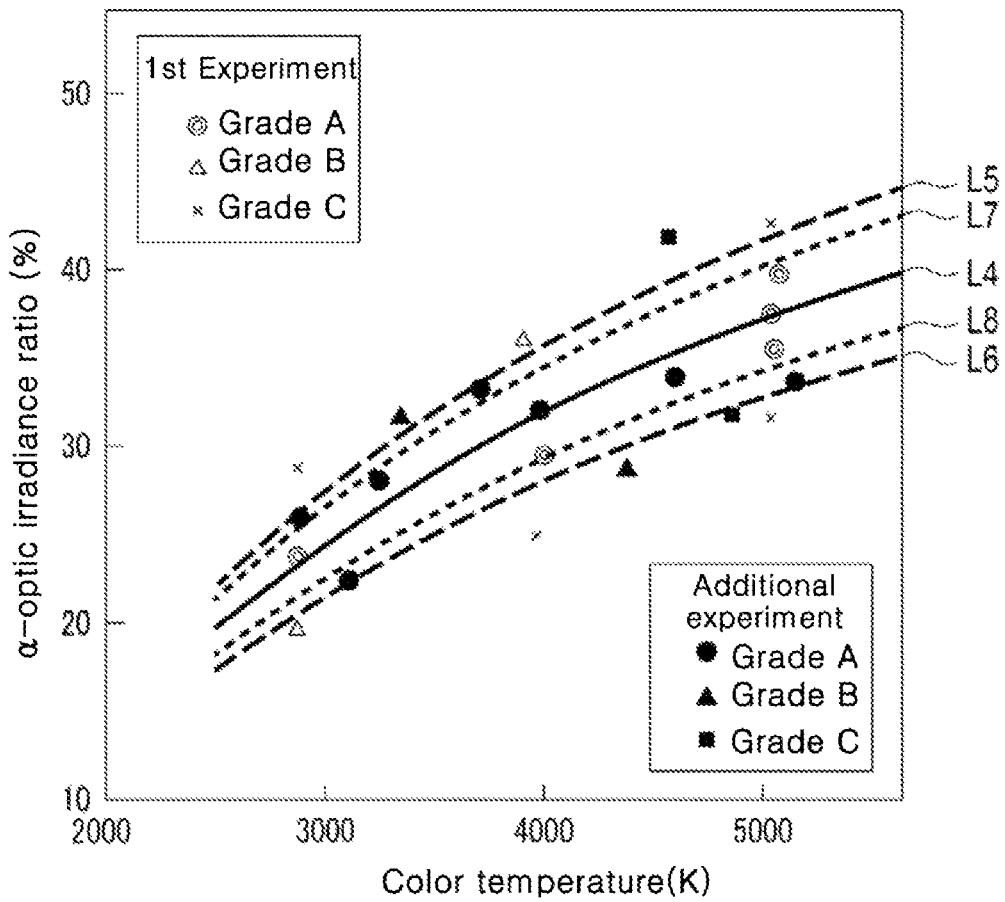
FIG. 19B is a diagram showing a relationship between the result shown in FIG. 19A and A/B ratio.

When the range of the white light source of the present disclosure is expressed using the A/B ratio obtained above, 0.88≤A/B≤1.11 Equation (2). In addition, it was possible to substitute it with 0.92≤A/B≤1.07 Equation (3) for a more preferable range. For example, when the value of the α-opic irradiance ratio shown on the straight line L2 in FIG. 19A above is 24.8% at a color temperature of 2900K, the A/B ratio is 1.05 (1.047), and similarly, the value of 37.5% at 5000K was also 1.01 (1.008), which was close to 1.00. A relationship between the results shown in FIG. 19A and the A/B ratio is shown graphically in FIG. 19B. In FIG. 19B, a solid line L4 is a curve representing the α-opic irradiance ratio of black body radiation, dashed lines L5 and L6 are curves representing a preferable range of the A/B ratio, and broken lines L7 and L8 are curves representing a more preferable range. In addition, a numerical range shown in the above Equations (2) and (3) corresponds to a region newly found by the present disclosure, indicating that it is a range that has a favorable effect on the secretion amount of melatonin and quality of sleep. By quantitatively changing the amount of stimulation light irradiated to the ipRGC by changing the luminous intensity of the white light source that satisfies the Equation (2), a person's circadian rhythm may be appropriately maintained, and thus, favorable sleep quality may be obtained.

Figure 22:
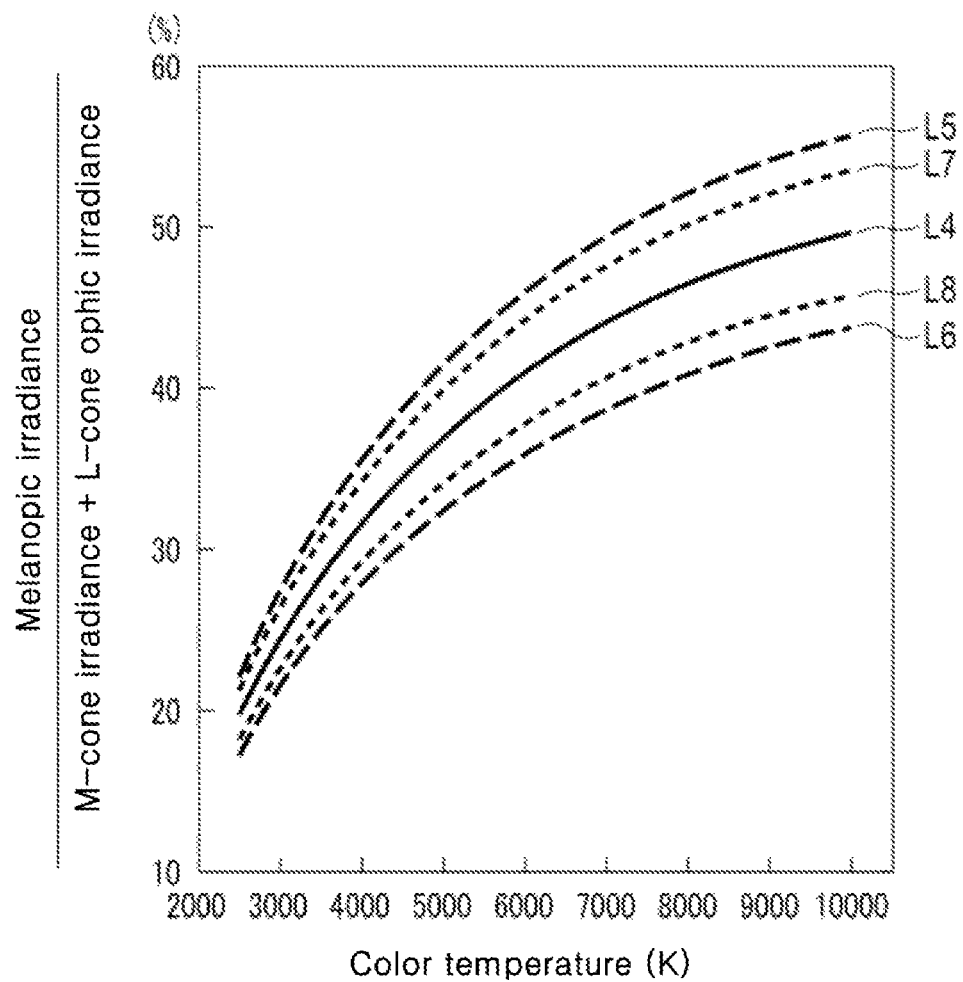
FIG. 22 is a diagram showing upper and lower limits of a A/B ratio of a white light source of the present disclosure.

FIG. 22 is a diagram showing a range of color temperatures expanded by replacing the numerical range of the preferred light source of the present disclosure using the newly introduced A/B ratio. A solid line L4 is a curve representing the α-opic irradiance of black body radiation, dashed lines L5 and L6 are curves representing the preferable range of the A/B ratio, and broken lines L7 and L8 are curves representing the more preferable range. By introducing these indicators, it became possible to manage the characteristics of the preferable α-opic irradiance ratio, which are different for each color temperature, based on a unified standard. By adjusting the emission spectral shape of the white light source such that A/B is within the range of the above ratio, the effect on the daily rhythm of the human body may be controlled. When the A/B ratio exceeds an upper limit of the range in the Equation (2) above, the amount of ipRGC stimulation becomes excessive and melatonin secretion is suppressed, which reduces sleep efficiency or causes sleep delay, causing a problem of poor sleep quality. Meanwhile, when the A/B ratio is below a lower limit of the range of the above Equation (2), the amount of stimulation to the ipRGC is insufficient, and thus, the internal clock cannot be reset, causing a problem in which the waking time is gradually delayed. As such, when the A/B ratio is out of an appropriate range, such as when it exceeds the upper limit or falls below the lower limit, the daily rhythm cannot be accurately recorded, which may lead to disease over a long period of time.

(Device Configuration of White Light Source)

Figure 23:
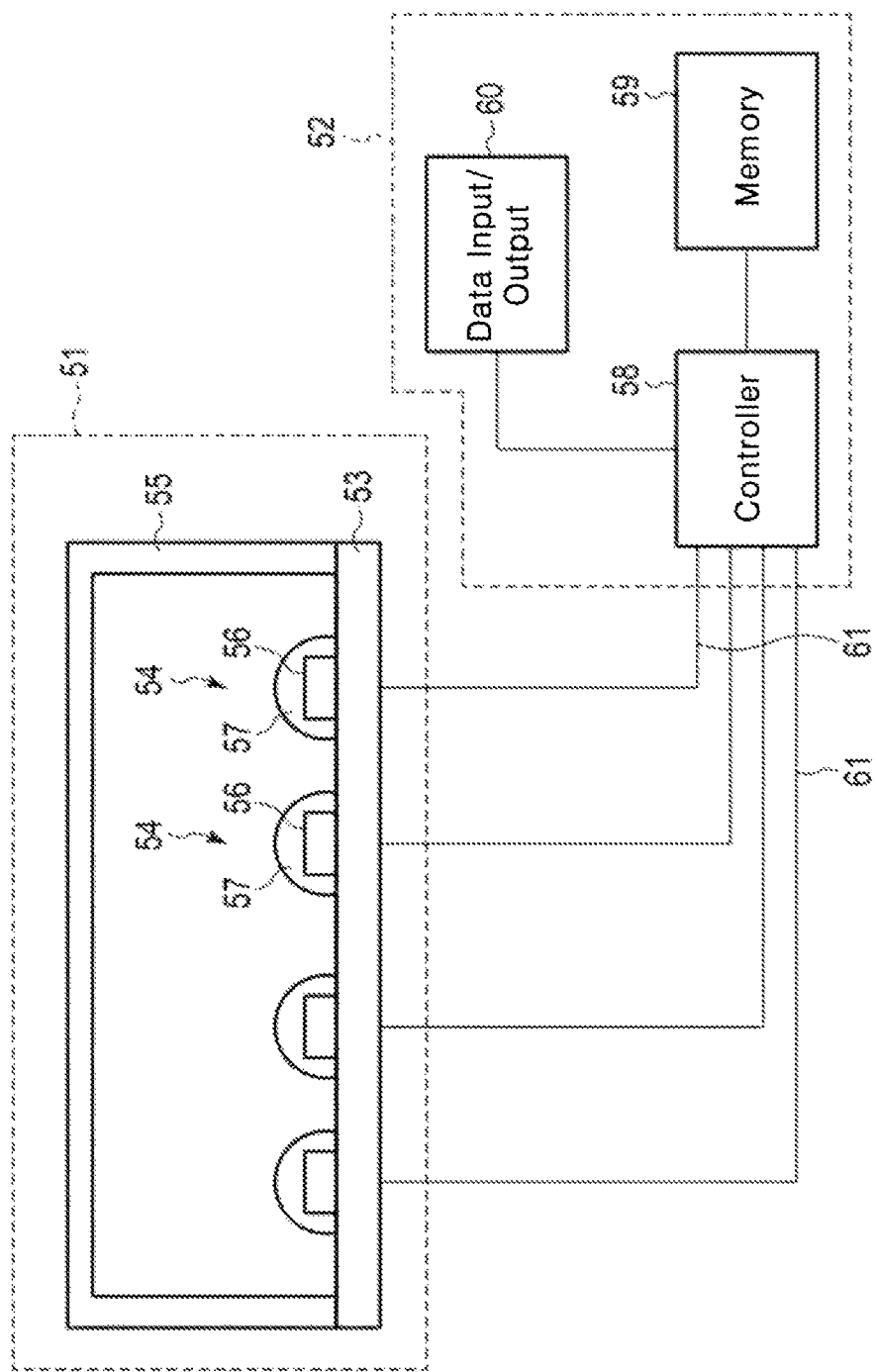
FIG. 23 is a diagram showing a device configuration of a white light source of the present disclosure.

An example of a device configuration of the white light source of the embodiment is shown in FIG. 23. As shown in FIG. 23, the white light source includes a white light source portion 51 and a control portion 52. The white light source portion 51 includes a substrate 53, a plurality of white light sources 54 disposed on the substrate 53, and a light emitting device enclosure 55 secured to the substrate 53 to cover the plurality of white light sources. Each of the plurality of white light sources 54 is constituted with an LED module. Of course, each of several white light sources 54 may be an LED package. The LED module includes an LED chip 56 disposed on the substrate 53 and a phosphor layer 57 disposed on the substrate 53 and covering the LED chip 56. An interconnection network is provided on the substrate 53, and electrodes of the LED chip 56 are electrically connected to the interconnection network of the substrate 53. In addition, the light emitting device enclosure 55 may have a lens (not shown in the drawings) disposed on an outer surface of a wall portion on a side opposite to the substrate 53. In addition, it is also possible to form at least a portion of the light emitting device enclosure 55 as a transparent portion capable of extracting light. The transparent portion is preferably formed on the wall portion on the side opposite to the substrate 53. In addition, a reflector (not shown in the drawings) may be disposed, for example, on an inner surface of the light emitting device enclosure 55. The control portion 52 includes a controller 58, a memory 59, and a data input/output 60. The white light source 54 formed of an LED module is connected to the electronic circuit (not shown in the drawings) of a controller 58 by an interconnection 61, and thus, the white light source 54 emits light by a current flowing from the controller 58 through the interconnection 61. In an electronic circuit memory 59 of the controller 58, a preset change pattern of color temperature, data of a color temperature change, or illuminance change of the day of sunlight are stored. A user inputs a type of data desired into the data input/output to send obtained data to the controller 58. The controller 58 extracts stored data corresponding to the input data, reads data of correlated color temperature and illuminance of a target white light emission, and calculates a mixing intensity ratio of each white light source based on these data. Based on calculation results, the electronic circuit of the controller 58 may control a current value applied to each white light source to reproduce a desired change in characteristics of white light. In addition, in the present disclosure, the control portion 52 may be further equipped with sensors (not shown in the drawings) to sense the illuminance around these sensors and transfer the sensed data to the control portion, thereby controlling a lighting device according to a surrounding illuminance.

(Dimming/Color Adjusting Function)

Figure 24:
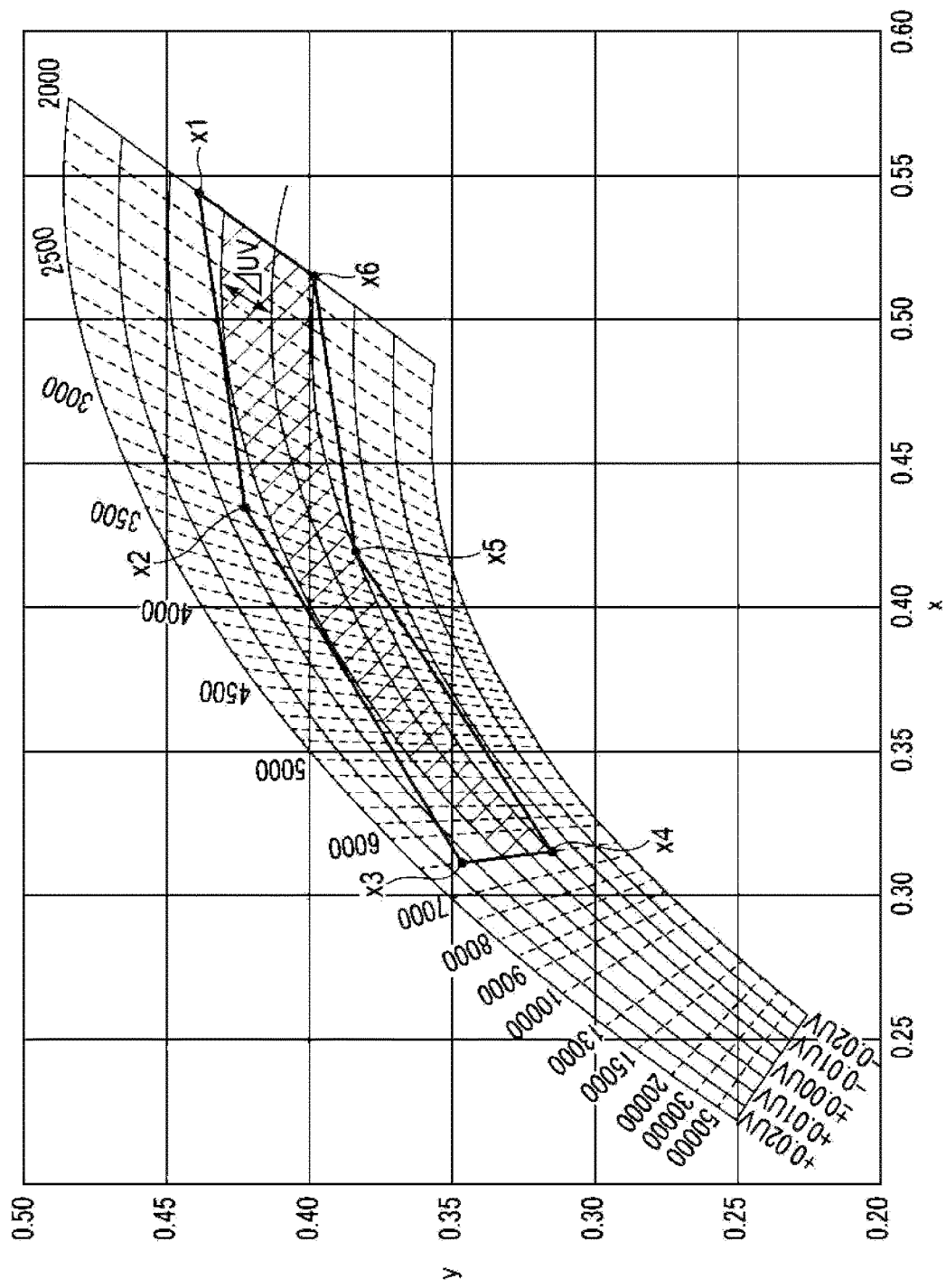
FIG. 24 is a diagram illustrating a dimming and color adjusting function of a white light source of the present disclosure.

In the white light source of the present disclosure, white light of any color temperature may be used at any illuminance for the purpose of appropriately managing the daily rhythm of the human body. For this purpose, for example, light sources of different color temperatures of X1, X2, X3, X4 are prepared as shown in an xy chromaticity diagram of FIG. 24, and it is possible to reproduce luminous colors within a range surrounded by six points: X1, X2, X3, X4, X5, and X6 by mixing at least two to three types of white light sources at a predetermined intensity ratio among these light sources. Each of these six light sources is the white light source of the present disclosure, and a melanopic irradiance ratio included in white light emission was adjusted to be similar to a melanopic irradiance ratio in corresponding white light of black body radiation of a same color temperature. As shown in FIG. 24, it can be seen that a range of this shape covers an entire white light region where a color temperature of a blackbody locus is from 2000K to 6500K, and a deviation from the blackbody locus is within a range of 0.005 duv. Therefore, in the white light source of the present disclosure, not only white light on the black body locus but also white light with various correlated color temperatures may be arbitrarily selected and reproduced. In this case, when mixing light from several white light sources, it is natural that a melanopic irradiance of mixed white light also represents an appropriate value, in terms that that each light source before mixing has an appropriate melanopic irradiance.

In addition, in the description of FIG. 24, only the color temperature range of 2000K to 6500K could be reproduced, but it is natural that a wider range of white light may be reproduced by setting an emission color corresponding to each vertex of a polygon to white of various correlated color temperatures. However, in the above white light source, six types of white light sources were arbitrarily mixed to obtain white light of the present disclosure, but as for the types of white light sources used as a background, it is better to use more white light sources, such as eight or ten types, and of course, it is possible to accurately reproduce sunlight of various color temperatures by using more white light sources. In particular, it is advantageous when reproducing white light with a wider range of color temperatures with a single white light source device. However, if there are too many types of basic light sources, a design of a dimming and color adjusting device will become complicated, and the effect of the present disclosure may be achieved at least by using at least four types of light sources.

(Method for Using White Light Source)

The white light source of the present disclosure may be used in various places in daily life. In a home, they may be a living room, library, study room, bedroom, and even a kitchen or bathroom. Moreover, with regard to business establishments, examples include offices and conference rooms in office buildings, workshops such as factories, and stores in commercial facilities. Other examples include medical facilities, hospitals, classrooms at schools, exhibition rooms at art galleries, museums, or others.

When using the light source of the present disclosure for the above indoor lighting, it is necessary to manage a luminous intensity of illumination light within an appropriate range. When the white light source is installed on an indoor ceiling or wall, a distance between the light source and an object to be illuminated is within a range of 0.3m to 5.0m, it is preferable that the object to be illuminated is illuminated at an illuminance within a range of 50 lux or more and 10,000 lux or less. In addition, when the object to be illuminated is an entire or a part of a human face, it may also be more preferable to confirm an illumination effect on a human body.

When the above-described illuminance exceeds an upper limit, even if the melanopic irradiance satisfies conditions required for the light source of the present disclosure, an intensity of irradiated light is too strong, so excessive light is received in the ipRGC, and thus, there is a risk of adverse effects such as a decrease in sleep efficiency. In addition, when the illuminance is below a lower limit, the intensity of the irradiated light is too weak, so that the ipRGC cannot receive the required amount of light, and thus, there is a risk of adverse effects that the internal clock does not function properly. Moreover, since a management range of melanopic irradiance is set on the condition that the illuminance required for work, etc. should be met, when the illuminance exceeds the upper limit, light is so strong that people feel dazzled, and when it is below the lower limit, light is so weak that it is difficult for people to see the object with their eyes. In this respect, it goes without saying that the management range is an insufficient usage condition as a light source for an original lighting purpose. Meanwhile, characteristics of illumination light are required according to a usage situation. An emission color is one of them, and the emission color is expressed in color temperature (K) Kelvin. For choosing a color temperature, it is preferable to use 5000K or more to 10000K or less in a high color temperature range when working, use 2000K or ore to 3500K or less in a low color temperature range when resting at home or before going to bed, and use 3500K or more to 5000K or less in activity areas such as schools, product sales, or the like. The white light source of the present disclosure was adjusted such that, for each (correlated) color temperature, the melanopic irradiance of white light was about a same as that of blackbody radiation of a same color temperature. Therefore, it is preferable in terms of maintaining an appropriate daily rhythm to select and use a light source having a dedicated color temperature according to a purpose or a place, such as for a living room or a bedroom.

Meanwhile, in offices, or the like, a same white light source is used under various conditions, such as work or break time, day work, or night work. In this case, it is possible to classify white light of various color temperatures according to a time zone and usage by using dimming and color adjusting functions of the light source of the present disclosure. In this case, the color temperature and the like may be set to a pre-set pattern, such as lighting in the morning, lighting during breaks, and lighting in the afternoon, and the pattern may be automatically managed using a program control. In such a usage method, if the white light source of the present disclosure is used, the melanopic irradiance can be controlled to an appropriate value according to the change in color temperature, so it goes without saying that it is effective for proper management of daily rhythm. In addition, in lighting applications such as hospital rooms, daily changes in sunlight intensity and color temperature may be automatically reproduced through a program control. Pre-measured solar luminescence characteristic data may be stored in an internal memory of a white light source device, and necessary data may be recalled and reproduced through the program control according to a request of a patient or doctor. In addition, by automatically turning lights on at sunrise or automatically turning them off at the time of lights-out, one can have a regular hospital stay through illumination control. When the white light source of the present disclosure is used in this way, long-term hospitalized patients may obtain a same illumination effect as outdoors while staying in the hospital room, which is expected to have the effect of preventing disruption of daily rhythm due to hospitalization or promoting return to society after discharge. Although typical usage cases are listed above, regardless of the above, if a usage method is devised according to the circumstances of daily life, the daily rhythm of the human body may be properly maintained with the light source of the present disclosure.

In addition, the white light source of the present disclosure is a light source having very high color rendering characteristics, with an average color rendering index Ra of 95 to 97 or more, and all of the color rendering coefficients R1 to R8 and special color rendering coefficients R9 to R15 are 85 to 90 or more. Accordingly, regardless of the effect on daily rhythm, it may be very effective even in applications requiring high color rendering. Therefore, it is optimal for lighting purposes such as exhibitions in art galleries and museums, or display cases in food supermarkets.

INVENTIVE EXAMPLE

Inventive Example 1

On an aluminum substrate with a reflection film formed on its surface, 80 purple LED chips with an emission peak at 415 nm were arranged in a matrix. The LED chips were connected to one another with metal wires and connected to an electrode. For the electrode, a copper plate plated with gold was used. Then, a periphery of the LED chip was covered with a fluorescent film, and surfaces of the fluorescent film and a conductive member were covered with a transparent resin film to form an LED module. The fluorescent film was created by dispersing a mixed powder of six types of phosphors in a silicone resin and then by coating it in a form of covering the periphery of the LED. The six types of phosphors are each one type of blue phosphor, cyan phosphor, green phosphor, red phosphor, respectively, and two types of yellow phosphor.

Figure 25:
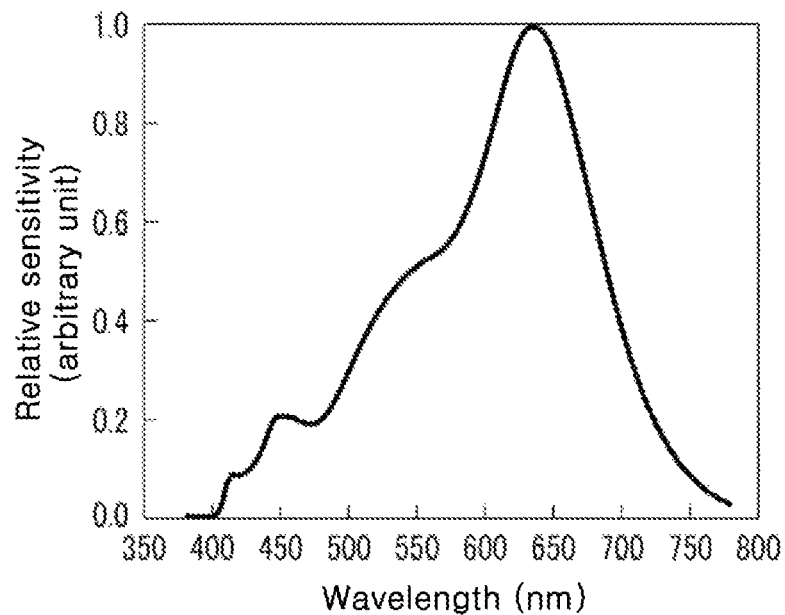
FIG. 25 is a diagram showing an emission spectrum of a white light source of Inventive Example 1.

In more detail, by mixing each of blue europium-activated alkaline earth phosphate phosphor, cyan europium-activated alkaline earth phosphate phosphor, green cerium-activated rare earth aluminum garnet phosphor, red europium-activated alkaline earth nitrido aluminum silicate phosphor, and yellow europium-activated orthosilicate phosphor and cerium-activated rare earth aluminum garnet phosphor, at a rate of 40.6:35.0:2.4:9.1:15.3:7.6, white light was obtained. An emission spectrum of obtained white light is shown in FIG. 25. A correlated color temperature of this emission spectrum was 2685K-0.001 duv. In addition, when a ratio A/B with black body radiation was calculated by obtaining three types of α-opic irradiance, it was 1.00, which was found to satisfy an appropriate range.

Inventive Example 2

An LED module was prepared in a same manner as that of the Inventive Example 1.

Figure 26:
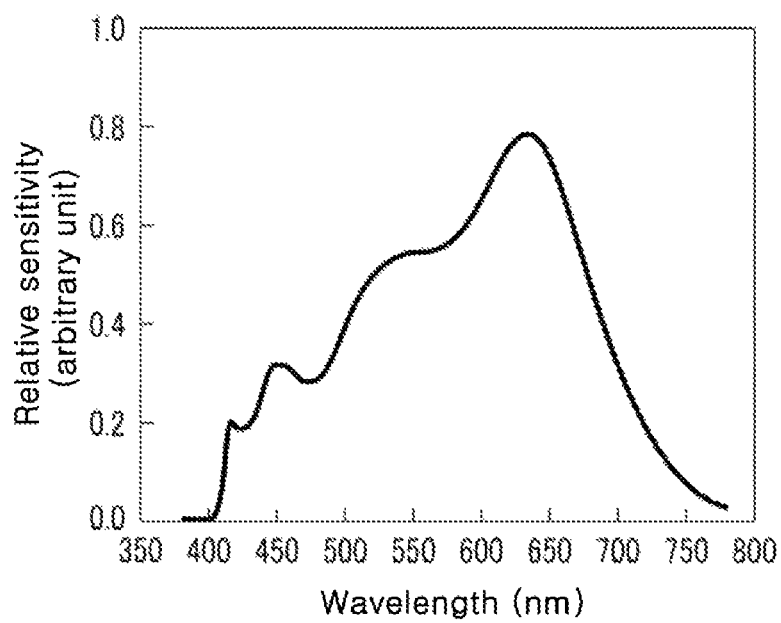
FIG. 26 is a diagram showing an emission spectrum of a white light source of Inventive Example 2.

Combinations of LEDs and phosphors used are as shown in Tables 7 to 9. An emission spectrum of obtained white light is shown in FIG. 26. A correlated color temperature of this emission spectrum was 3476K+0.001 duv. In addition, when a ratio A/B with black body radiation was calculated by obtaining three types of α-opic irradiance, it was 0.97, which satisfies an appropriate range. Moreover, color rendering characteristics of this light source showed a high numerical value as shown in Table 6 below, and when used as a light source, it was found to be a favorable white light capable of reproducing a color of an object in a natural form.

TABLE 6

| Ra | R1 | R2 | R3 | R4 | R5 | R6 | R7 | R8 | R9 | R10 | R11 | R12 | R13 | R14 | R15 |
|----|----|----|----|----|----|----|----|----|----|----|----|----|----|----|----|
| 98 | 97 | 100 | 95 | 95 | 98 | 99 | 98 | 98 | 99 | 98 | 93 | 97 | 98 | 96 | 99 |

TABLE 7

| | LED peak wavelength (nm) | Phosphor Luminous color | Phosphor name | Mixing ratio (wt %) | Correlated color temperature |
|---|---|---|---|---|---|
| Inventive Example 1 | Purple LED 415 | blue | Europium Activated Alkaline Earth Phosphate | 40.6 | 2685K − 0.001 duv |
| | | blue green | Europium Activated Alkaline Earth Phosphate | 35.0 | |
| | | green | Cerium Activated Rare Earth Aluminum Garnet | 2.4 | |
| | | yellow | Europium Activated Orthosilicate | 15.3 | |
| | | yellow | Cerium Activated Rare Earth Aluminum Garnet | 7.6 | |
| | | red | Europium Activated Alkaline Earth Nitrido Aluminum Silicate | 9.1 | |
| Inventive Example 2 | Purple LED 415 | blue | Europium Activated Alkaline Earth Phosphate | 37.8 | 3476K + 0.001 duv |
| | | blue green | Europium Activated Alkaline Earth Phosphate | 35.0 | |
| | | yellow | Europium Activated Orthosilicate | 12.5 | |
| | | yellow | Cerium Activated Rare Earth Aluminum Garnet | 7.5 | |
| | | red | Europium Activated Alkaline Earth Nitrido Aluminum Silicate | 7.2 | |
| Inventive Example 3 | Purple LED 415 | blue | Europium Activated Alkaline Earth Phosphate | 43.4 | 4983K + 0.002 duv |
| | | blue green | Europium Activated Alkaline Earth Phosphate | 39.7 | |
| | | yellow | Europium Activated Orthosilicate | 5.2 | |
| | | yellow | Cerium Activated Rare Earth Aluminum Garnet | 4.2 | |
| | | red | Europium Activated Alkaline Earth Oxonitrido Aluminum Silicate | 7.5 | |
| Inventive Example 4 | Purple LED 415 | blue | Europium Activated Alkaline Earth Phosphate | 51.7 | 6499K + 0.004 duv |
| | | blue green | Europium Activated Alkaline Earth Phosphate | 33.2 | |
| | | yellow | Europium Activated Orthosilicate | 5.0 | |
| | | yellow | Cerium Activated Rare Earth Aluminum Garnet | 4.1 | |
| | | red | Europium Activated Alkaline Earth Oxonitrido Aluminum Silicate | 6.0 | |

TABLE 8

| | LED peak wavelength (nm) | Phosphor Luminous color | Phosphor name | Mixing ratio (wt %) | Correlated color temperature |
|---|---|---|---|---|---|
| Inventive Example 5 | Purple LED 415 | blue | Europium Activated Alkaline Earth Phosphate | 52.3 | 8070K + 0.004 duv |
| | | blue green | Europium Activated Alkaline Earth Phosphate | 33.6 | |
| | | yellow | Europium Activated Orthosilicate | 4.7 | |
| | | yellow | Cerium Activated Rare Earth Aluminum Garnet | 3.8 | |
| | | red | Europium Activated Alkaline Earth Oxonitrido Aluminum Silicate | 6.6 | |
| Inventive Example 6 | Purple LED 415 | blue | Europium Activated Alkaline Earth Phosphate | 57.8 | 9540K + 0.000 duv |
| | | blue green | Europium Activated Alkaline Earth Phosphate | 31.6 | |
| | | yellow | Cerium Activated Rare Earth Aluminum Garnet | 6.4 | |
| | | red | Europium Activated Alkaline Earth Nitrido Aluminum Silicate | 2.0 | |
| | | red | Europium Activated Alkaline Earth Oxonitrido Aluminum Silicate | 2.2 | |
| Inventive Example 7 | Blue LED 435 450 475 | blue | — | — | 2750K + 0.004 duv |
| | | blue green | Europium Activated Strontium Aluminate | 30 | |
| | | green | Cerium Activated Rare Earth Aluminum Garnet | 15 | |
| | | yellow | Cerium Activated Rare Earth Aluminum Garnet | 25 | |
| | | red | Europium Activated Alkaline Earth Nitrido Aluminum Silicate | 30 | |

TABLE 8-continued

| | LED peak wavelength (nm) | Phosphor Luminous color | Phosphor name | Mixing ratio (wt %) | Correlated color temperature |
|---|---|---|---|---|---|
| Inventive Example 8 | Blue LED 435 450 475 | blue blue green green red red | — — Cerium Activated Rare Earth Aluminum Garnet Europium Activated Alkaline Earth Nitrido Aluminum Silicate Europium Activated Alkaline Earth Nitrido Aluminum Silicate | — — 50 25 25 | 5050K + 0.004 duv |

TABLE 9

| | LED peak wavelength (nm) | Phosphor Luminous color | Phosphor name | Mixing ratio (wt %) | Correlated color temperature |
|---|---|---|---|---|---|
| Comparative Example 1 | Purple LED 415 | blue blue green green yellow red | — Europium Activated Alkaline Earth Phosphate — Cerium Activated Rare Earth Aluminum Garnet Europium Activated Alkaline Earth Nitrido Aluminum Silicate | — 85 — 10 5 | 4430K + 0.014 duv |
| Comparative Example 2 | Blue LED 452 | blue blue green green yellow red | — — Europium Activated Orthosilicate Cerium Activated Rare Earth Aluminum Garnet Europium Activated Alkaline Earth Nitrido Aluminum Silicate | — — 40.0 30.0 30.0 | 4890K + 0.002 duv |
| Comparative Example 3 | Blue LED 451 | blue blue green green yellow red | — — — Cerium Activated Rare Earth Aluminum Garnet — | — — — 100 — | 5240K + 0.003 duv |
| Comparative Example 4 | Blue LED 452 | blue blue green green yellow red | — — Europium Activated Orthosilicate Cerium Activated Rare Earth Aluminum Garnet Europium Activated Alkaline Earth Nitrido Aluminum Silicate | — — 30.0 60.0 10.0 | 6360K + 0.004 duv |

Inventive Example 3

An LED module was prepared in a same manner as that of the Inventive Example 1. A combination of LEDs and phosphors used is as shown in Table 7.

Figure 27:
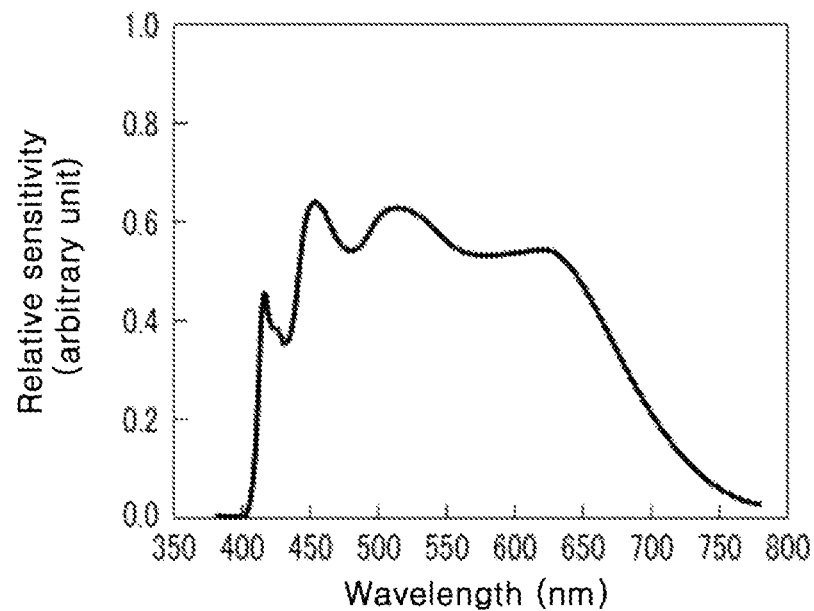
FIG. 27 is a diagram showing an emission spectrum of a white light source of Inventive Example 3.

An emission spectrum of obtained white light is shown in FIG. 27. A correlated color temperature of this emission spectrum was 4983K+0.002 duv. In addition, when a ratio A/B with black body radiation was calculated by obtaining three types of α-opic irradiance, it was 0.95, which was found to meet an appropriate range. Moreover, color rendering characteristics of this light source showed a high numerical value as shown in Table 10 below, and when used as a light source, it was found to be a favorable white light capable of reproducing a color of an object in a natural form.

Inventive Example 4

Figure 28:
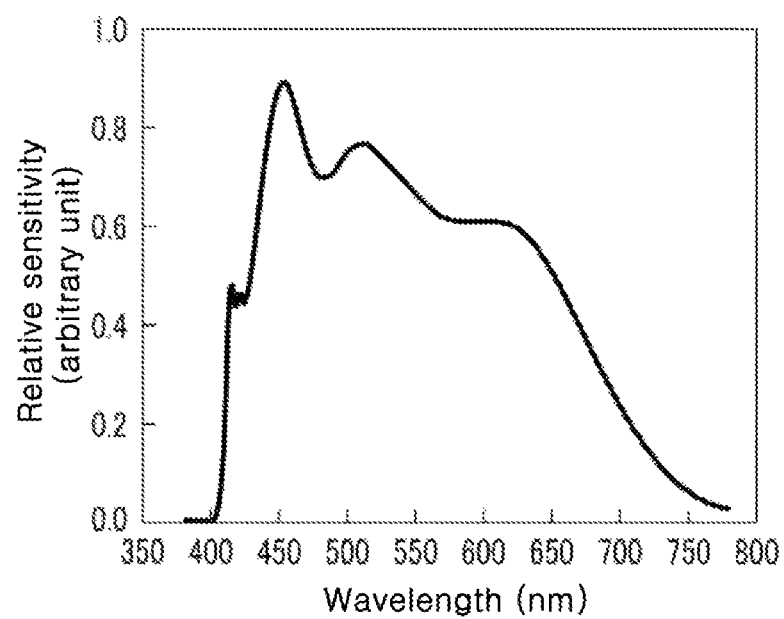
FIG. 28 is a diagram showing an emission spectrum of a white light source of Inventive Example 4.

An LED module was prepared in a same manner as that of the Inventive Example 1. A combination of LEDs and phosphors used is as listed in Table 7. An emission spectrum of obtained white light is shown in FIG. 28. A correlated color temperature of this emission spectrum was 6499K+ 0.004 duv. In addition, when a ratio A/B with black body radiation was calculated by obtaining three types of α-opic irradiance, it was 1.01, which satisfies an appropriate range.

Moreover, color rendering characteristics of this light source showed a high numerical value as shown in Table 11 below, and when used as an illumination light source, it was found to be a favorable white light capable of reproducing a color of an object in a natural form.

TABLE 10

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 98 | 98 | 98 | 98 | 98 | 98 | 98 | 97 | 98 | 97 | 96 | 96 | 93 | 98 | 99 | 98 |

TABLE 11

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 98 | 99 | 99 | 99 | 98 | 99 | 98 | 98 | 98 | 96 | 97 | 97 | 94 | 98 | 99 | 98 |

Inventive Example 5

Figure 29:
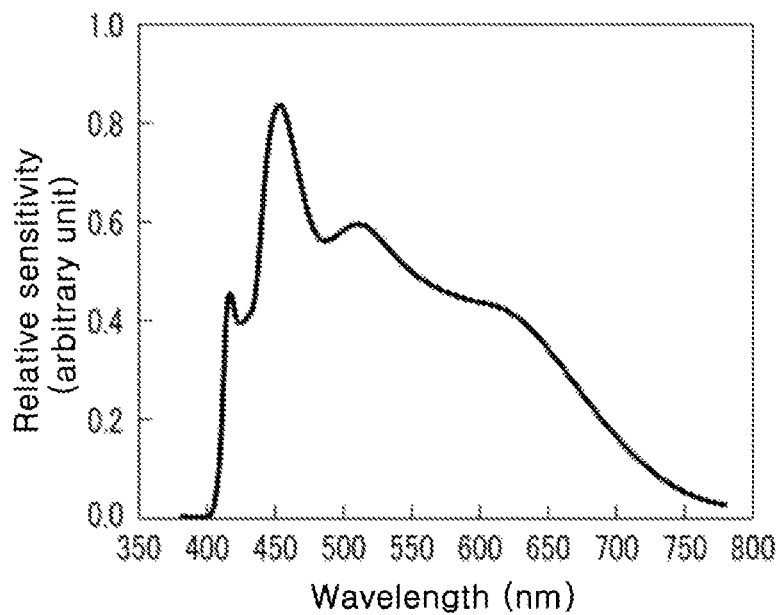
FIG. 29 is a diagram showing an emission spectrum of a white light source of Inventive Example 5.

An LED module was prepared in the same manner as that of the Inventive Example 1. A combination of LEDs and phosphors used is as shown in Table 7. An emission spectrum of obtained white light is shown in FIG. 29. A correlated color temperature of this emission spectrum was 8070K+0.004 duv. In addition, when a ratio A/B with black body radiation was calculated by obtaining three types of α-opic irradiance, it was 1.02, which satisfies an appropriate range. Moreover, color rendering characteristics of this light source showed a high numerical value as shown in Table 12 below, and when used as a light source, it was found to be a favorable white light capable of reproducing a color of an object in a natural form.

TABLE 12

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 99 | 99 | 100 | 99 | 99 | 99 | 98 | 98 | 97 | 91 | 99 | 98 | 91 | 99 | 99 | 98 |

Inventive Example 6

Figure 30:
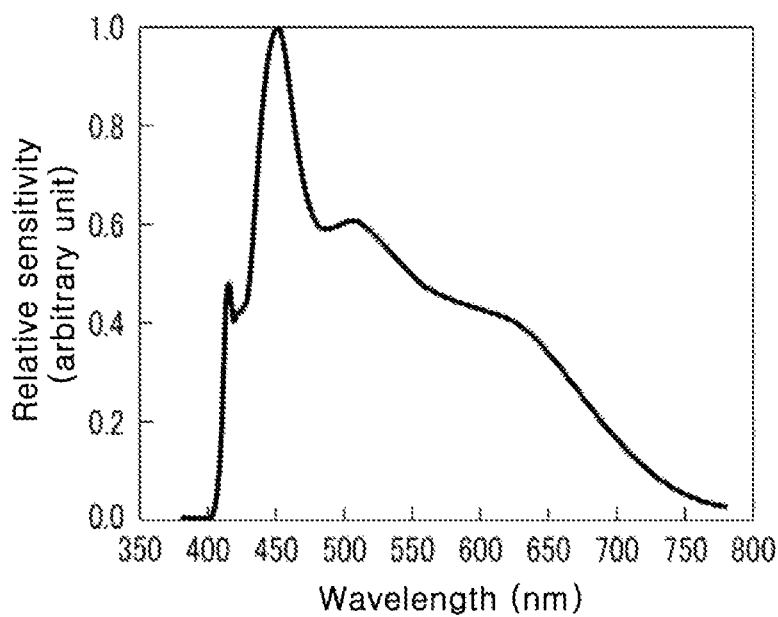
FIG. 30 is a diagram showing an emission spectrum of a white light source of Inventive Example 6.

An LED module was prepared in the same manner as that of the Inventive Example 1. A combination of LEDs and phosphors used is as listed in Table 7. An emission spectrum of obtained white light is shown in FIG. 30. A correlated color temperature of this emission spectrum was 9540K+0.000 duv. In addition, when a ratio A/B with black body radiation was calculated by obtaining three types of α-opic irradiance, it was 1.01, which satisfies an appropriate range. Moreover, color rendering characteristics of this light source showed a high numerical value as shown in Table 13 below, and when used as a light source, it was found to be a favorable white light capable of reproducing a color of an object in a natural form.

TABLE 13

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 98 | 96 | 98 | 99 | 98 | 97 | 97 | 99 | 99 | 96 | 97 | 95 | 90 | 97 | 99 | 96 |

Inventive Example 7

Figure 31:
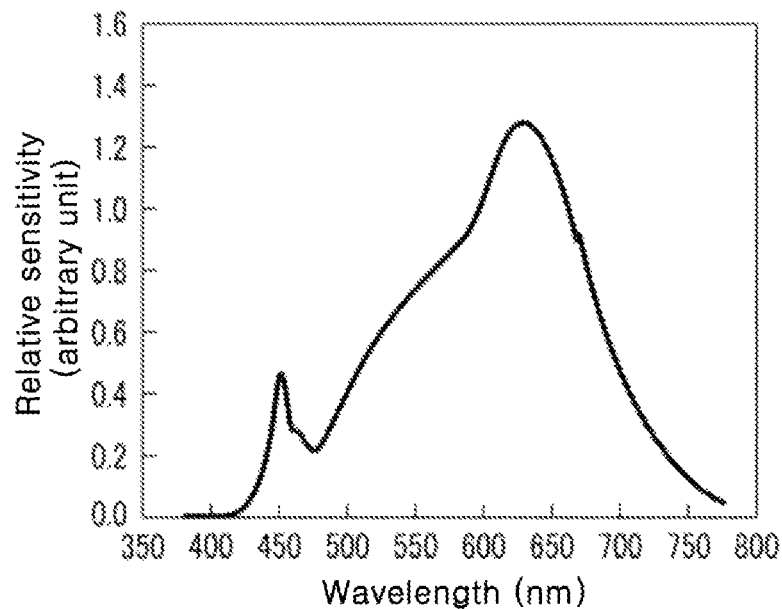
FIG. 31 is a diagram showing an emission spectrum of a white light source of Inventive Example 7.

An LED module was prepared in the same manner as that of the Inventive Example 1. A combination of LEDs and phosphors used is as listed in Table 7. An emission spectrum of obtained white light is shown in FIG. 31. A correlated color temperature of this emission spectrum was 2750K+0.004 duv. In addition, when a ratio A/B with black body radiation was calculated by obtaining three types of α-opic irradiance, it was 0.94, which satisfies an appropriate range. Moreover, color rendering characteristics of this light source showed a high numerical value as shown in Table 14 below, and when used as a light source, it was found to be a favorable white light capable of reproducing a color of an object in a natural form.

TABLE 14

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 96 | 97 | 97 | 95 | 98 | 96 | 97 | 97 | 92 | 81 | 92 | 98 | 84 | 97 | 96 | 95 |

Inventive Example 8

Figure 32:
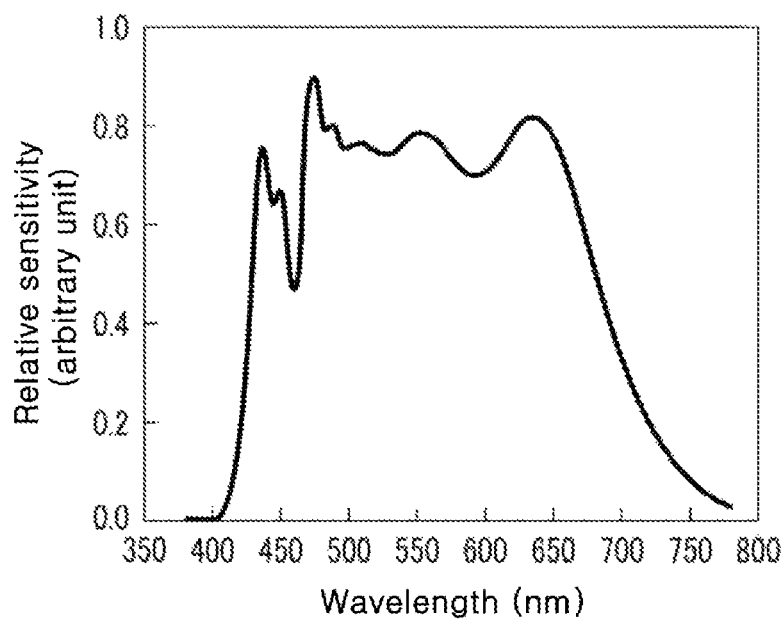
FIG. 32 is a diagram showing an emission spectrum of a white light source of Inventive Example 8.

An LED module was prepared in the same manner as that of the Inventive Example 1. A combination of LEDs and phosphors used is as listed in Table 7. An emission spectrum of obtained white light is shown in FIG. 32. A correlated color temperature of this emission spectrum was 5050K+0.004 duv. In addition, when a ratio A/B with black body radiation was calculated by obtaining three types of α-opic irradiance, it was 1.02, which satisfies an appropriate range. Moreover, color rendering characteristics of this light source showed a high numerical value as shown in Table 15 below, and when used as a light source, it was found to be a favorable white light capable of reproducing a color of an object in a natural form.

TABLE 15

| Ra | R1 | R2 | R3 | R4 | R5 | R6 | R7 | R8 | R9 | R10 | R11 | R12 | R13 | R14 | R15 |
|---|---|---|---|---|---|---|---|---|---|---|---|---|---|---|---|
| 98 | 98 | 98 | 98 | 97 | 98 | 98 | 98 | 98 | 93 | 95 | 98 | 96 | 98 | 99 | 98 |

Comparative Example 1

Figure 33:
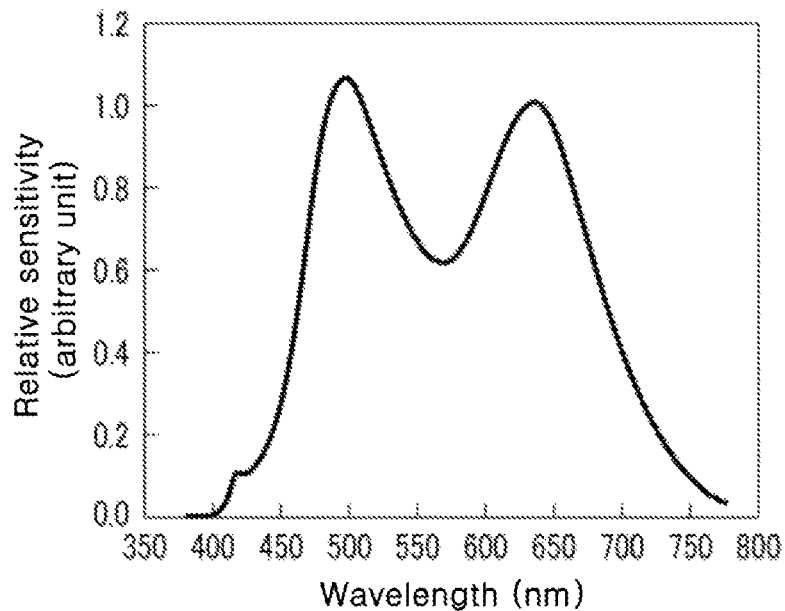
FIG. 33 is a diagram showing an emission spectrum of a white light source of Comparative Example 1.

An LED module was prepared in the same manner as that of the Inventive Example 1. A combination of LEDs and phosphors used is as listed in Table 7. An emission spectrum of obtained white light is shown in FIG. 33. A correlated color temperature of this emission spectrum was 4430K+0.014 duv. In addition, when a ratio A/B with black body radiation was calculated by obtaining three types of α-opic irradiance, it was 1.14, which was out of the appropriate range. In addition, an average color rendering index of this light source was low at 81, and thus, when this light source was used for lighting, objects could not be reproduced in natural colors, and only inadequate characteristics were obtained.

Comparative Example 2

Figure 34:
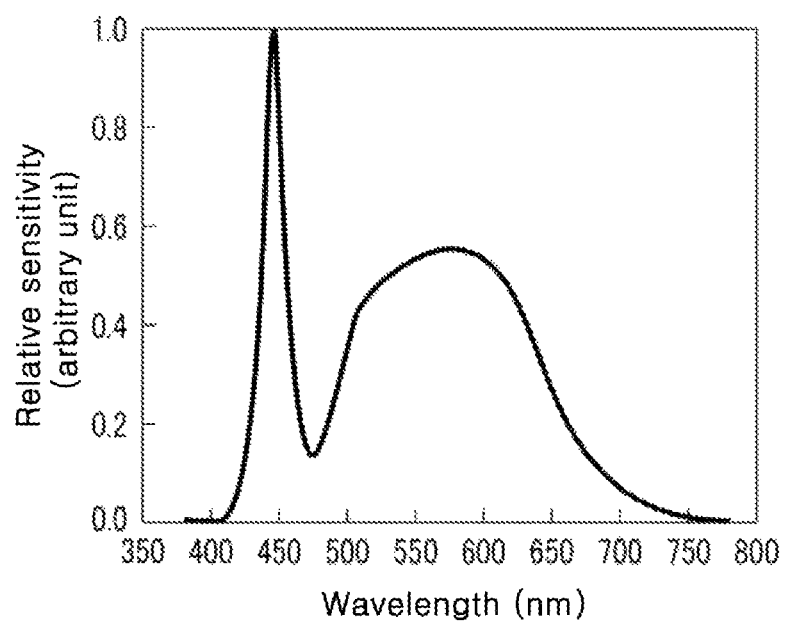
FIG. 34 is a diagram showing an emission spectrum of a white light source of Comparative Example 2.

An LED module was prepared in the same manner as that of the Inventive Example 1. A combination of LEDs and phosphors used is as listed in Table 7. An emission spectrum of obtained white light is shown in FIG. 34. A correlated color temperature of this emission spectrum was 4890K+0.002 duv. In addition, when a ratio A/B with black body radiation was calculated by obtaining three types of α-opic irradiance, it was 0.85, which was out of the appropriate range. In addition, an average color rendering index of this light source was low at 82, and thus, when this light source was used for lighting, objects could not be reproduced in natural colors, and only inadequate characteristics were obtained.

Comparative Example 3

Figure 35:
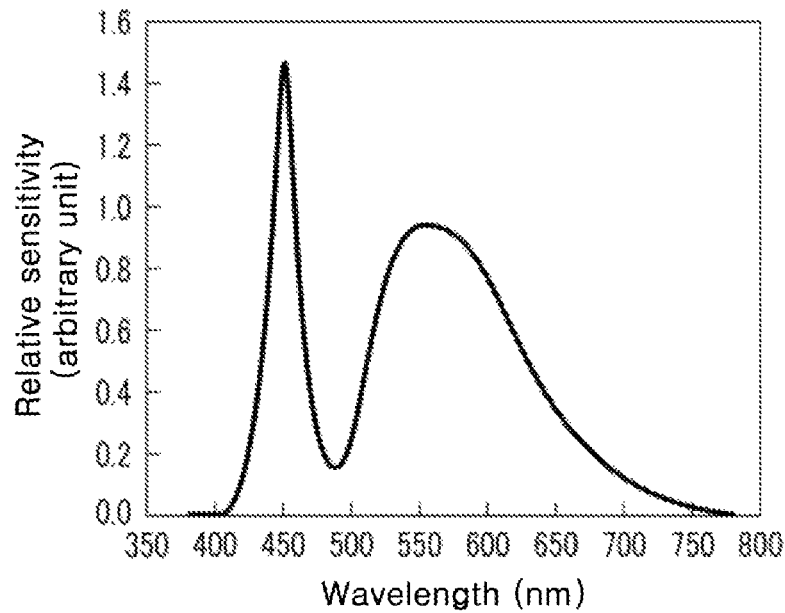
FIG. 35 is a diagram showing an emission spectrum of a white light source of Comparative Example 3.

An LED module was prepared in the same manner as that of the Inventive Example 1. A combination of LEDs and phosphors used is as listed in Table 7. An emission spectrum of obtained white light is shown in FIG. 35. A correlated color temperature of this emission spectrum was 5240K+0.003 duv. In addition, when a ratio A/B with black body radiation was calculated by obtaining three types of α-opic irradiance, it was 0.78, which was out of the appropriate range. In addition, an average color rendering index of this light source was low at 72, and thus, when this light source was used for lighting, objects could not be reproduced in natural colors, and only inadequate characteristics were obtained.

Comparative Example 4

Figure 36:
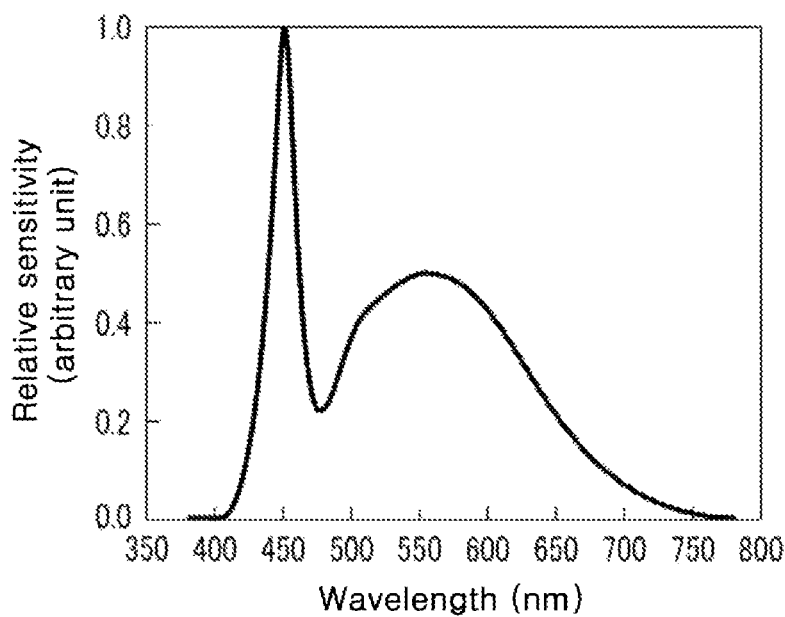
FIG. 36 is a diagram showing an emission spectrum of a white light source of Comparative Example 4.

An LED module was prepared in the same manner as that of the Inventive Example 1. A combination of LEDs and phosphors used is as listed in Table 7. An emission spectrum of obtained white light is shown in FIG. 36. A correlated color temperature of this emission spectrum was 6360K+0.004 duv. In addition, when a ratio A/B with black body radiation was calculated by obtaining three types of α-opic irradiance, it was 0.87, which was out of the appropriate range. In addition, an average color rendering index of this light source was low at 83, and thus, when this light source was used for lighting, objects could not be reproduced in natural colors, and only inadequate characteristics were obtained.

The color temperatures, A, B and A/B, and color rendering characteristics (Ra, R1 to R15) of the black body radiation of the Inventive Examples 1 to 8 and Comparative Examples 1 to 4 are summarized in that order in Tables 16 and 17.

TABLE 16

| Color temperature (K) of B | | | |
|---|---|---|---|
| Color temperature (K) of black body radiation | B | A | A/B |
| Inventive Example 1 | 2685 | 21.8 | 21.7 | 1.00 |
| Inventive Example 2 | 3476 | 28.5 | 27.7 | 0.97 |
| Inventive Example 3 | 4983 | 39.3 | 37.5 | 0.95 |
| Inventive Example 4 | 6499 | 42.7 | 43.3 | 1.01 |
| Inventive Example 5 | 8070 | 46.0 | 47.0 | 1.02 |
| Inventive Example 6 | 9540 | 49.0 | 49.5 | 1.01 |
| Inventive Example 7 | 2750 | 22.3 | 21.0 | 0.94 |
| Inventive Example 8 | 5050 | 38.2 | 37.5 | 1.02 |
| Comparative Example 1 | 4430 | 39.2 | 34.4 | 1.14 |
| Comparative Example 2 | 4890 | 31.1 | 36.7 | 0.85 |
| Comparative Example 3 | 5240 | 29.9 | 38.3 | 0.78 |
| Comparative Example 4 | 6360 | 37.3 | 42.7 | 0.87 |

A . . . Melanopic irradiance of white light source/(L-cone opic irradiance+M-con opic irradiance) ratio B . . . Melanopic irradiance of blackbody radiation of a same color temperature as that of a white light source/(L-con opic irradiance+M-con opic irradiance) ratio

TABLE 17

| Color temperature (K) of black body radiation | B | A | A/B |
|---|---|---|---|
| Inventive Example 1 | 2685 | 21.8 | 21.7 | 1.00 |
| Inventive Example 2 | 3476 | 28.5 | 27.7 | 0.97 |
| Inventive Example 3 | 4983 | 39.3 | 37.5 | 0.95 |
| Inventive Example 4 | 6499 | 42.7 | 43.3 | 1.01 |
| Inventive Example 5 | 8070 | 46.0 | 47.0 | 1.02 |
| Inventive Example 6 | 9540 | 49.0 | 49.5 | 1.01 |
| Inventive Example 7 | 2750 | 22.3 | 21.0 | 0.94 |
| Inventive Example 8 | 5050 | 38.2 | 37.5 | 1.02 |

TABLE 17-continued

|  | Color temperature (K) of black body radiation | B | A | A/B |
|---|---|---|---|---|
| Comparative Example 1 | 4430 | 39.2 | 34.4 | 1.14 |
| Comparative Example 2 | 4890 | 31.1 | 36.7 | 0.85 |
| Comparative Example 3 | 5240 | 29.9 | 38.3 | 0.78 |
| Comparative Example 4 | 6360 | 37.3 | 42.7 | 0.87 |

Inventive Example 9

As in the Inventive Examples and Comparative Examples shown above, white light sources with various color temperatures and A/B ratios were separately prepared and their effects on the daily rhythm of the human body were verified. For the experiment to verify, with the cooperation of college students, various light emitting devices were brought into a campsite, which was conducted as a part of the spring break club activity, and a white light source comparison test was conducted.

(Overview of Participants)

A total of 20 male and female college students participated. The breakdown includes 10 people belonging to a tennis club and 10 people belonging to an ESS (English Studies) club. As the verification experiment was conducted, each of the club members was divided into 5 people and a total of 4 teams were formed. The selection of group members was made in consideration of the activities of each club, and no consideration was given to their relationship with the verification experiment. Therefore, a composition ratio of men and women, age, etc. is arbitrary. In addition, all participants in the verification experiment were normal people, and no one had a history of special diseases or was taking special medications during the experiment period.

(Time Schedule of Verification Experiment)

The experiment lasted 5 consecutive days. The venue is a training facility in downtown Yokohama, with two outdoor tennis courts and indoor accommodations including multiple conference rooms, a large assembly hall, and lodging facilities such as private rooms for participants.

<Common Schedule>

The activity schedule common to all participants was performed according to the table in FIG. 37. In principle, group activities were conducted in accordance with the club's policy during the time between breakfast and dinner. However, outdoor activities were prohibited except for Club Activities 1 to 4 and break times, and indoor activities are the principle. In addition, time in the morning, bedtime and free time were, in principle, to be spent in their own rooms. However, people were free to chat in each indoor meeting room. In addition, the curtains in each living room were closed to prevent light from outside entering the room. In addition, lights were turned off at 11 p.m., lights were turned on at 7 a.m., and the operation was automatic, so that each person couldn't turn off or turn on the lights at their will. As a precaution in life, smartphone use was limited to 30 minutes each in the morning and afternoon. In addition, there were no restrictions on smoking during the camp, but alcohol was prohibited.

<Individual Schedule>

In the experiment, two groups per club, a total of four groups, participated in camp activities in different environments. Two groups of tennis club were T1 and T2, and two groups of ESS club were E1 and E2, and lighting conditions thereof were distinguished. Luminous characteristics of a white light source used in each group are shown in Table 18.

TABLE 18

| | Group, lighting conditions | Wake up, washing breakfast, etc. | Club activity 1 | rest | Club activity 2 | Lunch rest | Club activity 3 | rest | Club activity 4 | Meeting bathing, dinner | Free time |
|---|---|---|---|---|---|---|---|---|---|---|---|
| T1 | Color temperature (K) | 4500 | Outdoors | | Outdoors | 4500 | Outdoors | | Outdoors | 3500 | 3500 |
| | Illuminance (lux) | 400 | — | | — | 400 | — | | — | 300 | 500 |
| | Ratio (A/B) | 1.01 | — | | — | 1.00 | — | | — | 1.02 | 0.99 |
| T2 | Color temperature (K) | 4500 | Outdoors | | Outdoors | 4500 | Outdoors | | Outdoors | 3500 | 3500 |
| | Illuminance (lux) | 500 | — | | — | 400 | — | | — | 300 | 500 |
| | Ratio (A/B) | 1.15 | — | | — | 1.00 | — | | — | 1.02 | 1.15 |
| E1 | Color temperature (K) | 4500 | Continuous change | | Continuous change | 4500 | Continuous change | | Continuous change | 3500 | 3500 |
| | Illuminance (lux) | 400 | Continuous change | | Continuous change | 400 | Continuous change | | Continuous change | 300 | 500 |
| | Ratio (A/B) | 1.01 | Approx 1.00 | | Approx 1.00 | 1.00 | Approx 1.00 | | Approx 1.00 | 1.02 | 0.99 |
| E2 | Color temperature (K) | 4500 | Continuous change | | Continuous change | 4500 | Continuous change | | Continuous change | 3500 | 3500 |
| | Illuminance (lux) | 400 | Continuous change | | Continuous change | 400 | Continuous change | | Continuous change | 300 | 500 |
| | Ratio (A/B) | 0.75 | Approx 0.79 | | Approx 0.79 | 1.00 | Approx 0.79 | | Approx 0.79 | 1.02 | 0.74 |

As can be seen in Table 18, a color temperature and brightness of the white light source of indoor lighting were set to be same for all groups throughout each time zone, and only a A/B ratio was different between each group. In addition, a white light source used during lunch breaks, meetings, bathing, and dinner times was to be common to all groups. As you can see a difference in lighting conditions between groups, each characteristic is summarized as follows.

Group T1 participated in outdoor activities such as running and practice games during club activities. During the five days of the camp, it rained only one day, but it was a shower for about 30 minutes, and other than that, it was mostly clear and sunny. Meanwhile, in principle, time other than club activities was spent indoors. Among indoor lighting, an A/B ratio of private room lighting was used within a range of the claim in the present disclosure.

Group T2 spent time doing same exercises in a same environment as those of the Group T1 during club activities. Activity contents for the time other than the club activities were same as those of T1, but the A/B ratio of the indoor lighting was used to exceed an upper limit of the claim of the present disclosure.

Group E1 worked inside the conference room during club activities. The activities included research presentations, group discussions, and reading of literature and magazines. For the lighting of the conference room, a dimming/color adjusting lighting device that reproduces the change of sunlight was used. An A/B ratio of a white light source used in the dimming/color adjusting lighting device was within the range of the claim of the present disclosure. In addition, in principle, time other than club activities was spent indoors. Among the indoor lighting, an A/B ratio of private room lighting was used within the range of claim in the present disclosure.

In principle, activities of Group E2 were same as those of the Group E1. However, A/B ratios of a dimming/color adjusting light emitting device and private room lighting were used, which were below a lower limit of the claim in the present disclosure.

<Dimming/Color Adjusting Device>

Figure 38:
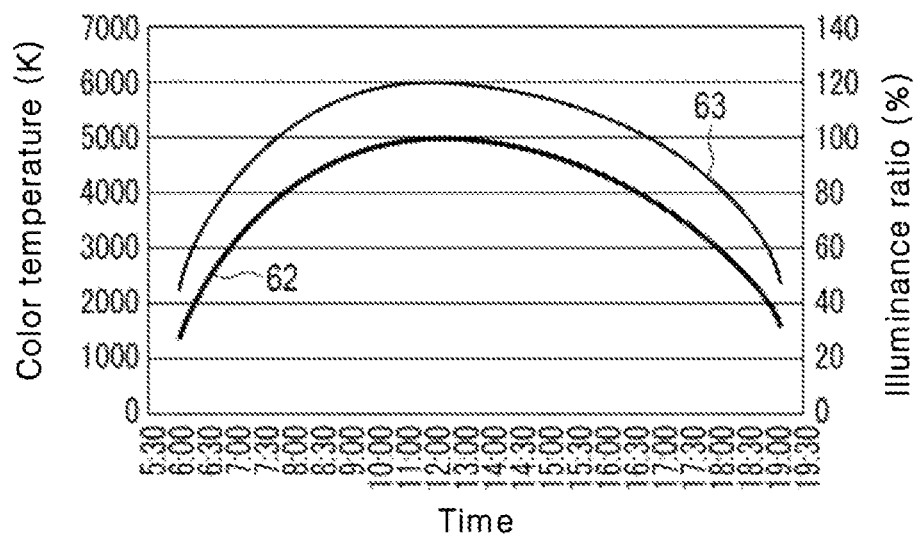
FIG. 38 is a diagram showing a change in luminance characteristics of sunlight from sunrise to sunset in Yokohama city in March.

A lighting of the conference room used by the Groups E1 and E2 for Club Activities 1-4 used a dimming and color adjusting device that can reproduce changes in the luminous characteristics of sunlight. Specific color temperature and illuminance changes were carried out according to the schedule in FIG. 38. A curve in FIG. 38 shows the change in luminescence characteristics of sunlight in March actually measured in Yokohama city. A curve 63 represents the change in color temperature of sunlight, and a curve 62 represents the change in illuminance ratio of sunlight. The color temperature of sunlight was reproduced by mixing four types of white light sources shown in Table 19. By mixing at least two to three types of light sources out of four types at a predetermined intensity ratio, a color temperature on a lotus of black body radiation between 4000K and 6000K was faithfully reproduced. In the color temperature change curve 63 and the illuminance ratio change curve 62 in FIG. 38, the color temperature change and the illuminance ratio change corresponding to the time periods described as continuous change in Table 18 (for example, from 8:30 a.m. to 10 a.m.) were reproduced. The color temperature and illuminance changes shown in FIG. 38 were stored in a memory of the light emitting device, and a control portion in the device recalled the stored data as needed and controlled a program thereof to reproduce the changes in sunlight. The luminous color was changed by reading new data every 3 minutes, but since a chromaticity change between them occurred only within a MacAdam ellipse on a xy chromaticity diagram, lighting users were unable to identify a moment when the color temperature changed, so the difference was observed as if it changed continuously. In addition, this device automatically reads a time when the lighting device is turned on and retrieves color temperature and illuminance data tailored to the time, and thus, it is designed to reproduce continuous changes tailored to actual sunlight even when lighting is interrupted.

TABLE 19

| | Group E1 | | Group E2 | |
|---|---|---|---|---|
| White light source 1 | 3998K + 0.005 duv | A/B = 1.00 | 3999K + 0.005 duv | A/B = 0.79 |
| White light source 2 | 3998K − 0.005 duv | | 3997K − 0.005 duv | |
| White light source 3 | 6001K + 0.005 duv | | 6005K + 0.005 duv | |
| White light source 4 | 6003K − 0.005 duv | | 6003K − 0.005 duv | |

(In Vivo Response Investigation)

Every night at 10 p.m., the participant's saliva was collected and a concentration of melatonin contained in the saliva was checked. In addition, after breakfast every day, a survey was conducted on the participant's sleep state. Contents of questionnaires were divided into three parts: (1) each person's subjective evaluation of one's sleep state (5-level evaluation), (2) sleep quality evaluation (whether or not one wakes up during sleep, and (3) number of awakenings), (3) awakening evaluation (time to open eyes).

(Evaluation Results of Biological Response)

Figure 39:
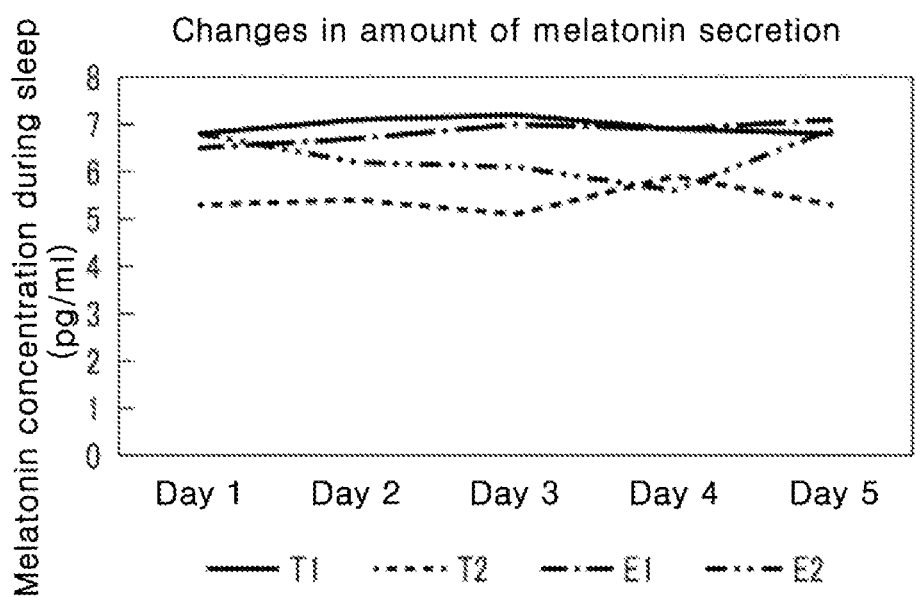
FIG. 39 is a diagram showing a measurement result of concentration of melatonin contained in the saliva of experimental participants.
Figure 40:
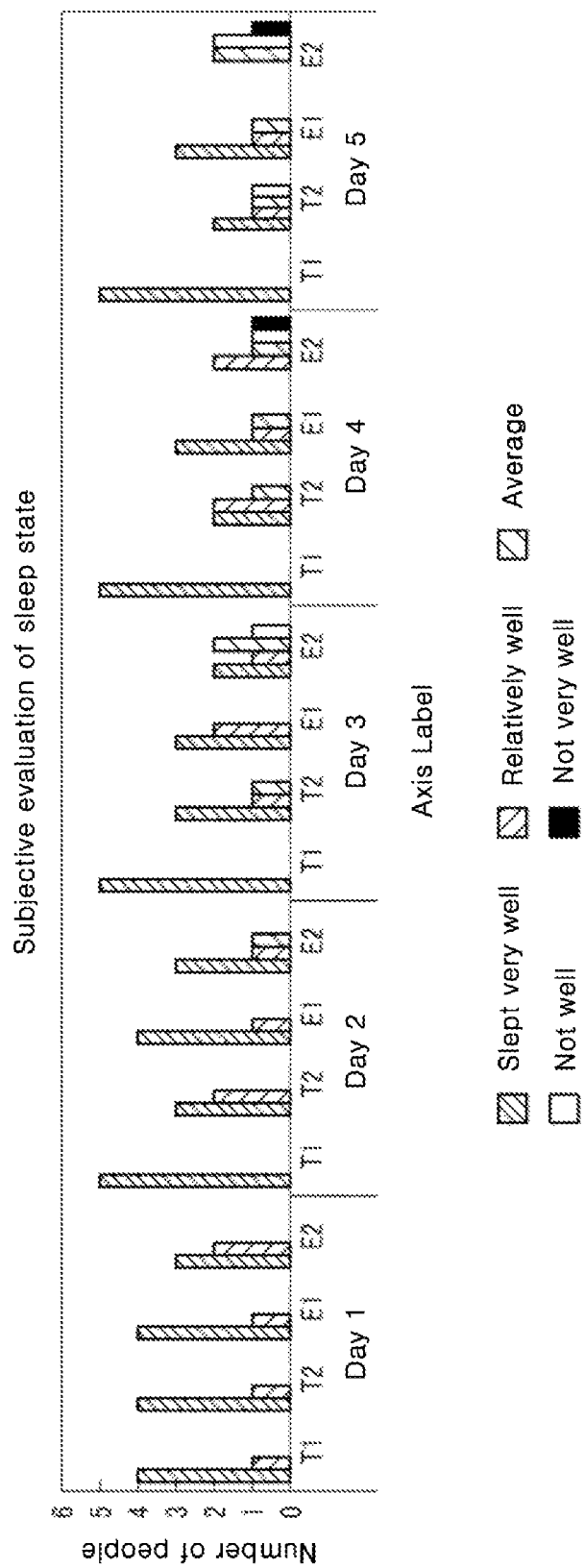
FIG. 40 is a diagram summarizing results of a questionnaire regarding subjective evaluation of sleep state.
Figure 41:
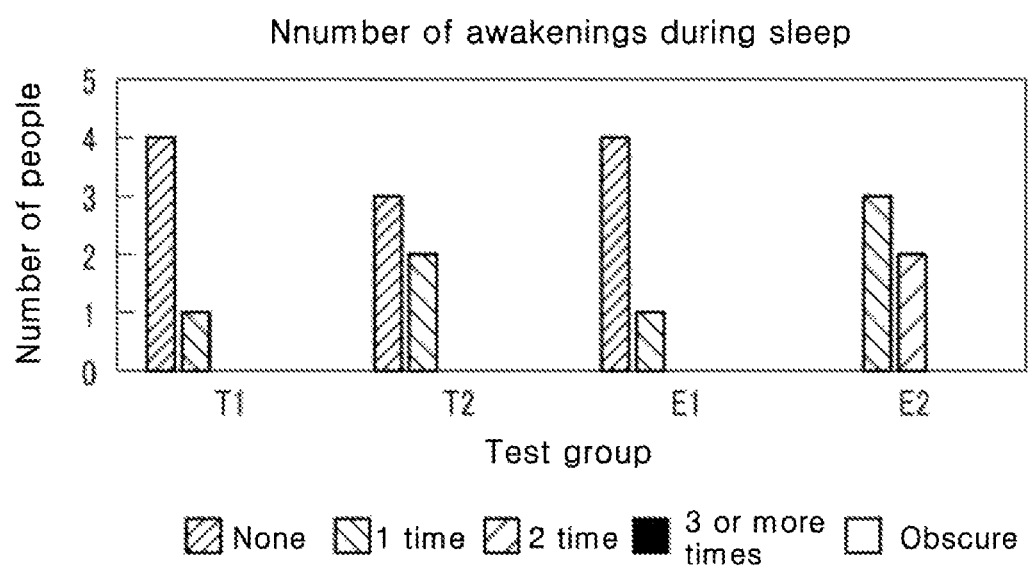
FIG. 41 is a diagram summarizing results of a questionnaire regarding the number of awakenings during sleep.
Figure 42:
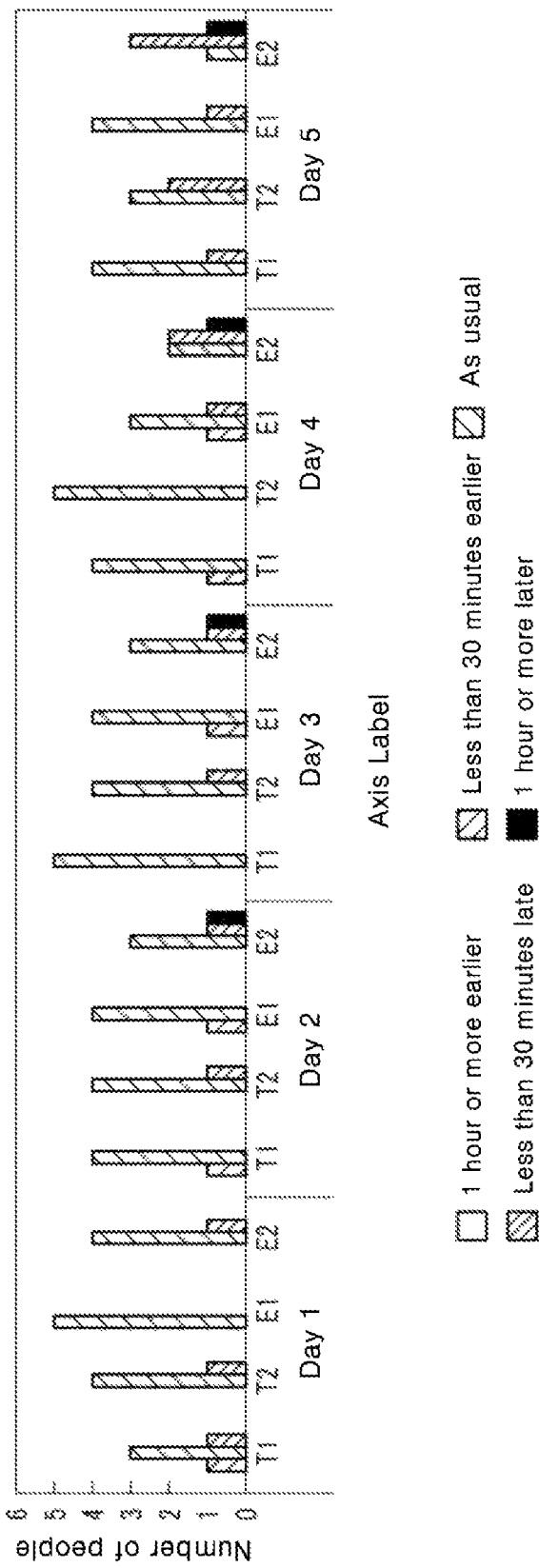
FIG. 42 is a diagram summarizing results of a questionnaire regarding waking time.

The experimental participants were divided into four groups: T1, T2, E1, and E2, and the survey results were collected and organized by group. In FIGS. 39 to 42, the results of each survey item are summarized in a graph for comparison. FIG. 39 shows a daily change in melatonin concentration contained in saliva for Groups T1, T2, E1, and E2. FIG. 40 shows aggregated results of questionnaires regarding subjective evaluation of sleep states for Groups T1, T2, E1, and E2. FIG. 41 shows aggregated results of questionnaires regarding the number of awakenings during sleep for Groups T1, T2, E1, and E2. FIG. 42 shows aggregated results of questionnaires regarding the time to open eyes for Groups T1, T2, E1, and E2. Moreover, regarding the melatonin secretion amount in FIG. 39, an average value of the measurement results of the five members was obtained and compared between groups. Meanwhile, regarding the data from the questionnaire results in FIGS. 40 to 42, the number of people who responded with a same result was classified into each group, and comparisons were made between groups. Using these data, an effect of the method for using a white light source on sleep was evaluated.

(About the Effect of Sunlight Reproduction Lighting on Sleep: Comparative Evaluation of T1 and E1)

The Group T1 consists of 5 members belonging to the tennis club, and the Group E1 consists of 5 members belonging to the ESS club. The behavior of the two groups during the camp was completely the same, except for the time of club activities. Throughout their club activities, T1 was active under outdoor sunlight and E1 was active under indoor lighting such as in a conference room, so the two groups spent time in different environments, but other than that, the time schedule of daily life and the conditions of indoor lighting (color temperature, illuminance, A/B ratio)

were same (Table 15). Therefore, if differences in lighting environments have any effect on sleep, the difference between the two groups is due to the difference in whether the club activities are done indoors or outdoors. However, the color temperature and illuminance of the lighting received by E1 indoors were reproduced based on actual measurements of the color temperature and illuminance changes of sunlight. In addition, the A/B ratio was not reproduced based on actual measurements of sunlight, but was based on the α-opic irradiance of black body radiation of the same color temperature, and was at a level that could be considered practically equivalent to sunlight.

When confirming the change in melatonin secretion in FIG. 39, it can be seen that only the results of T1 and E1 among the four groups are outstanding, and the graphs of T1 and E1 almost overlap with each other, showing that both are at approximately a same level. In addition, looking at the result of the sleep quality evaluation (number of awakenings during sleep) in FIG. 41, or the result of the awakening evaluation (difference between the time to open eyes and the starting time of lights-on) in FIG. 42, the data of E1 was comparable to the data of T1.

From these three types of comparative data, when comparing two types of illumination light in terms of the secretion of melatonin and the degree of influence on sleep, both sunlight and the white light source of the present disclosure are at an almost same level, and thus, it can be seen that the characteristics of the white light source of the present disclosure, which aims to reproduce the luminescence characteristics of sunlight, are at a level that may sufficiently satisfy the purpose of the invention.

(About the Effect of Melanopic Irradiance on Sleep (1): Comparative Evaluation of T1 and T2)

Both T1 and T2 are composed of members belonging to the tennis club. The two groups performed same activities under a same lighting environment in group activities such as club activities and meals, but a lighting environment during free time was different. Among the lighting conditions, there was no change in color temperature or illuminance between the two, but for the A/B ratio, a ratio for T1 was approximately 1.00, which was within the scope of the provisions of the present invention, but a ratio for T2 was about 1.15, which was a value exceeding the upper limit of the provisions of the present invention.

Figure 43:
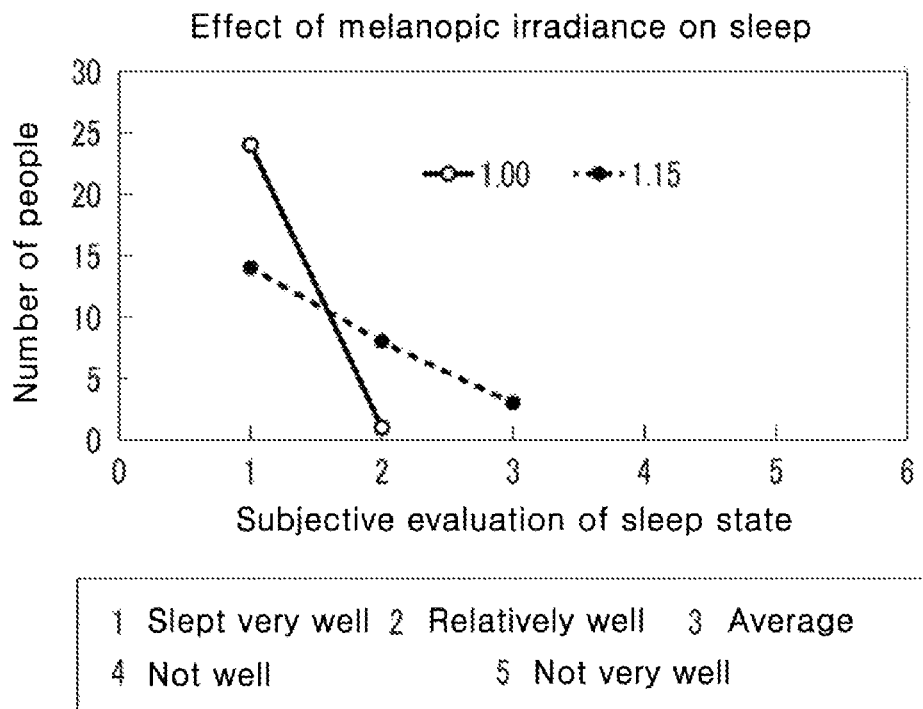
FIG. 43 is a diagram showing relationships between subjective evaluation data of sleep state and A/B ratios for Groups T1 and T2.

First, comparing the secretion amounts of melatonin from the graph in FIG. 39, T2 showed a clearly lower value compared to T1. In addition, looking at the daily change in secretion amount, T1 showed a flat and stable course that was generally close to a straight line, but T2 showed a tendency to be somewhat unstable, with larger irregularities and a greater range of changes compared to T1. Because the members of T2 received light from a white light source with a high ratio of melanopic irradiance before going to bed, it is thought that the ipRGC received excessive light, which acted to suppress the secretion of melatonin. In addition, an increase/decrease in melatonin secretion in T2 was greater than that in T1, and the increase/decrease increased over the latter half of the camp, and there is a possibility that excessive stimulation of ipRGC accumulated over time caused disruption of daily rhythm. Next, the results of the survey on sleep quality are summarized in FIG. 43. Because both T1 and T2 members were getting enough exercise under sunlight, their sleep quality was generally good. However, when comparing the effect of A/B ratio on sleep, there is a difference between the two. Most of the members who received appropriate illumination light with the A/B ratio of 1.00 responded that they slept very well, while among members who received illumination light with the A/B ratio of 1.15, which is higher than the upper limit, the number of members who said that they slept relatively well or that they slept as usual was increasing, showing a trend of decreasing sleep quality.

Figure 44:
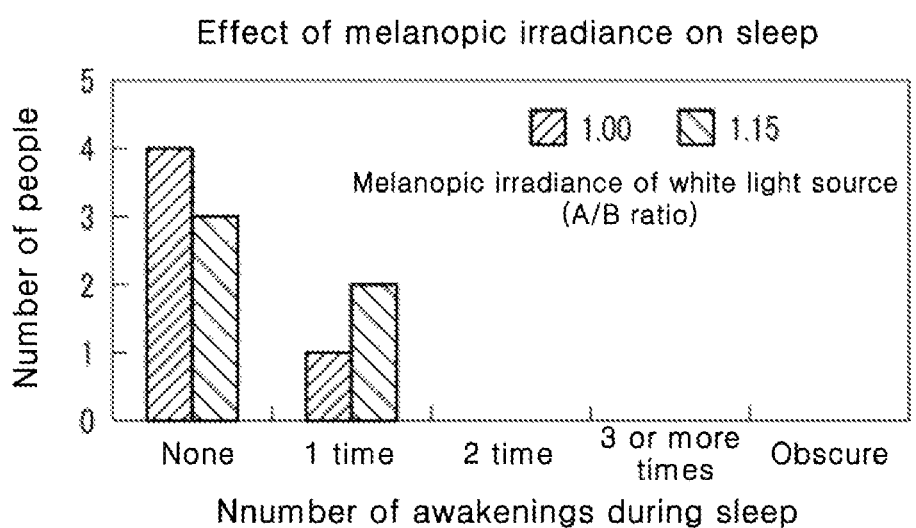
FIG. 44 is a diagram showing relationships between the number of awakenings during sleep and A/B ratios for Groups T1 and T2.
Figure 45:
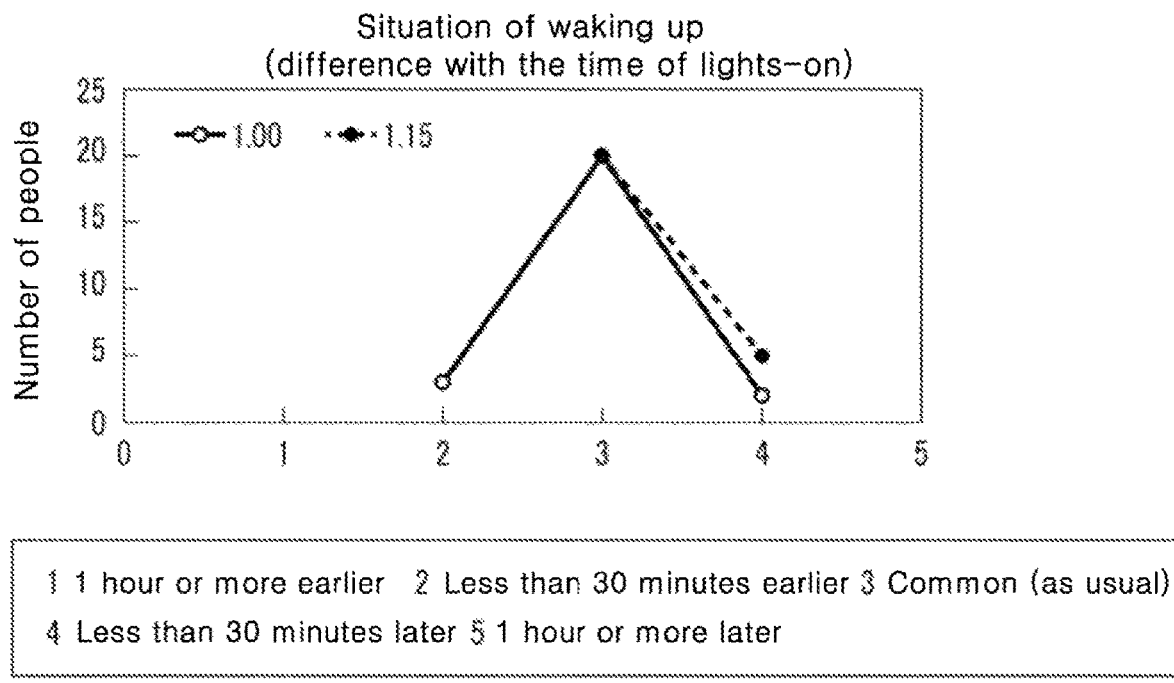
FIG. 45 is a diagram showing relationships between eye-opening time data and A/B ratios for Groups T1 and T2.

FIG. 44 shows aggregated results of the questionnaire regarding the number of awakenings during sleep. Regardless of a size of the A/B ratio, a most common response was "none," but among the responses of "none," there was one more member among the members the who received illumination light with the appropriate A/B ratio than the members who received light with the A/B ratio higher than the upper limit, and during the 5 days of sleep, a difference in the number of members who answered "opened my eyes once" was the opposite of the above. Therefore, the members who received illumination light with the appropriate A/B ratio tended to have better sleep quality. FIG. 45 shows a time difference between the time to open their eyes in the morning and the time of lights-on. For both members, a most common response was "I opened my eyes at the same time when lights were turned on," but among the members who received illumination light with the appropriate A/B ratio, there were a total of 3 members who opened their eyes earlier than the lighting time, and 0 members who opened their eyes later than the lighting time, whereas among the members who received illumination light with the A/B ratio greater than the upper limit, there were a total of 5 members who opened their eyes later than the lighting time, and no members who opened their eyes earlier than the lighting time. Regarding the fact that among the members who received illumination light with the appropriate A/B ratio, there were members who opened their eyes early when the lights were turned on, (1) in the sleep quality survey, many of these members responded that they "slept very well", so waking up early was a result of sleeping well, and (2) at 7 o'clock, which was the wake-up time, the indoor lighting was dark due to the effect of the curtains, but since the outdoor area was already bright, it can be judged that the time of waking up was rather appropriate, which was the result of the proper daily rhythm functioning. Meanwhile, regarding the fact that among the members who received illumination light with the A/B ratio exceeding the upper limit, there were many members who woke up late, if we consider that (1) they continued to sleep without noticing the lights-on even though the room became brighter; (2) it was already bright outside and it would already be the time for them to be awake if it had not been for the camp, it can be said that there was an unfavorable trend regarding daily rhythm.

From the above results, it can be seen that between the members who received illumination light with the appropriate A/B ratio and the members who received illumination light with the A/B ratio higher than the upper limit, there was a difference between the two in terms of sleep quality, waking up during sleep, or waking time, and the former showed a preferable trend to the latter. Therefore, it was confirmed that the white light source with the appropriate A/B ratio maintains appropriate amounts of stimulation light for photoreceptor cells (ipRGC), thereby maintaining an appropriate amount of melatonin secretion and contributing to maintaining a normal daily rhythm.

(About the Effect of Melanopic Irradiance on Sleep (2): Comparative Evaluation of E1 and E2)

Both E1 and E2 are composed of members belonging to the ESS club. Both groups performed same activities under a same lighting environment for group activities excluding club activities, but lighting environments at other times were different. Among the lighting conditions, there was no difference in color temperature or illuminance between the two, but with respect to the A/B ratio, a ratio for E1 was about 1.00, which was within the range specified in the present disclosure, but a ratio for E2 was about 0.75, which was a value below the upper limit of the provisions of the present invention.

Figure 46:
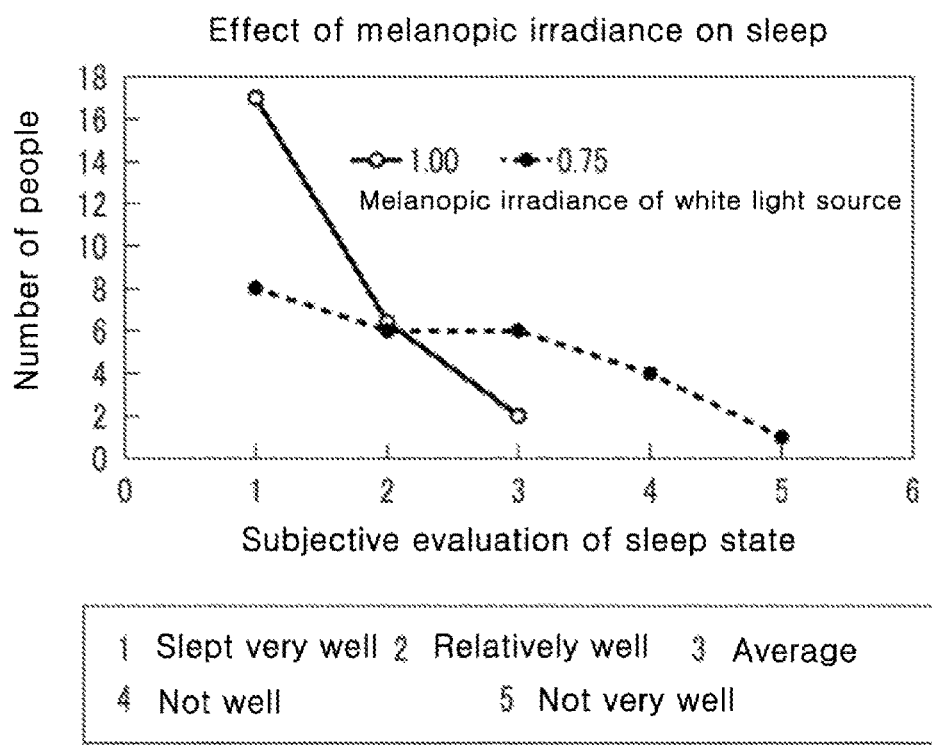
FIG. 46 is a diagram showing relationships between subjective evaluation data of sleep state and A/B ratios for Groups E1 and E2.
Figure 47:
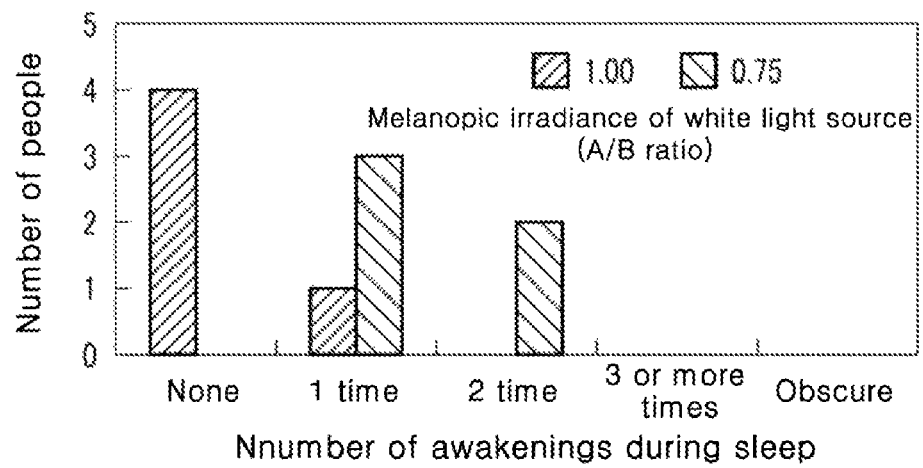
FIG. 47 is a diagram showing relationships between the number of awakenings during sleep and A/B ratios for Groups E1 and E2.

First, comparing the secretion amount of melatonin from the graph in FIG. 39, E1 showed a result that it always fell below E1, rather than exceeding E1, compared to E2. In addition, while the daily change in E1 was relatively stable, a range of change in secretion amount in E2 was large, showing a change curve with a concavo-convex shape. Since the range of change in secretion increased in the latter half of the camp, it is possible that the daily rhythm was beginning to become disturbed as the time under illumination became longer. FIG. 46 is a collection of results of subjective evaluation of sleep state. There was a clear difference in sleep quality between the members who received illumination light with the appropriate A/B ratio and the members who received light from the light source with the A/B ratio less than the lower limit. All members who received illumination light with the appropriate A/B ratio reported a state that they were able to sleep as usual or better than usual, whereas in a case of the members who received the light source with the A/B ratio lower than the lower limit, almost half of the members responded that they "slept very well," but a distribution of results expanded to various states such as from "as usual" to "not slept well." In addition, there were 25% of members who responded "I didn't sleep very well" or "I didn't sleep well." Among the four groups, E2 was the only group that responded that their sleep quality was worse than usual, making them stand out as an unusual group. FIG. 47 shows aggregated results of the number of awakenings during sleep. There was also a big difference in the number of awakenings between E1 and E2 members. In E1, there were 4 members who answered "I never woke up," while in E2, there were 0 people, and meanwhile, in E2, there were 2 members who responded, "I woke up twice," but in E1, there were 0 people.

Figure 48:
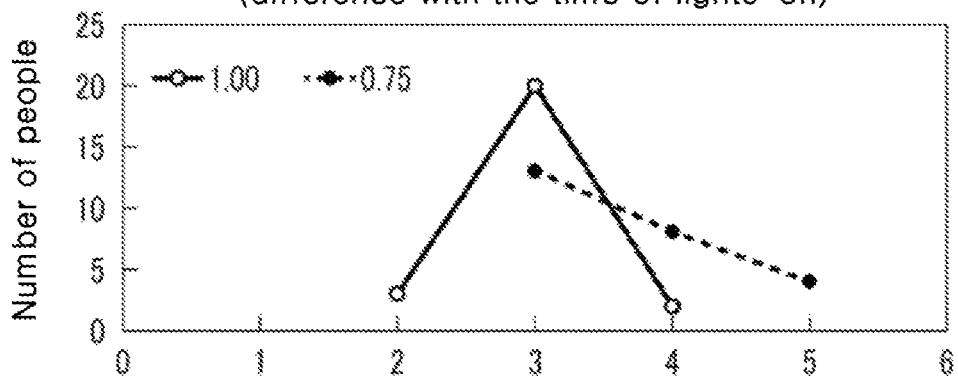
FIG. 48 is a diagram summarizing relationships between eye-opening time data and A/B ratios for Groups E1 and E2.

FIG. 48 is a diagram summarizing results of the questionnaire regarding the waking time. In this result, as in other cases, E1 showed a better result than E2, and the difference between the two was clear. In both cases, a most common response was 'the same time when lights were turned on', but in E2, the number of members who woke up later than the time of lights-on increased, and the number of members who woke up at a different time than the time of lights-on increased, furthermore, their awakening times were only later than the time of lights-on. The E2 members were clearly inferior to the other group members in the sleep quality evaluation results, and the reason for the delayed awakening time appears to be due to an unstable circadian rhythm.

As a result of comparing two types of white lighting with different A/B ratios as described above, in the lighting with the A/B ratio lower than the lower limit, a result that the secretion of melatonin or quality of sleep was lower than when the A/B ratio was appropriate was obtained. It seems that as the melanopic irradiance falls below the appropriate level, the amount of stimulation light for the ipRGC is less than the appropriate level, resulting in a decrease in melatonin secretion and instability, which results in the daily rhythm not being maintained properly, thereby leading to a decrease in sleep quality.

(Comprehensive Evaluation Results)

As a result of the evaluation, it was confirmed that there was the difference in the evaluation results among the experimental participants groups. In the group using the lighting within the scope of the present disclosure, the melatonin concentration was high, there was a tendency of "sleep well" in the subjective evaluation of the sleep state, and there was a tendency of having fewer awakenings in the evaluation of the quality of sleep, and thus, an earlier tendency was recognized in the evaluation of the difference between the time of eye opening and the time of lights-on.

Therefore, it can be verified from the results of this embodiment that a judgment criterion A/B ratio for judging the appropriate range and the appropriate range of the light emitting characteristic in the present disclosure for a white light source that has a suitable effect on a person's daily rhythm or sleep quality is reasonable.

Inventive Example 10

Details of white light sources Spl 1 to Spl 9 of which the results are shown in FIG. 19A are as shown in Table 3, and the A/B ratios of the white light sources Spl 1 to Spl 9 are shown in Table 20. In Table 20, the details of the white light source shown in Table 3 and the sleep quality shown in FIGS. 19A and 19B are shown again.

In addition, color temperature, correlated color temperature, α-opic irradiance ratio (melanopic irradiance/(L-cone-opic irradiance+M-cone-opic irradiance)), color rendering, A/B ratio, and sleep quality of white light sources Spl 10 and Spl 1 are shown in Table 20. Meanwhile, color temperature, correlated color temperature, α-opic irradiance ratio (melanopic irradiance/(L-cone-opic irradiance+M-cone-opic irradiance)), color rendering, A/B ratio, and sleep quality of white light sources from Spl 12 to 23 are shown in Table 21. The method for evaluating sleep quality is same as that described above.

TABLE 20

| Color temperature (K) | Light source No | Correlated color temperature | A/B ratio(%) * | A/B ratio | Color rendering (Ra) | Quality of sleep |
|---|---|---|---|---|---|---|
| 2900 | Spl 1 | 2910 K + 0.001duv | 19.9 | 0.84 | 95 | Δ B |
|  | Spl 2 | 2900 K + 0.000duv | 24.8 | 1.05 | 97 | ⊚ A |
|  | Spl 3 | 2910 K + 0.001duv | 29.1 | 1.23 | 87 | X C |
| 4000 | Spl 4 | 4020 K + 0.001duv | 25.1 | 0.79 | 79 | X C |
|  | Spl 5 | 3990 K + 0.002duv | 29.5 | 0.92 | 98 | ⊚ A |
|  | Spl 6 | 3980 K + 0.001duv | 35.7 | 1.13 | 95 | Δ B |
| 5000 | Spl 7 | 5020 K + 0.002duv | 30.9 | 0.83 | 73 | X C |
|  | Spl 8 | 5000 K + 0.000duv | 35.1 | 0.94 | 95 | ⊚ A |
|  | Spl 9 | 5030 K + 0.001duv | 39.5 | 1.06 | 99 | ⊚ A |

TABLE 20-continued

| Color temperature (K) | Light source No | Correlated color temperature | ratio(%) * | A/B ratio | Color rendering (Ra) | Quality of sleep |
|---|---|---|---|---|---|---|
| | Spl 10 | 4995 K + 0.000duv | 37.5 | 1.01 | 99 | ◎ A |
| | Spl 11 | 4980 K + 0.002duv | 42.4 | 1.14 | 90 | X C | is melanopic irradiance/(L-cone opic irradiance+M-cone opic irradiance)

TABLE 21

| Light source No | Correlated color temperature | ratio(%) * | A/B ratio | Color rendering (Ra) | Quality of sleep |
|---|---|---|---|---|---|
| Spl 12 | 2900K − 0.001 duv | 23.93 | 1.01 | 99 | ◎ A |
| Spl 13 | 3140K + 0.001 duv | 23.20 | 0.91 | 92 | ◎ A |
| Spl 14 | 3200K + 0.000 duv | 27.59 | 1.06 | 97 | ◎ A |
| Spl 15 | 3460K + 0.002 duv | 31.10 | 1.13 | 89 | Δ B |
| Spl 16 | 3785K + 0.000 duv | 31.72 | 1.09 | 94 | ◎ A |
| Spl 17 | 4000K + 0.001 duv | 30.06 | 0.94 | 98 | ◎ A |
| Spl 18 | 4320K − 0.002 duv | 29.24 | 0.87 | 90 | Δ B |
| Spl 19 | 4560K + 0.002 duv | 39.80 | 1.14 | 88 | × C |
| Spl 20 | 4595K + 0.001 duv | 33.03 | 0.94 | 95 | ◎ A |
| Spl 21 | 4760K − 0.002 duv | 30.83 | 0.86 | 90 | × C |
| Spl 22 | 4995K + 0.000 duv | 37.40 | 1.01 | 99 | ◎ A |
| Spl 23 | 5000K − 0.002 duv | 41.24 | 1.13 | 89 | × C | is melanopic irradiance/(L-cone opic irradiance+M-cone opic irradiance)

As can be seen from Tables 20 and 21 and FIG. 19B, if a light source has an A/B ratio within a range of 0.88 or more and 1.11 or less, that is, the light source is within a region defined by a curve L5 and a curve L6 in FIG. 19B, and it indicates that the sleep quality is Grade A, and if a light source of which the A/B ratio is outside a range defined by an upper limit (1.11) and a lower limit (0.88), it indicates that the sleep quality is Grade B or C.

In addition, among the light sources with Grade A sleep quality, light sources with the A/B ratio in a more preferable range (0.92 to 1.07) tended to show a stable high secretion amount of melatonin and to have a high average color rendering index Ra of 95 or more. In particular, light sources on a linear line and in a vicinity thereof shown in FIG. 19A, that is, light sources on a solid line L4 and in a vicinity thereof in FIG. 19B, tended to obtain characteristics with an Ra of 97 or higher, close to 100.

By using a white light source under a condition of meeting a criteria of 0.88≤A/B≤1.11, a person's daily rhythm may be properly maintained, and thus, favorable sleep quality may be obtained.

Although several embodiments of the present disclosure have been described, these embodiments are presented as examples and are not intended to limit the scope of the invention. These novel embodiments can be implemented in other various forms, and various omissions, substitutions, and changes can be made without departing from the gist of the invention. Embodiments and modifications thereof are included in the scope and gist of the invention, and are included in the scope of the invention described in the claims and equivalents thereof.

DESCRIPTION OF REFERENCE NUMERALS

1 ... LED module, 2 ... Substrate, 3 ... Housing portion, 4 ... LED chip, 5 ... Conductive portion, 10 ... LED module, 11 ... Substrate, 12 ... Dam, 13 ... LED chip, 14 ... Bonding interconnection, 15 ... Bonding pad portion, 16 ... Interconnection pattern, 17 ... Electrode, 18 ... Phosphor layer, 19 ... Solder resist layer, 20 ... LED module, 21 ... Electrode, 22 ... LED chip, 23 ... Bonding interconnection, 24 ... Phosphor layer, 25 ... Resin mold, 31 ... Substrate, 32 ... LED chip, 33 ... Phosphor layer, 34 ... Transparent resin layer, 40 ... Emission spectrum, 41 ... Excitation spectrum, 42 ... Emission spectrum, 43 ... Excitation spectrum, 51 ... White light source portion, 52 ... Control portion, 53 ... Substrate, 54 ... White light source, 55 ... Light emitting device enclosure, 56 ... LED chip, 57 ... Phosphor layer, 58 ... Control portion, 59 ... Electronic circuit memory, 60 ... Data input/output portion, 61 ... Interconnection, 80 ... LED chip, 81 ... Substrate, 82 ... N-type semiconductor layer, 83 ... Active layer, 84 ... P-type semiconductor layer, 85 ... P-type electrode, 86 ... N-type electrode, 90 ... LED chip, 91 ... Substrate, 92 ... N-type semiconductor layer, 93 ... Active layer, 94 ... P-type semiconductor layer, 95 ... P-type electrode, 96 ... N-type electrode, 97 ... Submount board, 100 ... LED device, 101 ... LED chip, 102 ... LED chip, 103 ... Phosphor layer, 104 ... Transparent resin layer, 105 ... Molding member, 106 ... Lead.

The invention claimed is:

1. A white light source that emits light with a correlated color temperature in a range of 2500K or more to 10000K or less, wherein, when amounts of stimulation light that the white light source irradiates to photoreceptor cells of ipRGC, L cone, and M-cone among human photoreceptor cells are set as melanopic irradiance, L cone optic irradiance, and M-cone optic irradiance, respectively, a ratio of the stimulation light amounts is expressed by the following formula (1), and when the ratio corresponding to an emission spectrum of the above-described white light source is A, and the ratio corresponding to a spectrum of blackbody radiation having a same color temperature as that of the white light source is B, the following formula (2) is satisfied.

$$\text{Melanopic irradiance}/(L \text{ cone optic irradiance} + M \text{ cone optic irradiance}) \quad (1)$$

$$0.88 \leq A/B \leq 1.11 \quad (2)$$

2. The white light source of claim 1, wherein a relationship expressed as following formula (3) is established between the ratio A and the ratio B.

$$0.92 \leq A/B \leq 1.07 \quad (3)$$

3. The white light source of claim 1, wherein a deviation of the correlated color temperature from a color temperature on a locus of black body radiation is within a range of ±0.005.

4. The white light source of claim 3, wherein the white light source includes an LED chip and a phosphor layer, and the phosphor layer directly or indirectly covers a periphery of the LED chip.

5. The white light source of claim 4, wherein light emitted from the LED chip has an emission peak between a wavelength of 360 nm and 470 nm.

6. The white light source of claim 5, wherein in the white light source, the LED chip is constituted with a plurality of LED chips having different emission peak wavelengths, and the phosphor layer contains a mixture of a plurality of types of phosphors having different emission peak wavelengths.

7. The white light source of claim 1, wherein an average color rendering index Ra of white light emitted from the white light source is 95 or more, and all of color rendering indices R1 to R8, and special color rendering indices R9 to R15 are 85 or higher.

8. The white light source of claim 7, wherein the average color rendering index Ra of white light emitted from the white light source is 97 or more, and all of the color rendering indices R1 to R8, and the special color rendering indices R9 to R15 are 90 or higher.

9. The white light source claim 1, wherein when a chromaticity change at an initial stage of lighting of the white light source and after continuous lighting for 6000 hours is expressed as a change in chromaticity on a CIE chromaticity diagram, the chromaticity change is less than 0.01.

10. The white light source of claim 1, wherein peak wavelength intervals between adjacent peaks of emission spectrums of a plurality of types of phosphors included in a mixture of phosphors are 150 nm or less.

11. The white light source of claim 10, wherein each type of phosphor included in the mixture of phosphors exhibits an emission spectrum having a full width at half maximum of 50 nm or more.

12. The white light source of claim 11, wherein the emission spectrum of each type of phosphor included in the mixture of phosphors has a different peak wavelength, and a portion of each emission spectrum has at least one wavelength region overlapping with another emission spectrum.

13. A white light source that emits white light with a correlated color temperature in a range of 2500K or more to 10000K or less, comprising:
a substrate;
a housing portion installed on a surface of the substrate;
an electrode disposed on the surface or a rear surface of the substrate;
an interconnection pattern disposed on the surface or rear surface of the substrate;
one or more GaN-based LED chips disposed in an electrically connected state to the electrode or the interconnection pattern in the housing portion; and
a phosphor layer including various kinds of phosphors having different luminous colors disposed in the housing portion,
wherein, when amounts of stimulation light that the white light source irradiates to photoreceptor cells of ipRGC, L cone, and M-cone among human photoreceptor cells are set as melanopic irradiance, L cone optic irradiance, and M-cone optic irradiance, respectively, a ratio of the stimulation light amounts is expressed by the following formula (1), and when the ratio corresponding to the emission spectrum of the above-described white light source is A, and the ratio corresponding to the spectrum of blackbody radiation having the same color temperature as that of the white light source is B, the following formula (2) is satisfied.

Melanopic irradiance/($L$ cone optic irradiance+$M$ cone optic irradiance)     (1)

$0.88 \leq A/B \leq 1.11$     (2)

14. The white light source of claim 13, wherein a relationship expressed as following formula (3) is established between the ratio A and the ratio B.

$0.92 \leq A/B \leq 1.07$     (3)

15. The white light source of claim 13, wherein a deviation of the correlated color temperature from a color temperature on a locus of black body radiation is within a range of ±0.005.

16. The white light source of claim 15, wherein the white light source further comprises a transparent resin layer formed on an inner or outer surface of the phosphor layer, and the transparent resin layer contains particulate inorganic compounds.

17. The white light source of claim 16, wherein the inorganic compound is contained in the transparent resin layer in a range of 0.1% by mass to 5% by mass.

18. The white light source of claim 13, wherein the substrate is constituted with one of resin, metal, and ceramics.

19. The white light source of claim 18, further comprising a reflection layer provided on the surface of the substrate, wherein the metal is at least one selected from a group consisting of aluminum, aluminum alloy, copper, stainless steel, magnesium alloy, and iron.

20. The white light source of claim 19, wherein the reflection layer includes a binder matrix and inorganic particles dispersed in the binder matrix, and
the inorganic particles are at least one selected from a group consisting of aluminum oxide, zirconium oxide, titanium oxide, and barium oxide.

21. The white light source of claim 19, further comprising a transparent insulation film that covers at least a portion of a surface of the reflection layer.

22. The white light source of claim 13, wherein an Au film is formed on at least a portion of a surface of the electrode and/or the interconnection pattern.

23. The white light source of claim 22, wherein the electrode is constituted with a laminated body including prepreg and metal foil, a white solder resist film is formed on an outermost surface of the electrode, and the white solder resist film has characteristics of electrical insulation and resistance to UV rays.

24. The white light source of claim 13, further comprising a transparent insulation film covering the LED chip.

25. The white light source of claim 13, wherein the substrate is constituted with a resin molded lead frame, and the resin molding includes reflective material and silicone resin or epoxy resin to function as a reflector.

26. A white light source configured to emit white light with a correlated color temperature in a range of 2500K or more to 10000K or less, the white light source comprising:
one or more light emitting diodes; and
a phosphor layer including various kinds of phosphors having different luminous colors, the phosphor layer covering the one or more light emitting diodes,
wherein, when amounts of stimulation light that the white light source irradiates to photoreceptor cells of ipRGC, L cone, and M-cone among human photoreceptor cells are set as melanopic irradiance, L cone optic irradiance, and M-cone optic irradiance, respectively, a ratio of the stimulation light amounts is expressed as the melanopic irradiance divided by a sum of the L cone optic irradiance and the M cone optic irradiance, and when the ratio corresponding to an emission spectrum of the white light source is A, and the ratio corresponding to a spectrum of blackbody radiation having a same color temperature as that of the white light source is B, A/B is greater than or equal to 0.88 and less than or equal to 1.11.

* * * * *